US007279168B2

(12) United States Patent
Winslow et al.

(10) Patent No.: US 7,279,168 B2
(45) Date of Patent: *Oct. 9, 2007

(54) RECOMBINANT VIRUS EXPRESSING FOREIGN DNA ENCODING FELINE CD86 AND USES THEREOF

(75) Inventors: Barbara J. Winslow, Del Mar, CA (US); Mark D. Cochran, Carlsbad, CA (US); Stephen Hash, Austin, TX (US); Insoo Choi, Seoul (KR); Ellen Collisson, College Station, TX (US)

(73) Assignees: Texas A & M University System, College Station, TX (US); Schering-Plough Animal Health Corporation, Summit, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/303,040

(22) Filed: Apr. 30, 1999

(65) Prior Publication Data

US 2002/0051792 A1 May 2, 2002

Related U.S. Application Data

(60) Provisional application No. 60/083,870, filed on May 1, 1998.

(51) Int. Cl.

| | |
|---|---|
| ***A61K 39/00*** | (2006.01) |
| ***A61K 39/02*** | (2006.01) |
| ***A61K 39/12*** | (2006.01) |
| ***A61K 39/21*** | (2006.01) |
| ***A61K 39/205*** | (2006.01) |

(52) U.S. Cl. ................................ 424/207.1; 424/199.1; 424/204.1; 424/224.1; 424/229.1; 424/234.1

(58) Field of Classification Search .............. 424/199.1, 424/204.1, 207.1, 224.1, 229.1, 234.1; 536/23.1, 536/23.5, 23.72, 24.1; 435/69.1, 252.3, 320.1; 514/44; 56/350

See application file for complete search history.

(56) References Cited

U.S. PATENT DOCUMENTS

| | | | | |
|---|---|---|---|---|
| 5,656,275 A | | 8/1997 | Wasmoen et al. | 424/199.1 |
| 5,861,310 A | * | 1/1999 | Freeman et al. | 435/325 |
| 6,045,802 A | | 4/2000 | Schlom et al. | 424/199.1 |
| 6,548,068 B1 | | 4/2003 | Schlom et al. | 424/199.1 |
| 6,723,705 B1 | * | 4/2004 | Freeman et al. | 514/44 |
| 2002/0028208 A1 | | 3/2002 | Collisson et al. | |

FOREIGN PATENT DOCUMENTS

| | | | |
|---|---|---|---|
| EP | 0 576 092 A1 | | 12/1993 |
| WO | WO 92/00092 | | 1/1992 |
| WO | WO 92/15671 | | 9/1992 |
| WO | WO 93/00431 | | 1/1993 |
| WO | WO 94/03621 | | 2/1994 |
| WO | WO 95/03408 | * | 2/1995 |
| WO | WO 96/03435 | | 2/1996 |
| WO | WO 96/10419 | | 4/1996 |
| WO | WO 96/40268 | | 12/1996 |
| WO | WO 96/40915 | | 12/1996 |
| WO | WO 98/04684 | | 2/1998 |

OTHER PUBLICATIONS

Tripathy D. N. Swinepox virus as a vaccine vector for swine pathogens. Advances in Veterinary Medicine (1999) vol. 41, pp. 463–480.*

Jackson et al. Expression of mouse interleukin–4 by a recombinant ectromelia virus suppresses cytolytic lymphocyte responses and overcomes genetic resistance to mousepox. Journal of Virology (2001) vol. 1205–1210.*

Brunet et al., 1987, *Nature*, 328: 267–270.

Freeman, et al., 1993, *J. Exp. Med.*, 178: 2185–2192.

Hash, S. M., 1997, EMBL Database Entry FCU57754, Accession No. U57754.

Hash, S. M., 1997, EMBL Database Entry FCU57755, Accession No. U57755.

Akeson, A.L., "A fluorometric assay for the quantitation of cell adherence to endothelial cells," *Journal of Immunological Methods*, vol. 163, pp. 181–185 (1993).

Allison, J.P. et al., "Structure, Function, and Serology of the T–cell Antigen Receptor Complex," *Annu. Rev. Immunol.*, vol. 5, pp. 503–540 (1987).

Allison, J.P., "CD28–B7 interaction in T–cell activation," *Current Opinion in Immunology*, vol. 6, pp. 414–419 (1994).

Anderson, P. et al., "Regulatory interactions between members of the immunoglobulin superfamily," *Immunology Today*, vol. 9, Nos. 7 and 8, pp. 199–203 (1988).

(Continued)

*Primary Examiner*—Bruce R. Campell
*Assistant Examiner*—Sharon Huet
(74) *Attorney, Agent, or Firm*—Morgan & Finnegan, LLP

(57) ABSTRACT

The present invention involves a recombinant virus which comprises at least one foreign nucleic acid inserted within a non-essential region of the viral genome of a virus, wherein each such foreign nucleic acid encodes a protein. The protein which is encoded is selected from the groups consisting of a feline CD28 protein or an immunogenic portion thereof, a feline cD80 protein or an immunogenic portion thereof, a feline CD86 protein or an immunogenic portion thereof, or a feline CTLA-4 protein or an immunogenic portion thereof. The protein is capable of being expressed when the recombinant virus is introduced into an appropiate host. The present invention also involves a recombinant virus further comprising a foreign nucleic acid encoding an immunogen derived from a pathogen. The present invention also comprises recombinant viruses which are capable of enhancing an immune response in a feline. The present invention also comprises recombinant viruses which are capable of suppressing an immune respons in a feline.

45 Claims, 13 Drawing Sheets

OTHER PUBLICATIONS

Antonia, S.J. et al., "B7–1 Expression by a Non–Antigen Presenting Cell–derived Tumor," *Cancer Research*, vol. 55, pp. 2253–2256 (1995).

Argyle, D.J. et al., "Nucleotide and predicted peptide sequence of feline interferon–gamma (IFN–γ)," *DNA Sequence—The Journal of Sequencing and Mapping*, vol. 5, pp. 169–171 (1995).

Arima, T. et al., "Inhibition by CTLA4Ig of Experimental Allergic Encephalomyelitis," *The Journal of Immunology*, vol. 156, pp. 4916–4924 (1996).

Arruffo, A., et al., "Molecular cloning of a CD28 cDNA by a high–efficiency COS cell expression system," *Proc. Natl. Acad. Sci. USA*, vol. 84, pp. 8573–8577 (1987).

Asjo, B. et al., "A Novel Mode of Human Immunodeficiency Virus Type 1 (HIV–1) Activation: Ligation of CD28 Alone Induced HIV–1 Replication in Naturally Infected Lymphocytes," *Journal of Virology*, vol. 67, No. 7, pp. 4395–4398 (1993).

Azuma, M. et al., "Functional Expression of B7/BB1 on Activated T Lymphocytes," J. Exp. Med., vol. 177, pp. 845–850 (1993).

Azuma, M. et al., "Involvement of CD28 in MHC–Unrestricted Cytotoxicity Mediated by a Human Natural Killer Leukemia Cell Line," The *Journal of Immunology.*, vol. 149, No. 4, pp. 1115–1123 (1992).

Azuma, M. et al., "Requirements for CD28–Dependent T Cell–Mediated Cytotoxicity," *The Journal of Immunology*, vol. 150, No. 6, pp. 2091–2101 (1993).

Azuma, M. et al.,"B70 antigen is a second ligand for CTLA–4 and CD28," *Nature*, vol. 366, pp. 76–79 (1993).

Bajorath, J. et al., "Immunoglobulin fold characteristics of B7–1 (CD80) and B7–2 (CD86)," *Protein Science*, vol. 3, pp. 2148–2150 (1994).

Bajorath, J. et al., "Knowledge–based model building of proteins: Concepts and examples," *Protein Science*, vol. 2, pp. 1798–1810 (1993).

Balzano, C. et al., "CTLA–4 and CD28: Similar Proteins, Neighbouring Genes," *Int. J. Cancer: Supplement*, vol. 7, pp. 28–32 (1992).

Barcy, S. et al., "FcR cross–linking on monocytes results in impaired T cell stimulatory capacity," *International Immunology*, vol. 7, No. 2, pp. 179–189 (1995).

Beale, D., "A Comparison of the Amino Acid Sequences of the Extracellular Domains of the Immunoglobulin Superfamily. Possible Correlations Between Conservancy and Conformation," *Comp. Biochem. Physiol.*, vol. 80B, No. 2, pp. 181–194 (1985).

Bellone, M. et al., "In vitro priming of cytotoxic T lymphocytes against poorly immunogenic epitopes by engineered antigen presenting cells," *Eur. J. Immunol.*, vol. 24, pp. 2691–2698 (1994).

Berke, G., "The Binding and Lysis of Target Cells by Cytotoxic Lymphocytes: Molecular and Cellular Aspects," *Annu. Rev. Immunol.*, vol. 12, pp. 735–773 (1994).

Berke, G., "The Functions and Mechanisms of Action of Cytolytic Lymphocytes," *Fundamental Immunology*, (W. Paul), New York: Raven Publ. 3d ed., pp. 965–1014 (1993).

Boise, L.H. et al., "CD28 Costimulation Can Promote T Cell Survival by Enhancing the Expression of Bcl–$x_L$," *Immunity*, vol. 3, pp. 87–98 (1995).

Brinchmann, J.E. et al., "Expression of Costimulatory Molecule CD28 on T Cells in Human Immunodeficiency Virus Type 1 Infection: Functional and Clinical Correlations," *The Journal of Infectious Diseases*, vol. 169, pp. 730–738 (1994).

Brown, W.C. et al., "Feline Immunodeficiency Virus Infects Both $CD4^+$ and $CD8^+$ T Lymphocytes," Journal of Virology, vol. 65, No. 6, pp. 3359–3364 (1991).

Buck, C.A., "Immunoglobulin superfamily: structure, function and relationship to other receptor molecules," *Seminars in Cell Biology*, vol. 3, pp. 179–188 (1992).

Buelens, C. et al., "Interleukin 10 differentially regulates B7–1 (CD80) and B7–2 (CD86) expression on human peripheral blood dendritic cells," *Eur. J. Immunol.*, vol. 25, pp. 2668–2672 (1995).

Caruso, A. et al., "Expression of CD28 on $CD8^+$ and $CD4^+$ Lymphocytes During HIV Infection," *Scand. J. Immunol.*, vol. 40, pp. 485–490 (1994).

Cerdan, C. et al., IL–1α is Produced by T Lymphocytes Activated Via the CD2 Plus CD28 Pathways, *The Journal of Immunology*, vol. 146, No. 2, pp. 560–564 (1991).

Chambers, C.A., et al., "Co–stimulation in T cell responses," *Current Opinion in Immunology*, vol. 9, pp. 396–404 (1997).

Chen, L. et al., "Costimulation of Antitumor Immunity by the B7 Counterreceptor for the T Lymphocyte Molecules CD28 and CTLA–4," *Cell*, vol. 71, pp. 1093–1102 (1992).

Chen, L. et al., "Costimulation of T cells for tumor immunity," *Immunology Today*, vol. 14, No. 10, pp. 483–486 (1993).

Chen, L. et al., "Induction of Cytotoxic T Lymphocytes Specific for a Syngeneic Tumor Expressing the E6 Oncoprotein of Human Papillomavirus Type 16," *The Journal of Immunology*, vol. 148, No. 8, pp. 2716–2621 (1992).

Chesnut, R.W. et al., "Antigen Presentation by B Cells and its Significance in T–B Interactions," *Advances in Immunology*, vol. 39, pp. 51–94 (1986).

Clark, S.J. et al., "High Titers of Cytopathic Virus in Plasma of Patients With Symptomatic of Primary HIV–1 Infection," *The New England Journal of Medicine*, vol. 324, No. 14, pp. 954–960 (1991).

Clayberger, C. et al., "Peptides Corresponding to the CD8 and CD4 Binding Domains of HLA Molecules Block T Lymphocyte Immune Responses In Vitro," *The Journal of Immunology*, vol. 153, pp. 946–951 (1994).

Clevers, H. et al., "The T Cell Receptor/CD3 Complex: A Dynamic Protein Ensemble," *Annu. Rev. Immunol.*, vol. 6, pp. 629–662 (1988).

Connor, R.I. et al., "Increased Viral Burden and Cytopathicity Correlate Temporarily With $CD4^+$ T–Lymphocyte Decline and Clinical Progression in Human Immunodeficiency Virus Type 1–Infected Individuals," *Journal of Virology*, vol. 67, No. 4, pp. 1772–1777 (1993).

Cooper, D.A. et al., "Characterization of T Lymphocyte Responses During Primary Infection With Human Immunodeficiency Virus," *Journal of Infectious Diseases*, vol. 157, No. 5, pp. 889–896 (1988).

Damle, N.K. et al., "Costimulation of T Lymphocyte with Integrin Ligands Intercellular Adhesion Molecule–1 or Vascular Cell Adhesion Molecule–1 Induces Functional Expression of CTLA–4, a Second Receptor for B7," *Journal of Immunology*, vol. 152, pp. 2686–2697 (1994).

Damle, N.K. et al., "Differential Regulatory Signals Delivered by Antibody Binding to the CD28 Molecule (Tp44) During the Activation of Human T Lymphocytes," *The Journal of Immunology*, vol. 140, No. 6, pp. 1753–1761 (1988).

Davis, M.M. et al., "T–cell antigen receptor genes and T–cell recognition," *Nature*, vol. 334, pp. 395–402 (1988).

de Boer, M. et al., "Ligation of B7 with CD28/CTLA–4 on T–cells results in CD40 ligand expression, interleukin–4 secretion and efficient help for antibody production by B cells," *Eur. J. Immunol.*, vol. 23, pp. 3120–3125 (1993).

deWaal, M. et al., "Direct Effects of IL–10 on Subsets of Human $CD4^+$ T Cell Clones and Resting T Cells. Specific Inhibition of IL–2 Production and Proliferation," *The Journal of Immunology*, vol. 150, No. 11, pp. 4754–4765 (1993).

Ding, L. et al., "IL–10 Inhibits Macrophage Costimulatory Activity by Selectively Inhibiting Up–Regulation of B7 Expression," *The Journal of Immunology*, vol. 151, No. 3, pp. 1224–1234 (1993).

Donnelly, J.J. et al., "DNA Vaccines," *Annu. Rev. Immunol.*, vol. 15, pp. 617–648 (1997).

Driscoll, P.C. et al., "Structure of domain 1 of rat T–lymphocyte CD2 antigen," *Nature*, vol. 353, pp. 762–765 (1991).

Ellis, J.H. et al., "Interactions of CD80 and CD86 with CD28 and CTLA4," *The Journal of Immunology*, vol. 56, pp. 2700–2709 (1996).

Engelhard, V.H., "Structure of peptides associated with MHC class I molecules," *Current Opinion in Immunology*, vol. 6, pp. 13–21 (1994).

English, R.V. et al., "Development of Clinical Disease in Cats Experimentally Infected With Feline Immunodeficiency Virus," *The Journal of Infectious Disease*, vol. 170, pp. 543–552 (1994).

Fauci, A., et al., "Acquired Immunodeficiency Syndrome: Epidemiologic, Clinical, Immunologic, and Therapeutic Considerations," *Annals of Internal Medicine*, vol. 100, pp. 92–106 (1984).

Fauci, A.S. et al., "The Effect of Hydrocortisone on the Kinetics of Normal Human Lymphocytes," *Blood*, vol. 46, No. 2, pp. 235–243 (1975).

Ferrari, F.A. et al., "Sequence Analysis of the spoOB Locus Reveals a Polycistronic Transcription Unit," *Journal of Bacteriology*, vol. 161, No. 2, pp. 556–562 (1985).

Fong, T.A.T. et al., "Alloreactive Murine $CD8^+$ T Cell Clones Secrete the Th1 Pattern of Cytokines," *The Journal of Immunology*, vol. 144, No. 5, pp. 1744–1752 (1990).

Fouchier, R.A. et al., "Broader Tropism and Higher Cytopathicity for $CD4^+$ T Cells of a Syncytium–Inducing Compared to a Non–Syncytium–Inducing HIV–1 Isolate as a Mechanism for Accelerated $CD4^+$ T Cell Decline in Vivo," *Virology*, vol. 219, pp. 87–95 (1996).

Freedman, A.S. et al., "B7, A B Cell Restricted Antigen That Identifies Preactivated B Cells," *The Journal of Immunology*, vol. 139, No. 10, pp. 3260–3267 (1987).

Freeman et al., "Structure, Expression, and T Cell Costimulatory Activity of the Murine Homologue of the Human B Lymphocyte Activation Antigen B7," *J. Exp. Med.*, vol. 174, pp. 625–631 (1991).

Freeman, G.J. et al., "B7, A New Member of the Ig Superfamily With Unique Expression on Activated and Neoplastic B Cells," *The Journal of Immunology*, vol. 143, No. 8, pp. 2714–2722 (1989).

Freeman, G.J. et al., "Uncovering a Functional Alternative CTLA–4 Counter–Receptor in B7–Deficient Mice," *Science*, vol. 262, pp. 907–909 (1993).

Gajewski, T.F. et al., "Regulation of T–Cell Activation: Differences among T–Cell Subsets," *Immunological Reviews*, vol. 111, pp. 79–110 (1989).

Germain, R.N., "The Biochemistry and Cell Biology of Antigen Processing and Presentation," *Annu. Rev. Immunol.*, vol. 11, pp. 403–450 (1993).

Gimmi, C.D. et al., "B–cell surface antigen B7 provides a costimulatory signal that induces T cells to proliferate and secrete interleukin 2," *Proc. Natl. Acad. Sci. USA*, vol. 88, pp. 6575–6579 (1991).

Haffar, O.K. et al., "Costimulation of T–cell activation and virus production by B7 antigen on activated $CD4^+$ T cells from human immunodeficiency virus type 1–infected donors," *Proc. Natl. Acad. Sci. USA*, vol. 90, pp. 11094–11098 (1993).

Harlan, D.M. et al., "Potential Roles of the B7 and CD28 Receptor Families in Autoimmunity and Immune Evasion," *Clinical Immunology and Immunopathology*, vol. 75, No. 2, pp. 99–111 (1995).

Hash, S.M., "Cloning, Sequencing, Expression and Characterization of the Feline CD28/CD80 Accessory Signaling Complex," Ph.D. Dissertation, A&M University, Texas, U.S.A. (1997).

Hassett, D.E. et al., "DNA immunization," *Trends in Microbiology*, vol. 4, No. 8, pp. 307–312 (1996).

Hathcock, K.S. et al., "Comparative Analysis of B7–1 and B7–2 Costimulatory Ligands: Expression and Function," The Journal of Experimental Medicine, vol. 180, 631–640 (1994).

Hodge, J.W. et al., "Induction of Antitumor Immunity by Recombinant Vaccinia Viruses Expressing B7–1 or B7–2 Costimulatory Molecules," *Cancer Research*, vol. 54, pp. 5552–5555 (1994).

Hutchcroft, J.E. et al., "Signaling Through CD28/CTLA–4 Family Receptors: Puzzling Participation of Phosphatidylinositol–3 Kinase," *The Journal of Immunology*, vol. 155, pp. 4071–4074 (1996).

Jenkins, M.K. et al., "CD28 Delivers a Costimulatory Signal Involved in Antigen–Specific IL–2 Production by Human T Cells," *The Journal of Immunology*, vol. 147, No. 8, pp. 2461–2466 (1991).

Jenkins, M.K. et al., "T–Cell Unresponsiveness in vivo and in vitro: Fine Specificity of Induction and Molecular Characterization of the Unresponsive State," *Immunological Reviews*, vol. 95, pp. 113–135 (1987).

June, C.H. et al., "Role of the CD28 receptor in T–cell activation," *Immunology Today*, vol. 11, No. 6, pp. 211–216 (1990).

June, C.H. et al., "The B7 and CD28 receptor families," *Immunology Today*, vol. 15, No. 7, pp. 321–333 (1994).

Knight, J.C. et al., *Virology*, vol. 190, pp. 423–433 (1992).

Kozbor, D. et al., "Tp44 Molecules Involved in Antigen–Independent T Cell Activation are Expressed on Human Plasma Cells," *The Journal of Immunology*, vol. 138, No. 12, pp. 4128–4132 (1987).

Kupfer, A. et al., "Cell Biology of Cytotoxic and Helper T Cell Functions: Immunofluorescence Microscopic Studies of Single Cells and Cell Couples," *Annu. Rev. Immunol.*, vol. 7, pp. 309–337 (1989).

Landay, A.L. et al., "An Activated CD8+ T Cell Phenotype Correlates with Anti–HIV Activity and Asymptomatic Clinical Status," *Clinical Immunology and Immunopathology*, vol. 69, No. 1, pp. 106–116 (1993).

Lane, P. et al., "B Cell Function in Mice Transgenic for mCTLA4–Hγ1: Lack of Germinal Centers Correlated with Poor Affinity Maturation and Class Switching Despite Normal Priming of $CD4^+$ T Cells," *J. Exp. Med.*, vol. 179, pp. 819–830 (1994).

Lanier, L.L. et al., "CD80 (B7) and CD86 (B70) Provide Similar Costimulatory Signals for T Cell Proliferation, Cytokine Production, and Generation of CTL," *The Journal of Immunology*, vol. 154, pp. 97–105 (1995).

Larsen, C.P. et al., "Functional Expression of the Costimulatory Molecule, B7/BB1, on Murine Dendritic Cell Populations," *J. Exp. Med.*, vol. 176, pp. 1215–1220 (1992).

Leahy, D. J. et al., "Crystal Structure of a Soluble Form of the Human T Cell Coreceptor CD8 at 2.6 Å Resolution," *Cell*, vol. 68, pp. 1145–1162 (1992).

Lechler, R.I. et al., "The molecular basis of alloreactivity," *Immunology Today*, vol. 11, No. 3, pp. 83–88 (1990).

Lenschow, D.J. et al., "CD28/B7 System of T Cell Costimulation," *Annu. Rev. Immunol.*, vol. 14, pp. 233–258 (1996).

Lenschow, D.J. et al., "Expression and functional significance of an additional ligand for CTLA–4," *Proc. Nat. Acad. Sci. USA*, vol. 90, pp. 11054–11058 (1993).

Leung, H.T. et al., "The CD28 costimulatory pathway," *Therapeutic Immunology*, vol. 1, pp. 217–228 (1994).

Lewis, D.E. et al., "Anergy and Apoptosis in CD8+ T Cells from HIV Infected Persons," *The Journal of Immunology*, vol. 153, pp. 412–420 (1994).

Li, Y. et al., "Costimulation of Tumor Reactive $CD4^+$ and $CD8^+$ T Lymphocytes by B7, a Natural Ligand for CD28, Can Be Used To Treat Established Mouse Melanoma," *The Journal of Immunology*, vol. 153, pp. 421–428 (1994).

Lindsten, T et al., "Characterization of CTLA–4 Structure and Expression on Human T Cells," *The Journal of Immunology*, vol. 151, pp. 3489–3499 (1993).

Linsley, P. S. et al., "T–cell antigen CD28 mediates adhesion with B cells by interacting with activation antigen B7/BB–1," *Proc. Natl. Acad. Sci. USA*, vol. 87, pp. 5031–5035 (1990).

Linsley, P.S. et al., "Binding of the B Cell Activation Antigen B7 to CD28 Costimulates T Cell Proliferation and Interleukin 2 mRNA Accumulation," *J. Exp. Med.*, vol. 173, pp. 721–730 (1991).

Linsley, P.S. et al., "Binding Stoichiometry of the Cytotoxic T Lymphocyte–associated Molecule–4 (CTLA–4)," *The Journal of Biological Chemistry*, vol. 270, No. 25, pp. 15417–15424 (1995).

Linsley, P.S. et al., "CD28 Ensagement by B7/BB–1 Induces Transient Down–Regulation of CD28 Synthesis and Prolonged Unresponsiveness to CD28 Signaling," *The Journal of Immunology*, vol. 150, No. 8, pp. 3161–3169 (1993).

Linsley, P.S. et al., "CD28/CTLA–4 receptor structure, binding stoichiometry and aggregation during T–cell activation," *Res. Immunol.*, vol. 146, pp. 130–140 (1995).

Linsley, P.S. et al., "Coexpression and Functional Cooperation of CTLA–4 and CD28 on Activated T Lymphocytes," *J. Exp. Med.*, vol. 176, pp. 1595–1604 (1992).

Linsley, P.S. et al., "CTLA–4 is a Second Receptor for the B Cell Activation Antigen B7," *J. Exp. Med.*, vol. 174, pp. 561–569 (1991).

Linsley, P.S. et al., "Extending the B7 (CD80) gene family," *Protein Science*, vol. 3, pp. 1341–1343 (1994).

Linsley, P.S. et al., "Human B7–1 (CD80) and B7–2 (CD86) Bind with Similar Avidities but Distinct Kinetics to CD28 and CTLA–4 Receptors," *Immunity*, vol. 1, pp. 793–801 (1994).

Linsley, P.S. et al., "Immunosuppression in Vivo by a Soluble Form of the CTLA–4 T Cell Activation Molecule," *Science*, vol. 257, pp. 792–795 (1992).

Linsley, P.S. et al., "The Role of CD28 Receptor During T Cell Responses to Antigen," *Annu. Rev. Immunol.*, vol. 11, pp. 191–212 (1993).

Littman, D.R., "The Structure of the CD4 and CD8 Genes," *Ann. Rev. Immunol.*, vol. 5, pp. 561–584 (1987).

Liu, C.C. et al., "Perforin: structure and function," *Immunololgy Today*, vol. 16, No. 4, pp. 194–201 (1995).

Liu, Y. et al., "Co–stimulation of murine CD4 T cell growth: cooperation between B7 and heat–stable antigen," *Eur. J. Immunol.*, vol. 22, pp. 2855–2859 (1992).

Lombardi, S. et al., "A Neutralizing Antibody–Inducing Peptide of the V3 Domain of Feline Immunodeficiency Virus Envelope Glycoprotein Does Not Induce Protective Immunity," *The Journal of Virology*, vol. 68, No. 12, pp. 8374–8379 (1994).

Lu, Y. et al., "CD28–Induced T Cell Activation. Evidence for a Protein–Tyrosine Kinase Signal Transduction Pathway," *The Journal of Immunology*, vol. 149, No. 1, pp. 24–29 (1992).

Lwoff, A., "The Concept of Virus," *The Journal of General Microbiology*, vol. 17, No. 1, pp. 239–253 (1957).

Martin, P.J. et al., "A 44 Kilodalton Cell Surface Homodimer Regulates Interleukin 2 Production by Activated Human T Lymphocytes," *The Journal of Immunology*, vol. 136, No. 9, pp. 3282–3287 (1986).

Matasumura, M. et al., "Emerging Principles for the Recognition of Peptide Antigens by MHC Class I Molecules," *Science*, vol. 257, pp. 927–934 (1992).

Mescher, M.F., "Surface Contact Requirements for Activation of Cytotoxic T Lymphocytes," *The Journal of Immunology.*, vol. 149, No. 7, pp. 2402–2405 (1992).

Minty, A. et al., "Interleukin–13 is a new human lymphokine regulating inflammatory and immune responses," *Nature*, vol. 362, pp 248–250 (1993).

Moffett, C.W. et al., "Microglia in the rat neurohypophysis increase expression of class I major histocompatibility antigens following central nervous system injury," *Journal of Neuroimmunology*, vol. 50, pp. 139–151 (1994).

Mosmann, T. R. et al., "TH1 and TH2 Cells: Different Patterns of Lymphokine Secretion Lead to Different Functional Properties," *Ann. Rev. Immunol.*, vol. 7, pp. 145–173 (1989).

Nabavi, N. et al., "Signaling through the MHC Class II cytoplasmic domain is required for antigen presentation and induces B7 expression," *Nature*, vol. 360, pp. 266–268 (1992).

Nagata, S. et al., "The Fas Death Factor," *Science*, vol. 267, pp. 1449–1456 (1995).

Nickoloff, B.J. et al., "Discordant Expression of CD28 Ligands, BB–1 and B7 on Keratinocytes in Vitro and Psoriatic Cells in Vivo," *American Journal of Pathology*, vol. 142, No. 4, pp. 1029–1040 (1993).

Novotney, C. et al., "Lymphocyte population changes in cats naturally infected with feline immunodeficiency virus," *AIDS*, vol. 4, pp. 1213–1218 (1990).

O'Doherty, U. et al., "Dendritic cells freshly isolate from human blood express CD4 and mature into typical immunostimulatory dendritic cells after culture in monocyte–conditioned media," *J. Exp. Med.*, vol. 178, pp. 1067–1076 (1993).

Ozawa, H. et al., "Interferon gamma and interleukin 10 inhibit antigen presentation by Langerhans cells for T helper type 1 cells by suppressing their CD80 (B7–1) expression," *Eur. J. immunol.*, vol. 26, pp. 648–652 (1995).

Page, C. et al., "Human endothelial stimulation of allogenic T cells via a CTLA–4 independent pathway," *Transplant Immunology*, vol. 2, pp. 342–347 (1994).

Peach, R. J. et al., "Both Extracellular Immunoglobulin–like Domains of CD80 Contain Residues Critical for Binding T Cell Surface Receptors CTLA–4 and CD28," *The Journal of Biological Chemistry*, vol. 270, pp. 21181–21187 (1995).

Peach, R.J. et al., "Complementarity Determining Region 1 (CDR1)– and CDR3–analogous Regions in CTLA–4 and CD28 Determine the Binding to B7–1," *J. Exp. Med.*, vol. 180, pp. 2049–2058 (1994).

Pedersen, N.C. et al., "Isolation of a T–Lymphotrophic Virus from Domestic Cats with an Immunodeficiency–Like Syndrome," *Science*, vol. 235, pp. 790–793 (1987).

Prasad, K.V.S et al., "T–cell antigen CD28 interacts with the lipid kinase phosphatidylinositol 3–kinase by a cytoplasmic Try(P)–Met–Xaa–Met motif," *Proc. Natl. Acad. Sci. USA*, vol. 91, pp. 2834–2838 (1994).

Radvanyi, L.G. et al., "CD28 Costimulation Inhibits TCR–Induced Apoptosis During a Primary T–Cell Response," *The Journal of Immunology*, vol. 156, pp. 1788–1798 (1996).

Ranheim, E.A. et al., "Tumor Necrosis Factor–α Facilitates Induction of CD80 (B7–1) and CD54 on Human B Cells By Activated T Cells: Complex Regulation by IL–4, IL–10, and CD40L," *Cellular Immunology*, vol. 161, pp. 226–235 (1995).

Razi–Wolf, Z. et al., "Expression and function of the murine B7 antigen, the major costimulatory molecule expressed by peritoneal exudate cells," *Proc. Natl. Acad. Sci. USA*, vol. 89, pp. 4210–4214 (1992).

Riley, J.L. et al., "Intrinsic Resistance to T Cell Infection with HIV Type 1 Induced by CD28 Costimulation," The *Journal of Immunology*, vol. 158, pp. 5545–5553 (1997).

Ronchese, F. et al., "Mice Transgenic for a Soluble Form of Murine CTLA–4 Show Enhanced Expansion of Antigen–Specific CD4+ T Cells and Defective Antibody Production In Vivo," *J. Exp. Med.*, vol. 179, pp. 809–817 (1994).

Rotzschke, O. et al., "Origin, structure and motifs of naturally processed MHC class II ligands," *Current Opinion in Immunology*, vol. 6, pp. 45–51 (1994).

Russel, J.H., "Internal Disintegration Model of Cytotoxic Lymphocyte–Induced Target Damage," *Immunological Rev.*, vol. 72, pp. 97–118 (1983).

Saukkonen, J.J. et al., "Expansion of a $CD8^+CD28^-$ Cell Population in the Blood and Lung of HIV–Positive Patients," *Journal of Acquired Immune Deficiency Syndromes*, vol. 6, pp. 1194–1204 (1993).

Schattner, E. et al., "HIV–Induced T–Lymphocyte Depletion," *Clinics in Laboratory Medicine*, vol. 14, No. 2, pp. 221–238 (1994).

Schmittel, A. et al., "Lipopolysacchaaride Effectively Up–Regulates B7–1 (CD80) Expression and Costimulatory Function of Human Monocytes," *Scand. J. Immunol.*, vol. 42, pp. 701–704 (1995).

Schwartz, R.H., "Costimulation of T Lymphocytes: The Role of CD28, CTLA–4 and B7/BB1 in Interleukin–2 Production and Immunotherapy," *Cell* vol. 71, pp. 1065–1068 (1992).

Seder, R.A. et al., "CD28–mediated Costimulation of Interleukin 2(IL–2) Production Plays a Critical Role in T Cell Priming for IL–4 and Interferon γ Production," *The Journal of Experimental Medicine*, vol. 179, pp. 299–304 (1994).

Shahinian, A. et al., "Differential T Cell Costimulatory Requirements in CD28–Deficient Mice," *Science*, vol. 261, pp. 609–612 (1993).

Sher, A. et al., "Role of T–Cell Derived Cytokines in the Downregulation of Immune Responses in Parasitic and Retroviral Infection," *Immunological Reviews*, No. 127, pp. 183–204 (1992).

Siebelink, K.H.J. et al., "Enhancement of Feline Immunodeficiency Virus Infection after Immunization with Envelope Glycoprotein Subunit Vaccines," *Journal of Virology*, vol. 69, No. 6, pp. 3704–3711 (1995).

Siebelink, K.H.J. et la., "Feline Immunodeficiency Virus (FIV) Infection in the Cat as a Model for HIV Infection in Man: FIV–Induced Impairment of Immune Function," *AIDS Research and Human Retroviruses*, vol. 6, No. 12, pp. 1373–1378 (1990).

Singer, S.J., "Intercellular Communication and Cell–Cell Adhesion," *Science*, vol. 255, pp. 1671–1674 (1992).

Smithgall, M.D. et al., "Costimulation of CD4+ T Cells via CD28 Modulates Human Immunodeficiency Virus Type 1 Infection and Replication in Vitro," *AIDS Research and Human Retroviruses*, vol. 11, No. 8, pp. 885–892 (1995).

Springer, T.A. et al., "The Lymphocyte Function–Associated LFA–1, CD2, and LFA–3 Molecules: Cell Adhesion Receptors of the Immune System," *Annu. Rev. Immunol.*, vol. 5, pp. 223–252 (1987).

Springer, R.T., "Adhesion receptors of the immune system," *Nature*, vol. 346, pp. 425–434 (1990).

Stack, R.M. et al., "IL–4 Treatment of Small Splenic B Cells Induces Costimulatory Molecules B7–1 and B7–2," *Journal of Immunology*, vol. 152, pp. 5723–5733 (1994).

Symington, F.W. et al., "Expression and Function of B7 on Human Epidermal Langerhans Cells," *The journal of Immunology*, vol. 150, No. 4, pp. 1286–1295 (1993).

Taylor, M.K. et al., "Cell–mediated cytotoxicity," *Current Opinion in Immunology*, vol. 4, pp. 338–343 (1992).

Thomas, R. et al., "Rheumatoid Synovium is Enriched in Mature Antigen–Presenting Dendritic Cells," *Journal of Immunology*, vol. 152, pp. 2613–2623 (1994).

Townsend, S.E. et al., "Tumor Rejection After Direct Costimulation of $CD8^+$ T Cells by B7–Transfected Melanoma Cells," *Science*, vol. 259, pp. 368–370 (1993).

Tsuji, T. et al., "Immunomodulatory effects of a plasmid expressing B7–2 on human immunodeficiency virus–1–specific cell–mediated immunity induced by a plasmid encoding the viral antigen," *Eur. J. Immunol.*, vol. 27, pp. 782–787 (1997).

Turka, L.A. et al., "CD28 is an Inducible T Cell Surface Antigen That Transduces a Proliferative Signal in $CD3^+$ Mature Thymocytes," *The Journal of Immunology*, vol. 144, No. 5, pp. 1646–1653 (1990).

Turka, L.A. et al., "Signal Transduction Via CD4, CD8, and CD28 in Mature and Immature Thymocytes," *The Journal of Immunology*, vol. 146, No. 5, pp. 1428–1436 (1991).
Unanue, E.R., "Antigen–Presenting Function of the Macrophage," *Annu. Rev. Immunol.*, vol. 2, pp. 395–428 (1984).
van Kooten, C. et al., "Monokine Production by Human T Cells: IL–1α Production Restricted to Memory T Cells," *The Journal of Immunology*, vol. 146, No. 8, pp. 2654–2658 (1991).
van Seventer, G.A. et al., "Roles of multiple accessory molecules in T–cell activation," *Current Opinion in Immunology*, vol. 3, pp. 294–303 (1991).
Wang, R. et al ., "Differential Activation of Antigen–Stimulated Suicide and Cytokine Production Pathways in CD4+ T Cells is Regulated by the Antigen–Presenting Call," *The Journal of Immunology*, vol. 150, No. 9, pp. 3832–3842 (1993).
Weiss, A. et al., "Signal Transduction by Lymphocyte Antigen Receptors," *Cell*, vol. 76, pp. 263–274 (1994).
Williams, A.F. et al., "The Immunoglobulin Superfamily––Domains for Cell Surface Recognition," *Annu. Rev. Immunol.*, vol. 6, pp. 381–405 (1988).
Windhagen, A. et al., "Expression of Costimulatory Molecules B7–1 (CD80), B7–2 (CD86) and Interleukin 12 Cytokine in Multiple Schlerosis Lesions," *J. Exp. Med.*, vol. 182, pp. 1985–1996 (1995).
Yamamoto, J.K. et al., "Epidemiologic and clinical aspects of feline immunodeficiency virus infection in cats from the continental United States and Canada and possible mode of transmission," *JAVMA*, vol. 194, No. 2, pp. 213–220 (1989).
Yasukawa, M. et al., "Differential in Vitro activation of $CD4^+CD8^-$ and $CD8^+CD4^-$ Herpes Simplex Virus–Specific Human Cytotoxic T Cells," *The Journal of Immunology*, vol. 143, No. 6, pp. 2051–2057 (1989).
Yssel, et al., "Interleukin–7 specifically induces the B7/BB1 antigen on human cord blood and peripheral blood T cells and T cell clones," *Int. Immunol.*, vol. 5, No. 7, pp. 753–759 (1993).

Zanussi, S. et al., "$CD8^+$ lymphocyte phenotype and cytokine production in long–term non–progressor and in progressor patients with HIV–1 infection," *Clin. Exp. Immunol.*, vol. 105, pp. 220–224 (1996).

Zhou, T. et al., "T cells of staphylococcal enterotoxin B–tolerized autoimmune MRL–Ipr/Ipr mice require co–stimulation through the B7–CD28/CTLA–4 pathway for activation and can be reanergized in vivo by stimulation of the T cell receptor in the absence of co–stimulatory signal," *Eur. J. Immunol.*, vol. 24, pp. 1019–1025 (1994).

Hash, S., et al. "Cloning and Sequencing of Feline B–7 and Its Counter Receptor CD28," Third International Retrovirus Research Symposium, Mar. 6–9, 1996 [Abstract].

Freeman, G. J. et al., "Murine B7–2, an Alternative CTLA4 Counter–receptor that Costimulates T Cell Proliferation and Interleukin 2 Production", *Journal of Experimental Medicine*, vol. 178(6), 1993. p. 2185–2192.

Isono, T. and Seto, A., "Cloning and Sequencing of the Rabbit Gene Encoding T–Cell Costimulatory Molecules", *Immunogenetics*, vol. 42(3), 1995, p. 217–220.

Maeda, K. et al., "Characterization of Rat CD80 and CD86 by Molecular Cloning and mAB", *International Immunology*, vol. 9(7), 1997, pp. 993–1000.

Hungarian Search Report.

* cited by examiner

FIG. 1A-1

FeB71.TAMU

ATGGGTCACGCAGCAAAGTGGAAAACACCACTACTGAAGCACCCATATCCCAAGCTCTTT 60
Met Gly His Ala Ala Lys Trp Lys Thr Pro Leu Leu Lys His Pro Tyr Pro Lys Leu Phe

CCGCTCTTGATGCTAGCTAGTCTTTTTTACTTCTGTTCAGGTATCATCCAGGTGAACAAG 120
Pro Leu Leu Met Leu Ala Ser Leu Phe Tyr Phe Cys Ser Gly Ile Ile Gln Val Asn Lys

ACAGTGGAAGAAGTAGCAGTACTATCCTGTGATTACAACATTTCCACCAAAGAACTGACG 180
Thr Val Glu Glu Val Ala Val Leu Ser Cys Asp Tyr Asn Ile Ser Thr Lys Glu Leu Thr

GAAATTCGAATCTATTGGCAAAAGGATGATGAAATGGTGTTGGCTGTCATGTCTGGCAAA 240
Glu Ile Arg Ile Tyr Trp Gln Lys Asp Asp Glu Met Val Leu Ala Val Met Ser Gly Lys

GTACAAGTGTGGCCCAAGTACAAGAACCGCACATTCACTGACGTCACCGATAACCACTCC 300
Val Gln Val Trp Pro Lys Tyr Lys Asn Arg Thr Phe Thr Asp Val Thr Asp Asn His Ser

ATTGTGATCATGGCTCTGCGCCTGTCAGACAATGGCAAATACACTTGTATTATTCAAAAG 360
Ile Val Ile Met Ala Leu Arg Leu Ser Asp Asn Gly Lys Tyr Thr Cys Ile Ile Gln Lys

ATTGAAAAAGGGTCTTACAAAGTGAAACACCTGACTTCGGTGATGTTATTGGTCAGAGCT 420
Ile Glu Lys Gly Ser Tyr Lys Val Lys His Leu Thr Ser Val Met Leu Leu Val Arg Ala

GACTTCCCTGTCCCTAGTATAACTGATCTTGGAAATCCATCTCATAACATCAAAAGGATA 480
Asp Phe Pro Val Pro Ser Ile Thr Asp Leu Gly Asn Pro Ser His Asn Ile Lys Arg Ile

ATGTGCTTAACTTCTGGAGGTTTTCCAAAGCCTCACCTCTCCTGGCTGGAAAATGAAGAA 540
Met Cys Leu Thr Ser Gly Gly Phe Pro Lys Pro His Leu Ser Trp Leu Glu Asn Glu Glu

GAATTAAATGCCATCAACACAACAGTTTCCCAAGATCCTGAAACTGAGCTCTACACTATT 600
Glu Leu Asn Ala Ile Asn Thr Thr Val Ser Gln Asp Pro Glu Thr Glu Leu Tyr Thr Ile

AGCAGTGAACTGGATTTCAATATGACAAACAACCATAGCTTCCTGTGTCTTGTCAAGTAT 660
Ser Ser Glu Leu Asp Phe Asn Met Thr Asn Asn His Ser Phe Leu Cys Leu Val Lys Tyr

FIG. 1A-2

GGAAACTTACTAGTATCACAGATCTTCAACTGGCAAAAATCAGAGCCACAGCCTTCTAAT 720
Gly Asn Leu Leu Val Ser Gln Ile Phe Asn Trp Gln Lys Ser Glu Pro Gln Pro Ser Asn

AATCAGCTCTGGATCATTATCCTGAGCTCAGTAGTAAGTGGGATTGTTGTGATCACTGCA 780
Asn Gln Leu Trp Ile Ile Ile Leu Ser Ser Val Val Ser Gly Ile Val Val Ile Thr Ala

CTTACCTTAAGATGCCTAGTCCACAGACCTGCTGCAAGGTGGAGACAAAGAGAAATGGGG 840
Leu Thr Leu Arg Cys Leu Val His Arg Pro Ala Ala Arg Trp Arg Gln Arg Glu Met Gly

AGAGCGCGGAAATGGAAAAGATCTCACCTGTCTACATAGATTCTGCAGAACCACTGTATG 900
Arg Ala Arg Lys Trp Lys Arg Ser His Leu Ser Thr

CAGAGCATCTGGAGGTAGCCTCTTTAGCTCTTCTCTACTAG 941

FIG. 2A-1

FeB71-SYNTRO

ATGGGTCACGCAGCAAAGTGGAAAACACCACTACTGAAGCACCCATATCCCAAGCTCTTT 60
Met Gly His Ala Ala Lys Trp Lys Thr Pro Leu Leu Lys His Pro Tyr Pro Lys Leu Phe

CCGCTCTTGATGCTAGCTAGTCTTTTTTACTTCTGTTCAGGTATCATCCAGGTGAACAAG 120
Pro Leu Leu Met Leu Ala Ser Leu Phe Tyr Phe Cys Ser Gly Ile Ile Gln Val Asn Lys

ACAGTGGAAGAAGTAGCAGTACTATCCTGTGATTACAACATTTCCACCAAAGAACTGACG 180
Thr Val Glu Glu Val Ala Val Leu Ser Cys Asp Tyr Asn Ile Ser Thr Lys Glu Leu Thr

GAAATTCGAATCTATTGGCAAAAGGATGATGAAATGGTGTTGGCTGTCATGTCTGGCAAA 240
Glu Ile Arg Ile Tyr Trp Gln Lys Asp Asp Glu Met Val Leu Ala Val Met Ser Gly Lys

GTACAAGTGTGGCCCAAGTACAAGAACCGCACATTCACTGACGTCACCGATAACCACTCC 300
Val Gln Val Trp Pro Lys Tyr Lys Asn Arg Thr Phe Thr Asp Val Thr Asp Asn His Ser

ATTGTGATCATGGCTCTGCGCCTGTCAGACAATGGCAAATACACTTGTATCATTCAAAAG 360
Ile Val Ile Met Ala Leu Arg Leu Ser Asp Asn Gly Lys Tyr Thr Cys Ile Ile Gln Lys

ATTGAAAAAGGGTCTTACAAAGTGAAACACCTGACTTCGGTGATGTTATTGGTCAGAGCT 420
Ile Glu Lys Gly Ser Tyr Lys Val Lys His Leu Thr Ser Val Met Leu Leu Val Arg Ala

GACTTCCCTGTCCCTAGTATAACTGATCTTGGAAATCCATCTCATAACATCAAAAGGATA 480
Asp Phe Pro Val Pro Ser Ile Thr Asp Leu Gly Asn Pro Ser His Asn Ile Lys Arg Ile

ATGTGCTTAACTTCTGGAGGTTTTCCAAAGCCTCACCTCTCCTGGCTGGAAAATGAAGAA 540
Met Cys Leu Thr Ser Gly Gly Phe Pro Lys Pro His Leu Ser Trp Leu Glu Asn Glu Glu

GAATTAAATGCCATCAACACAACAGTTTCCCAAGATCCTGAAACTGAGCTCTACACTATT 600
Glu Leu Asn Ala Ile Asn Thr Thr Val Ser Gln Asp Pro Glu Thr Glu Leu Tyr Thr Ile

AGCAGTGAACTGGATTTCAATATGACAAACAACCATAGCTTCCTGTGTCTTGTCAAGTAT 660
Ser Ser Glu Leu Asp Phe Asn Met Thr Asn Asn His Ser Phe Leu Cys Leu Val Lys Tyr

FIG. 2A-2

```
GGAAACTTAATAGTATCACAGATCTTCAACTGGCAAAAATCAGAGCCACAGCCTTCTAAT  720
Gly Asn Leu Ile Val Ser Gln Ile Phe Asn Trp Gln Lys Ser Glu Pro Gln Pro Ser Asn

AATCAGCTCTGGATCATTATCCTGAGCTCAGTAGTAAGTGGGATTGTTGTGATCACTGCA  780
Asn Gln Leu Trp Ile Ile Ile Leu Ser Ser Val Val Ser Gly Ile Val Val Ile Thr Ala

CTTACCTTAAGATGCCTAGTCCACAGACCTGCTGCAAGGTGGAGACAAAGAGAAATGGGG  840
Leu Thr Leu Arg Cys Leu Val His Arg Pro Ala Ala Arg Trp Arg Gln Arg Glu Met Gly

AGAGCGCGGAAATGGAAAAGATCTCACCTGTCTACATAG  879
Arg Ala Arg Lys Trp Lys Arg Ser His Leu Ser Thr
```

FIG. 3A-1

FeB72

```
GTTTCTGTGTTCCTCGGGAATGTCACTGAGCTTATACATCTGGTCTCTGGGAGCTGCAGT   60
GGATGGGCATTTGTGACAGCACTATGGGACTGAGTCACACTCTCCTTGTGATGGCCCTCC
Met Gly Ile Cys Asp Ser Thr Met Gly Leu Ser His Thr Leu Leu Val Met Ala Leu   120

TGCTCTCTGGTGTTTCTTCCATGAAGAGTCAAGCATATTTCAACAAGACTGGAGAACTGC
Leu Leu Ser Gly Val Ser Ser Met Lys Ser Gln Ala Tyr Phe Asn Lys Thr Gly Glu Leu   180

CATGCCATTTTACAAACTCTCAAAACATAAGCCTGGATGAGCTGGTAGTATTTTGGCAGG
Pro Cys His Phe Thr Asn Ser Gln Asn Ile Ser Leu Asp Glu Leu Val Val Phe Trp Gln   240

ACCAGGATAAGCTGGTTCTGTATGAGATATTCAGAGGCAAAGAGAACCCTCAAAATGTTC
Asp Gln Asp Lys Leu Val Leu Tyr Glu Ile Phe Arg Gly Lys Glu Asn Pro Gln Asn Val   300

ATCTCAAATATAAGGGCCGTACAAGCTTTGACAAGGACAACTGGACCCTGAGACTCCACA
His Leu Lys Tyr Lys Gly Arg Thr Ser Phe Asp Lys Asp Asn Trp Thr Leu Arg Leu His   360

ATGTTCAGATCAAGGACAAGGGCACATATCACTGTTTCATTCATTATAAAGGGCCCAAAG
Asn Val Gln Ile Lys Asp Lys Gly Thr Tyr His Cys Phe Ile His Tyr Lys Gly Pro Lys   420

GACTAGTTCCCATGCACCAAATGAGTTCTGACCTATCAGTGCTTGCTAACTTCAGTCAAC
Gly Leu Val Pro Met His Gln Met Ser Ser Asp Leu Ser Val Leu Ala Asn Phe Ser Gln   480

CTGAAATAACAGTAACTTCTAATAGAACAGAAAATTCTGGCATCATAAATTTGACCTGCT
Pro Glu Ile Thr Val Thr Ser Asn Arg Thr Glu Asn Ser Gly Ile Ile Asn Leu Thr Cys   540

CATCTATACAAGGTTACCCAGAACCTAAGGAGATGTATTTTCAGCTAAACACTGAGAATT
Ser Ser Ile Gln Gly Tyr Pro Glu Pro Lys Glu Met Tyr Phe Gln Leu Asn Thr Glu Asn   600

CAACTACTAAGTATGATACTGTCATGAAGAAATCTCAAAATAATGTGACAGAACTGTACA
Ser Thr Thr Lys Tyr Asp Thr Val Met Lys Lys Ser Gln Asn Asn Val Thr Glu Leu Tyr   660

ACGTTTCTATCAGCTTGCCTTTTTCAGTCCCTGAAGCACACAATGTGAGCGTCTTTTGTG
Asn Val Ser Ile Ser Leu Pro Phe Ser Val Pro Glu Ala His Asn Val Ser Val Phe Cys   720

CCCTGAAACTGGAGACACTGGAGATGCTGCTCTCCCTACCTTTCAATATAGATGCACAAC
Ala Leu Lys Leu Glu Thr Leu Glu Met Leu Leu Ser Leu Pro Phe Asn Ile Asp Ala Gln   780

CTAAGGATAAAGACCCTGAACAAGGCCACTTCCTCTGGATTGCGGCTGTACTTGTAATGT
Pro Lys Asp Lys Asp Pro Glu Gln Gly His Phe Leu Trp Ile Ala Ala Val Leu Val Met   840

TTGTTGTTTTTTGTGGGATGGTGTCCTTTAAAACACTAAGGAAAAGGAAGAAGAAGCAGC
Phe Val Val Phe Cys Gly Met Val Ser Phe Lys Thr Leu Arg Lys Arg Lys Lys Lys Gln   900
```

FIG. 3A-2

```
CTGGCCCCTCTCATGAATGTGAAACCATCAAAAGGGAGAGAAAAGAGAGCAAACAGACCA   960
Pro Gly Pro Ser His Glu Cys Glu Thr Ile Lys Arg Glu Arg Lys Glu Ser Lys Gln Thr

ACGAAAGAGTACCATACCACGTACCTGAGAGATCTGATGAAGCCCAGTGTGTTAACATTT
Asn Glu Arg Val Pro Tyr His Val Pro Glu Arg Ser Asp Glu Ala Gln Cys Val Asn Ile   1020

TGAAGACAGCCTCAGGGGACAAAAATCAGTAGGAAAATGGTGGCTTGGCGTGCTGACAAT
Leu Lys Thr Ala Ser Gly Asp Lys Asn Gln •                                          1080
```

Hydrophobicity plot: Feline CD86 (B7-2)

FIG. 4A

FeCD28

ATGATCCTCAGGCTGCTTCTGGCTCTCAACTTCTTCCCCTCAATTCAAGTAACAGAAAAC 60
Met Ile Leu Arg Leu Leu Leu Ala Leu Asn Phe Phe Pro Ser Ile Gln Val Thr Glu Asn

AAGATTTTGGTGAAGCAGTTGCCCAGGCTTGTGGTGTACAACAATGAGGTCAACCTTAGC 120
Lys Ile Leu Val Lys Gln Leu Pro Arg Leu Val Val Tyr Asn Asn Glu Val Asn Leu Ser

TGCAAGTACACTCACAACTTCTTCTCAAAGGAGTTCCGGGCATCCCTTTATAAGGGAGTA 180
Cys Lys Tyr Thr His Asn Phe Phe Ser Lys Glu Phe Arg Ala Ser Leu Tyr Lys Gly Val

GATAGTGCTGTGGAAGTCTGCGTTGTGAATGGAAATTACTCCCATCAGCCTCAGTTCTAC 240
Asp Ser Ala Val Glu Val Cys Val Val Asn Gly Asn Tyr Ser His Gln Pro Gln Phe Tyr

TCAAGTACAGGATTCGACTGTGATGGGAAATTGGGCAATGAAACAGTGACATTCTACCTC 300
Ser Ser Thr Gly Phe Asp Cys Asp Gly Lys Leu Gly Asn Glu Thr Val Thr Phe Tyr Leu

CGAAATTTGTTTGTTAACCAAACGGATATTTACTTCTGCAAAATTGAAGTCATGTATCCA 360
Arg Asn Leu Phe Val Asn Gln Thr Asp Ile Tyr Phe Cys Lys Ile Glu Val Met Tyr Pro

CCTCCTTACATAGACAATGAGAAGAGCAATGGGACCATTATCCACGTGAAAGAGAAACAT 420
Pro Pro Tyr Ile Asp Asn Glu Lys Ser Asn Gly Thr Ile Ile His Val Lys Glu Lys His

CTTTGTCCAGCTCAGCTGTCTCCTGAATCTTCCAAGCCATTTTGGGCACTGGTGGTGGTT 480
Leu Cys Pro Ala Gln Leu Ser Pro Glu Ser Ser Lys Pro Phe Trp Ala Leu Val Val Val

GGTGGAATCCTAGGTTTCTACAGCTTGCTAGCAACAGTGGCTCTTGGTGCTTGCTGGATG 540
Gly Gly Ile Leu Gly Phe Tyr Ser Leu Leu Ala Thr Val Ala Leu Gly Ala Cys Trp Met

AAGACCAAGAGGAGTAGGATCCTTCAGAGTGACTATATGAACATGACCCCCCGGAGGCCA 600
Lys Thr Lys Arg Ser Arg Ile Leu Gln Ser Asp Tyr Met Asn Met Thr Pro Arg Arg Pro

GGGCCCACCCGAAGGCACTACCAACCTTACGCCCCAGCACGCGACTTTGCGGCATACCGT 660
Gly Pro Thr Arg Arg His Tyr Gln Pro Tyr Ala Pro Ala Arg Asp Phe Ala Ala Tyr Arg

TCCTGACATGGACCCCTATCCAGAAGCC 688
Ser

FIG. 4B Hydrophobicity Plot: CD28
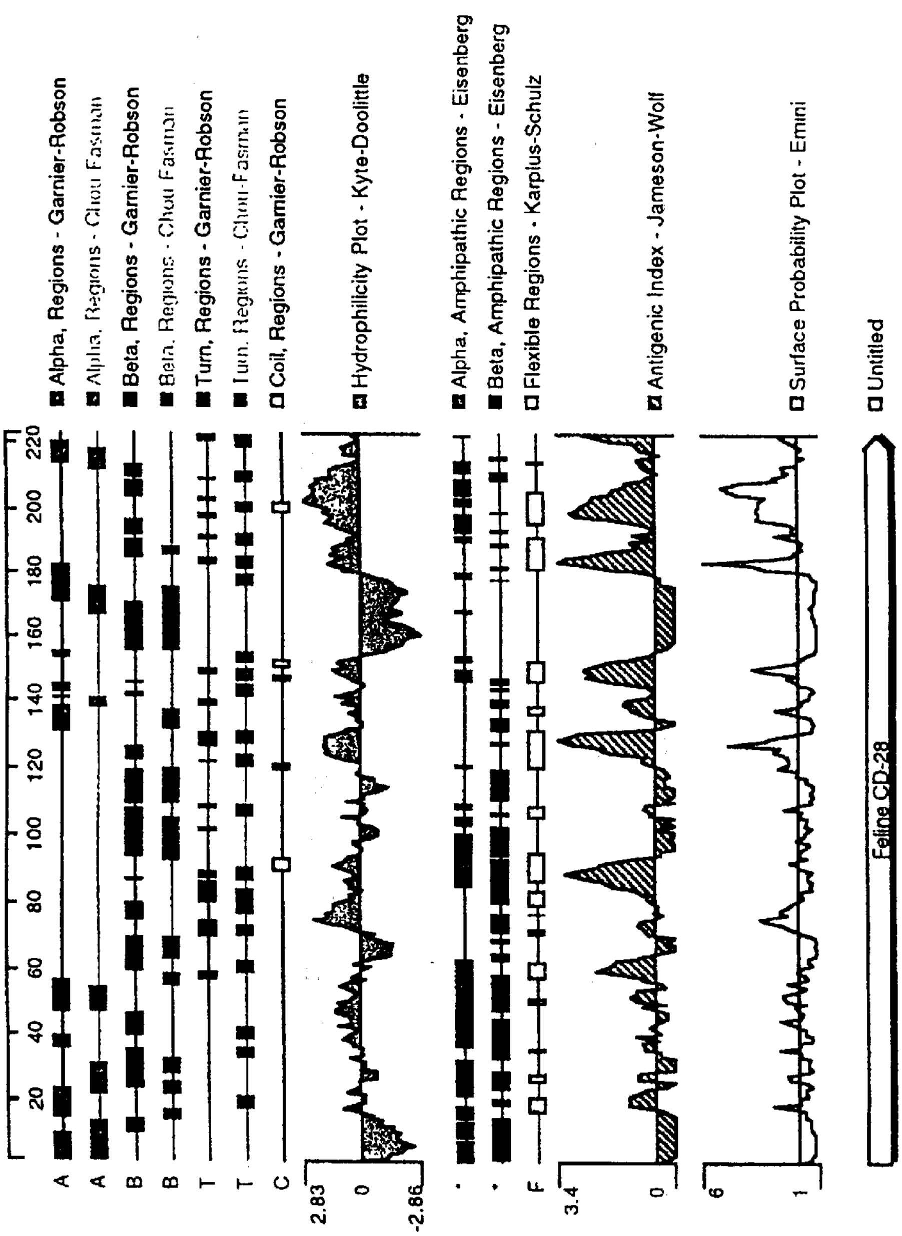

Fe CTLA4

FIG. 5A

AACCTGAACACTGCTCCCATAAAGCCATGGCTTGCTTTGGATTCCGGAGGCATGGGGCTC 60
Met Ala Cys Phe Gly Phe Arg Arg His Gly Ala

AGCTGGACCTGGCTTCTAGGACCTGGCCCTGCACTGCTCTGTTTTCTCTTCTCTTTATCC 120
Gln Leu Asp Leu Ala Ser Arg Thr Trp Pro Cys Thr Ala Leu Phe Ser Leu Leu Phe Ile

CCGTCTTCTCCAAAGGGATGCATGTGGCCCACCCTGCAGTGGTGCTGGCCAGCAGCCGAG 180
Pro Val Phe Ser Lys Gly Met His Val Ala His Pro Ala Val Val Leu Ala Ser Ser Arg

GTGTCGCCAGCTTCGTGTGTGAATATGGGTCTTCAGGCAATGCCGCCAAATTCCGAGTGA 240
Gly Val Ala Ser Phe Val Cys Glu Tyr Gly Ser Ser Gly Asn Ala Ala Lys Phe Arg Val

CTGTGCTGAGGCAAACTGGCAGCCAAATGACTGAAGTCTGTGCTGCGACATACACAGTGG 300
Thr Val Leu Arg Gln Thr Gly Ser Gln Met Thr Glu Val Cys Ala Ala Thr Tyr Thr Val

AGAATGAGTTGGCCTTCCTAAATGATTCCACCTGCACTGGCATCTCCAGCGGAAACAAAG 360
Glu Asn Glu Leu Ala Phe Leu Asn Asp Ser Thr Cys Thr Gly Ile Ser Ser Gly Asn Lys

TGAACCTCACCATCCAAGGGTTGAGGGCCATGGACACGGGACTCTACATCTGCAAGGTGG 420
Val Asn Leu Thr Ile Gln Gly Leu Arg Ala Met Asp Thr Gly Leu Tyr Ile Cys Lys Val

AGCTCATGTACCCACCACCCTACTATGCAGGCATGGGCAATGGAACCCAGATTTATGTCA 480
Glu Leu Met Tyr Pro Pro Pro Tyr Tyr Ala Gly Met Gly Asn Gly Thr Gln Ile Tyr Val

TCGATCCTGAACCTTGCCCAGATTCTGACTTCCTCCTCTGGATCCTCGCAGCAGTCAGTT 540
Ile Asp Pro Glu Pro Cys Pro Asp Ser Asp Phe Leu Leu Trp Ile Leu Ala Ala Val Ser

CAGGATTGTTTTTTTATAGCTTCCTTATCACAGCTGTTTCTTTGAGCAAAATGCTAAAGA 600
Ser Gly Leu Phe Phe Tyr Ser Phe Leu Ile Thr Ala Val Ser Leu Ser Lys Met Leu Lys

AAAGAAGCCCTCTTACTACAGGGGTCTATGTGAAAATGCCCCCAACAGAGCCAGAATGTG 660
Lys Arg Ser Pro Leu Thr Thr Gly Val Tyr Val Lys Met Pro Pro Thr Glu Pro Glu Cys

AAAAGCAATTTCAGCCTTATTTTATTCCCATCAATTGACACACCGTTATGAAGAAGGAAG 720
Glu Lys Gln Phe Gln Pro Tyr Phe Ile Pro Ile Asn •

AACACTGTCCAATTTCTAAGAGCTGAGGC 749

Hydrophobicity Plot: CTLA-4 (CD152)

SEQUENCE LISTING

<160> NUMBER OF SEQ ID NOS: 82

<210> SEQ ID NO 1
<211> LENGTH: 941
<212> TYPE: DNA
<213> ORGANISM: feline CD80
<220> FEATURE:
<221> NAME/KEY: CDS
<222> LOCATION: (1)..(876)

<400> SEQUENCE: 1 atg ggt cac gca gca aag tgg aaa aca cca cta ctg aag cac cca tat 48
Met Gly His Ala Ala Lys Trp Lys Thr Pro Leu Leu Lys His Pro Tyr
1 5 10 15 ccc aag ctc ttt ccg ctc ttg atg cta gct agt ctt ttt tac ttc tgt 96
Pro Lys Leu Phe Pro Leu Leu Met Leu Ala Ser Leu Phe Tyr Phe Cys
20 25 30 tca ggt atc atc cag gtg aac aag aca gtg gaa gaa gta gca gta cta 144
Ser Gly Ile Ile Gln Val Asn Lys Thr Val Glu Glu Val Ala Val Leu
35 40 45 tcc tgt gat tac aac att tcc acc aaa gaa ctg acg gaa att cga atc 192
Ser Cys Asp Tyr Asn Ile Ser Thr Lys Glu Leu Thr Glu Ile Arg Ile
50 55 60 tat tgg caa aag gat gat gaa atg gtg ttg gct gtc atg tct ggc aaa 240
Tyr Trp Gln Lys Asp Asp Glu Met Val Leu Ala Val Met Ser Gly Lys
65 70 75 80 gta caa gtg tgg ccc aag tac aag aac cgc aca ttc act gac gtc acc 288
Val Gln Val Trp Pro Lys Tyr Lys Asn Arg Thr Phe Thr Asp Val Thr
85 90 95 gat aac cac tcc att gtg atc atg gct ctg cgc ctg tca gac aat ggc 336
Asp Asn His Ser Ile Val Ile Met Ala Leu Arg Leu Ser Asp Asn Gly
100 105 110 aaa tac act tgt att att caa aag att gaa aaa ggg tct tac aaa gtg 384
Lys Tyr Thr Cys Ile Ile Gln Lys Ile Glu Lys Gly Ser Tyr Lys Val
115 120 125 aaa cac ctg act tcg gtg atg tta ttg gtc aga gct gac ttc cct gtc 432
Lys His Leu Thr Ser Val Met Leu Leu Val Arg Ala Asp Phe Pro Val
130 135 140 cct agt ata act gat ctt gga aat cca tct cat aac atc aaa agg ata 480
Pro Ser Ile Thr Asp Leu Gly Asn Pro Ser His Asn Ile Lys Arg Ile
145 150 155 160 atg tgc tta act tct gga ggt ttt cca aag cct cac ctc tcc tgg ctg 528
Met Cys Leu Thr Ser Gly Gly Phe Pro Lys Pro His Leu Ser Trp Leu
165 170 175 gaa aat gaa gaa gaa tta aat gcc atc aac aca aca gtt tcc caa gat 576
Glu Asn Glu Glu Glu Leu Asn Ala Ile Asn Thr Thr Val Ser Gln Asp
180 185 190 cct gaa act gag ctc tac act att agc agt gaa ctg gat ttc aat atg 624
Pro Glu Thr Glu Leu Tyr Thr Ile Ser Ser Glu Leu Asp Phe Asn Met
195 200 205 aca aac aac cat agc ttc ctg tgt ctt gtc aag tat gga aac tta cta 672
Thr Asn Asn His Ser Phe Leu Cys Leu Val Lys Tyr Gly Asn Leu Leu
210 215 220 gta tca cag atc ttc aac tgg caa aaa tca gag cca cag cct tct aat 720
Val Ser Gln Ile Phe Asn Trp Gln Lys Ser Glu Pro Gln Pro Ser Asn
225 230 235 240 aat cag ctc tgg atc att atc ctg agc tca gta gta agt ggg att gtt 768
Asn Gln Leu Trp Ile Ile Ile Leu Ser Ser Val Val Ser Gly Ile Val
245 250 255

-continued

```
gtg atc act gca ctt acc tta aga tgc cta gtc cac aga cct gct gca      816
Val Ile Thr Ala Leu Thr Leu Arg Cys Leu Val His Arg Pro Ala Ala
            260                 265                 270

agg tgg aga caa aga gaa atg ggg aga gcg cgg aaa tgg aaa aga tct      864
Arg Trp Arg Gln Arg Glu Met Gly Arg Ala Arg Lys Trp Lys Arg Ser
        275                 280                 285

cac ctg tct aca tagattctgc agaaccactg tatgcagagc atctggaggt          916
His Leu Ser Thr
    290

agcctcttta gctcttctct actag                                          941


<210> SEQ ID NO 2
<211> LENGTH: 292
<212> TYPE: PRT
<213> ORGANISM: feline CD80

<400> SEQUENCE: 2

Met Gly His Ala Ala Lys Trp Lys Thr Pro Leu Leu Lys His Pro Tyr
  1               5                  10                  15

Pro Lys Leu Phe Pro Leu Leu Met Leu Ala Ser Leu Phe Tyr Phe Cys
            20                  25                  30

Ser Gly Ile Ile Gln Val Asn Lys Thr Val Glu Glu Val Ala Val Leu
        35                  40                  45

Ser Cys Asp Tyr Asn Ile Ser Thr Lys Glu Leu Thr Glu Ile Arg Ile
    50                  55                  60

Tyr Trp Gln Lys Asp Asp Glu Met Val Leu Ala Val Met Ser Gly Lys
 65                  70                  75                  80

Val Gln Val Trp Pro Lys Tyr Lys Asn Arg Thr Phe Thr Asp Val Thr
                85                  90                  95

Asp Asn His Ser Ile Val Ile Met Ala Leu Arg Leu Ser Asp Asn Gly
            100                 105                 110

Lys Tyr Thr Cys Ile Ile Gln Lys Ile Glu Lys Gly Ser Tyr Lys Val
        115                 120                 125

Lys His Leu Thr Ser Val Met Leu Leu Val Arg Ala Asp Phe Pro Val
    130                 135                 140

Pro Ser Ile Thr Asp Leu Gly Asn Pro Ser His Asn Ile Lys Arg Ile
145                 150                 155                 160

Met Cys Leu Thr Ser Gly Gly Phe Pro Lys Pro His Leu Ser Trp Leu
                165                 170                 175

Glu Asn Glu Glu Glu Leu Asn Ala Ile Asn Thr Thr Val Ser Gln Asp
            180                 185                 190

Pro Glu Thr Glu Leu Tyr Thr Ile Ser Ser Glu Leu Asp Phe Asn Met
        195                 200                 205

Thr Asn Asn His Ser Phe Leu Cys Leu Val Lys Tyr Gly Asn Leu Leu
    210                 215                 220

Val Ser Gln Ile Phe Asn Trp Gln Lys Ser Glu Pro Gln Pro Ser Asn
225                 230                 235                 240

Asn Gln Leu Trp Ile Ile Ile Leu Ser Ser Val Val Ser Gly Ile Val
                245                 250                 255

Val Ile Thr Ala Leu Thr Leu Arg Cys Leu Val His Arg Pro Ala Ala
            260                 265                 270

Arg Trp Arg Gln Arg Glu Met Gly Arg Ala Arg Lys Trp Lys Arg Ser
        275                 280                 285

His Leu Ser Thr
    290
```

-continued

<210> SEQ ID NO 3
<211> LENGTH: 879
<212> TYPE: DNA
<213> ORGANISM: feline CD80
<220> FEATURE:
<221> NAME/KEY: CDS
<222> LOCATION: (1)..(876)

<400> SEQUENCE: 3

```
atg ggt cac gca gca aag tgg aaa aca cca cta ctg aag cac cca tat       48
Met Gly His Ala Ala Lys Trp Lys Thr Pro Leu Leu Lys His Pro Tyr
  1               5                  10                  15

ccc aag ctc ttt ccg ctc ttg atg cta gct agt ctt ttt tac ttc tgt       96
Pro Lys Leu Phe Pro Leu Leu Met Leu Ala Ser Leu Phe Tyr Phe Cys
             20                  25                  30

tca ggt atc atc cag gtg aac aag aca gtg gaa gaa gta gca gta cta      144
Ser Gly Ile Ile Gln Val Asn Lys Thr Val Glu Glu Val Ala Val Leu
         35                  40                  45

tcc tgt gat tac aac att tcc acc aaa gaa ctg acg gaa att cga atc      192
Ser Cys Asp Tyr Asn Ile Ser Thr Lys Glu Leu Thr Glu Ile Arg Ile
     50                  55                  60

tat tgg caa aag gat gat gaa atg gtg ttg gct gtc atg tct ggc aaa      240
Tyr Trp Gln Lys Asp Asp Glu Met Val Leu Ala Val Met Ser Gly Lys
 65                  70                  75                  80

gta caa gtg tgg ccc aag tac aag aac cgc aca ttc act gac gtc acc      288
Val Gln Val Trp Pro Lys Tyr Lys Asn Arg Thr Phe Thr Asp Val Thr
                 85                  90                  95

gat aac cac tcc att gtg atc atg gct ctg cgc ctg tca gac aat ggc      336
Asp Asn His Ser Ile Val Ile Met Ala Leu Arg Leu Ser Asp Asn Gly
            100                 105                 110

aaa tac act tgt atc att caa aag att caa aaa ggg tct tac aaa gtg      384
Lys Tyr Thr Cys Ile Ile Gln Lys Ile Gln Lys Gly Ser Tyr Lys Val
        115                 120                 125

aaa cac ctg act tcg gtg atg tta ttg gtc aga gct gac ttc cct gtc      432
Lys His Leu Thr Ser Val Met Leu Leu Val Arg Ala Asp Phe Pro Val
    130                 135                 140

cct agt ata act gat ctt gga aat cca tct cat aac atc aaa agg ata      480
Pro Ser Ile Thr Asp Leu Gly Asn Pro Ser His Asn Ile Lys Arg Ile
145                 150                 155                 160

atg tgc tta act tct gga ggt ttt cca aag cct cac ctc tcc tgg ctg      528
Met Cys Leu Thr Ser Gly Gly Phe Pro Lys Pro His Leu Ser Trp Leu
                165                 170                 175

gaa aat gaa gaa gaa tta aat gcc atc aac aca aca gtt tcc caa gat      576
Glu Asn Glu Glu Glu Leu Asn Ala Ile Asn Thr Thr Val Ser Gln Asp
            180                 185                 190

cct gaa act gag ctc tac act att agc agt gaa ctg gat ttc aat atg      624
Pro Glu Thr Glu Leu Tyr Thr Ile Ser Ser Glu Leu Asp Phe Asn Met
        195                 200                 205

aca aac aac cat agc ttc ctg tgt ctt gtc aag tat gga aac tta ata      672
Thr Asn Asn His Ser Phe Leu Cys Leu Val Lys Tyr Gly Asn Leu Ile
    210                 215                 220

gta tca cag atc ttc aac tgg caa aaa tca gag cca cag cct tct aat      720
Val Ser Gln Ile Phe Asn Trp Gln Lys Ser Glu Pro Gln Pro Ser Asn
225                 230                 235                 240

aat cag ctc tgg atc att atc ctg agc tca gta gta agt ggg att gtt      768
Asn Gln Leu Trp Ile Ile Ile Leu Ser Ser Val Val Ser Gly Ile Val
                245                 250                 255

gtg atc act gca ctt acc tta aga tgc cta gtc cac aga cct gct gca      816
Val Ile Thr Ala Leu Thr Leu Arg Cys Leu Val His Arg Pro Ala Ala
            260                 265                 270
```

-continued

```
agg tgg aga caa aga gaa atg ggg aga gcg cgg aaa tgg aaa aga tct      864
Arg Trp Arg Gln Arg Glu Met Gly Arg Ala Arg Lys Trp Lys Arg Ser
        275                 280                 285

cac ctg tct aca tag                                                  879
His Leu Ser Thr
    290


<210> SEQ ID NO 4
<211> LENGTH: 292
<212> TYPE: PRT
<213> ORGANISM: feline CD80

<400> SEQUENCE: 4

Met Gly His Ala Ala Lys Trp Lys Thr Pro Leu Leu Lys His Pro Tyr
  1               5                  10                  15

Pro Lys Leu Phe Pro Leu Leu Met Leu Ala Ser Leu Phe Tyr Phe Cys
             20                  25                  30

Ser Gly Ile Ile Gln Val Asn Lys Thr Val Glu Glu Val Ala Val Leu
        35                  40                  45

Ser Cys Asp Tyr Asn Ile Ser Thr Lys Glu Leu Thr Glu Ile Arg Ile
     50                  55                  60

Tyr Trp Gln Lys Asp Asp Glu Met Val Leu Ala Val Met Ser Gly Lys
 65                  70                  75                  80

Val Gln Val Trp Pro Lys Tyr Lys Asn Arg Thr Phe Thr Asp Val Thr
                 85                  90                  95

Asp Asn His Ser Ile Val Ile Met Ala Leu Arg Leu Ser Asp Asn Gly
            100                 105                 110

Lys Tyr Thr Cys Ile Ile Gln Lys Ile Gln Lys Gly Ser Tyr Lys Val
        115                 120                 125

Lys His Leu Thr Ser Val Met Leu Leu Val Arg Ala Asp Phe Pro Val
    130                 135                 140

Pro Ser Ile Thr Asp Leu Gly Asn Pro Ser His Asn Ile Lys Arg Ile
145                 150                 155                 160

Met Cys Leu Thr Ser Gly Gly Phe Pro Lys Pro His Leu Ser Trp Leu
                165                 170                 175

Glu Asn Glu Glu Glu Leu Asn Ala Ile Asn Thr Thr Val Ser Gln Asp
            180                 185                 190

Pro Glu Thr Glu Leu Tyr Thr Ile Ser Ser Glu Leu Asp Phe Asn Met
        195                 200                 205

Thr Asn Asn His Ser Phe Leu Cys Leu Val Lys Tyr Gly Asn Leu Ile
    210                 215                 220

Val Ser Gln Ile Phe Asn Trp Gln Lys Ser Glu Pro Gln Pro Ser Asn
225                 230                 235                 240

Asn Gln Leu Trp Ile Ile Ile Leu Ser Ser Val Val Ser Gly Ile Val
                245                 250                 255

Val Ile Thr Ala Leu Thr Leu Arg Cys Leu Val His Arg Pro Ala Ala
            260                 265                 270

Arg Trp Arg Gln Arg Glu Met Gly Arg Ala Arg Lys Trp Lys Arg Ser
        275                 280                 285

His Leu Ser Thr
    290


<210> SEQ ID NO 5
<211> LENGTH: 1080
<212> TYPE: DNA
<213> ORGANISM: feline CD86
<220> FEATURE:
```

-continued

```
<221> NAME/KEY: CDS
<222> LOCATION: (63)..(1052)

<400> SEQUENCE: 5

gtttctgtgt tcctcgggaa tgtcactgag cttatacatc tggtctctgg gagctgcagt      60

gg atg ggc att tgt gac agc act atg gga ctg agt cac act ctc ctt        107
   Met Gly Ile Cys Asp Ser Thr Met Gly Leu Ser His Thr Leu Leu
     1               5                  10                  15

gtg atg gcc ctc ctg ctc tct ggt gtt tct tcc atg aag agt caa gca       155
Val Met Ala Leu Leu Leu Ser Gly Val Ser Ser Met Lys Ser Gln Ala
                20                  25                  30

tat ttc aac aag act gga gaa ctg cca tgc cat ttt aca aac tct caa       203
Tyr Phe Asn Lys Thr Gly Glu Leu Pro Cys His Phe Thr Asn Ser Gln
            35                  40                  45

aac ata agc ctg gat gag ctg gta gta ttt tgg cag gac cag gat aag       251
Asn Ile Ser Leu Asp Glu Leu Val Val Phe Trp Gln Asp Gln Asp Lys
        50                  55                  60

ctg gtt ctg tat gag ata ttc aga ggc aaa gag aac cct caa aat gtt       299
Leu Val Leu Tyr Glu Ile Phe Arg Gly Lys Glu Asn Pro Gln Asn Val
    65                  70                  75

cat ctc aaa tat aag ggc cgt aca agc ttt gac aag gac aac tgg acc       347
His Leu Lys Tyr Lys Gly Arg Thr Ser Phe Asp Lys Asp Asn Trp Thr
 80                  85                  90                  95

ctg aga ctc cac aat gtt cag atc aag gac aag ggc aca tat cac tgt       395
Leu Arg Leu His Asn Val Gln Ile Lys Asp Lys Gly Thr Tyr His Cys
                100                 105                 110

ttc att cat tat aaa ggg ccc aaa gga cta gtt ccc atg cac caa atg       443
Phe Ile His Tyr Lys Gly Pro Lys Gly Leu Val Pro Met His Gln Met
            115                 120                 125

agt tct gac cta tca gtg ctt gct aac ttc agt caa cct gaa ata aca       491
Ser Ser Asp Leu Ser Val Leu Ala Asn Phe Ser Gln Pro Glu Ile Thr
        130                 135                 140

gta act tct aat aga aca gaa aat tct ggc atc ata aat ttg acc tgc       539
Val Thr Ser Asn Arg Thr Glu Asn Ser Gly Ile Ile Asn Leu Thr Cys
    145                 150                 155

tca tct ata caa ggt tac cca gaa cct aag gag atg tat ttt cag cta       587
Ser Ser Ile Gln Gly Tyr Pro Glu Pro Lys Glu Met Tyr Phe Gln Leu
160                 165                 170                 175

aac act gag aat tca act act aag tat gat act gtc atg aag aaa tct       635
Asn Thr Glu Asn Ser Thr Thr Lys Tyr Asp Thr Val Met Lys Lys Ser
                180                 185                 190

caa aat aat gtg aca gaa ctg tac aac gtt tct atc agc ttg cct ttt       683
Gln Asn Asn Val Thr Glu Leu Tyr Asn Val Ser Ile Ser Leu Pro Phe
            195                 200                 205

tca gtc cct gaa gca cac aat gtg agc gtc ttt tgt gcc ctg aaa ctg       731
Ser Val Pro Glu Ala His Asn Val Ser Val Phe Cys Ala Leu Lys Leu
        210                 215                 220

gag aca ctg gag atg ctg ctc tcc cta cct ttc aat ata gat gca caa       779
Glu Thr Leu Glu Met Leu Leu Ser Leu Pro Phe Asn Ile Asp Ala Gln
    225                 230                 235

cct aag gat aaa gac cct gaa caa ggc cac ttc ctc tgg att gcg gct       827
Pro Lys Asp Lys Asp Pro Glu Gln Gly His Phe Leu Trp Ile Ala Ala
240                 245                 250                 255

gta ctt gta atg ttt gtt gtt ttt tgt ggg atg gtg tcc ttt aaa aca       875
Val Leu Val Met Phe Val Val Phe Cys Gly Met Val Ser Phe Lys Thr
                260                 265                 270

cta agg aaa agg aag aag aag cag cct ggc ccc tct cat gaa tgt gaa       923
Leu Arg Lys Arg Lys Lys Lys Gln Pro Gly Pro Ser His Glu Cys Glu
            275                 280                 285
```

-continued

```
acc atc aaa agg gag aga aaa gag agc aaa cag acc aac gaa aga gta      971
Thr Ile Lys Arg Glu Arg Lys Glu Ser Lys Gln Thr Asn Glu Arg Val
        290                 295                 300

cca tac cac gta cct gag aga tct gat gaa gcc cag tgt gtt aac att     1019
Pro Tyr His Val Pro Glu Arg Ser Asp Glu Ala Gln Cys Val Asn Ile
    305                 310                 315

ttg aag aca gcc tca ggg gac aaa aat cag tag gaaaatggtg gcttggcgtg   1072
Leu Lys Thr Ala Ser Gly Asp Lys Asn Gln
320                 325                 330

ctgacaat                                                            1080


<210> SEQ ID NO 6
<211> LENGTH: 329
<212> TYPE: PRT
<213> ORGANISM: feline CD86

<400> SEQUENCE: 6

Met Gly Ile Cys Asp Ser Thr Met Gly Leu Ser His Thr Leu Leu Val
  1               5                  10                  15

Met Ala Leu Leu Leu Ser Gly Val Ser Ser Met Lys Ser Gln Ala Tyr
             20                  25                  30

Phe Asn Lys Thr Gly Glu Leu Pro Cys His Phe Thr Asn Ser Gln Asn
         35                  40                  45

Ile Ser Leu Asp Glu Leu Val Val Phe Trp Gln Asp Gln Asp Lys Leu
     50                  55                  60

Val Leu Tyr Glu Ile Phe Arg Gly Lys Glu Asn Pro Gln Asn Val His
 65                  70                  75                  80

Leu Lys Tyr Lys Gly Arg Thr Ser Phe Asp Lys Asp Asn Trp Thr Leu
                 85                  90                  95

Arg Leu His Asn Val Gln Ile Lys Asp Lys Gly Thr Tyr His Cys Phe
            100                 105                 110

Ile His Tyr Lys Gly Pro Lys Gly Leu Val Pro Met His Gln Met Ser
        115                 120                 125

Ser Asp Leu Ser Val Leu Ala Asn Phe Ser Gln Pro Glu Ile Thr Val
    130                 135                 140

Thr Ser Asn Arg Thr Glu Asn Ser Gly Ile Ile Asn Leu Thr Cys Ser
145                 150                 155                 160

Ser Ile Gln Gly Tyr Pro Glu Pro Lys Glu Met Tyr Phe Gln Leu Asn
                165                 170                 175

Thr Glu Asn Ser Thr Thr Lys Tyr Asp Thr Val Met Lys Lys Ser Gln
            180                 185                 190

Asn Asn Val Thr Glu Leu Tyr Asn Val Ser Ile Ser Leu Pro Phe Ser
        195                 200                 205

Val Pro Glu Ala His Asn Val Ser Val Phe Cys Ala Leu Lys Leu Glu
    210                 215                 220

Thr Leu Glu Met Leu Leu Ser Leu Pro Phe Asn Ile Asp Ala Gln Pro
225                 230                 235                 240

Lys Asp Lys Asp Pro Glu Gln Gly His Phe Leu Trp Ile Ala Ala Val
                245                 250                 255

Leu Val Met Phe Val Val Phe Cys Gly Met Val Ser Phe Lys Thr Leu
            260                 265                 270

Arg Lys Arg Lys Lys Lys Gln Pro Gly Pro Ser His Glu Cys Glu Thr
        275                 280                 285

Ile Lys Arg Glu Arg Lys Glu Ser Lys Gln Thr Asn Glu Arg Val Pro
    290                 295                 300
```

-continued

```
Tyr His Val Pro Glu Arg Ser Asp Glu Ala Gln Cys Val Asn Ile Leu
305                 310                 315                 320

Lys Thr Ala Ser Gly Asp Lys Asn Gln
                325


<210> SEQ ID NO 7
<211> LENGTH: 688
<212> TYPE: DNA
<213> ORGANISM: feline CD28
<220> FEATURE:
<221> NAME/KEY: CDS
<222> LOCATION: (1)..(663)

<400> SEQUENCE: 7

atg atc ctc agg ctg ctt ctg gct ctc aac ttc ttc ccc tca att caa       48
Met Ile Leu Arg Leu Leu Leu Ala Leu Asn Phe Phe Pro Ser Ile Gln
  1               5                  10                  15

gta aca gaa aac aag att ttg gtg aag cag ttg ccc agg ctt gtg gtg       96
Val Thr Glu Asn Lys Ile Leu Val Lys Gln Leu Pro Arg Leu Val Val
             20                  25                  30

tac aac aat gag gtc aac ctt agc tgc aag tac act cac aac ttc ttc      144
Tyr Asn Asn Glu Val Asn Leu Ser Cys Lys Tyr Thr His Asn Phe Phe
         35                  40                  45

tca aag gag ttc cgg gca tcc ctt tat aag gga gta gat agt gct gtg      192
Ser Lys Glu Phe Arg Ala Ser Leu Tyr Lys Gly Val Asp Ser Ala Val
     50                  55                  60

gaa gtc tgc gtt gtg aat gga aat tac tcc cat cag cct cag ttc tac      240
Glu Val Cys Val Val Asn Gly Asn Tyr Ser His Gln Pro Gln Phe Tyr
 65                  70                  75                  80

tca agt aca gga ttc gac tgt gat ggg aaa ttg ggc aat gaa aca gtg      288
Ser Ser Thr Gly Phe Asp Cys Asp Gly Lys Leu Gly Asn Glu Thr Val
                 85                  90                  95

aca ttc tac ctc cga aat ttg ttt gtt aac caa acg gat att tac ttc      336
Thr Phe Tyr Leu Arg Asn Leu Phe Val Asn Gln Thr Asp Ile Tyr Phe
            100                 105                 110

tgc aaa att gaa gtc atg tat cca cct cct tac ata gac aat gag aag      384
Cys Lys Ile Glu Val Met Tyr Pro Pro Pro Tyr Ile Asp Asn Glu Lys
        115                 120                 125

agc aat ggg acc att atc cac gtg aaa gag aaa cat ctt tgt cca gct      432
Ser Asn Gly Thr Ile Ile His Val Lys Glu Lys His Leu Cys Pro Ala
    130                 135                 140

cag ctg tct cct gaa tct tcc aag cca ttt tgg gca ctg gtg gtg gtt      480
Gln Leu Ser Pro Glu Ser Ser Lys Pro Phe Trp Ala Leu Val Val Val
145                 150                 155                 160

ggt gga atc cta ggt ttc tac agc ttg cta gca aca gtg gct ctt ggt      528
Gly Gly Ile Leu Gly Phe Tyr Ser Leu Leu Ala Thr Val Ala Leu Gly
                165                 170                 175

gct tgc tgg atg aag acc aag agg agt agg atc ctt cag agt gac tat      576
Ala Cys Trp Met Lys Thr Lys Arg Ser Arg Ile Leu Gln Ser Asp Tyr
            180                 185                 190

atg aac atg acc ccc cgg agg cca ggg ccc acc cga agg cac tac caa      624
Met Asn Met Thr Pro Arg Arg Pro Gly Pro Thr Arg Arg His Tyr Gln
        195                 200                 205

cct tac gcc cca gca cgc gac ttt gcg gca tac cgt tcc tgacatggac      673
Pro Tyr Ala Pro Ala Arg Asp Phe Ala Ala Tyr Arg Ser
    210                 215                 220

ccctatccag aagcc                                                     688


<210> SEQ ID NO 8
<211> LENGTH: 221
<212> TYPE: PRT
```

-continued

```
<213> ORGANISM: feline CD28

<400> SEQUENCE: 8

Met Ile Leu Arg Leu Leu Leu Ala Leu Asn Phe Phe Pro Ser Ile Gln
  1               5                  10                  15

Val Thr Glu Asn Lys Ile Leu Val Lys Gln Leu Pro Arg Leu Val Val
             20                  25                  30

Tyr Asn Asn Glu Val Asn Leu Ser Cys Lys Tyr Thr His Asn Phe Phe
         35                  40                  45

Ser Lys Glu Phe Arg Ala Ser Leu Tyr Lys Gly Val Asp Ser Ala Val
     50                  55                  60

Glu Val Cys Val Val Asn Gly Asn Tyr Ser His Gln Pro Gln Phe Tyr
 65                  70                  75                  80

Ser Ser Thr Gly Phe Asp Cys Asp Gly Lys Leu Gly Asn Glu Thr Val
                 85                  90                  95

Thr Phe Tyr Leu Arg Asn Leu Phe Val Asn Gln Thr Asp Ile Tyr Phe
            100                 105                 110

Cys Lys Ile Glu Val Met Tyr Pro Pro Pro Tyr Ile Asp Asn Glu Lys
        115                 120                 125

Ser Asn Gly Thr Ile Ile His Val Lys Glu Lys His Leu Cys Pro Ala
    130                 135                 140

Gln Leu Ser Pro Glu Ser Ser Lys Pro Phe Trp Ala Leu Val Val Val
145                 150                 155                 160

Gly Gly Ile Leu Gly Phe Tyr Ser Leu Leu Ala Thr Val Ala Leu Gly
                165                 170                 175

Ala Cys Trp Met Lys Thr Lys Arg Ser Arg Ile Leu Gln Ser Asp Tyr
            180                 185                 190

Met Asn Met Thr Pro Arg Arg Pro Gly Pro Thr Arg Arg His Tyr Gln
        195                 200                 205

Pro Tyr Ala Pro Ala Arg Asp Phe Ala Ala Tyr Arg Ser
    210                 215                 220


<210> SEQ ID NO 9
<211> LENGTH: 749
<212> TYPE: DNA
<213> ORGANISM: feline CTLA-4
<220> FEATURE:
<221> NAME/KEY: CDS
<222> LOCATION: (27)..(698)

<400> SEQUENCE: 9

aacctgaaca ctgctcccat aaagcc atg gct tgc ttt gga ttc cgg agg cat      53
                             Met Ala Cys Phe Gly Phe Arg Arg His
                               1               5

ggg gct cag ctg gac ctg gct tct agg acc tgg ccc tgc act gct ctg      101
Gly Ala Gln Leu Asp Leu Ala Ser Arg Thr Trp Pro Cys Thr Ala Leu
 10                  15                  20                  25

ttt tct ctt ctc ttt atc ccc gtc ttc tcc aaa ggg atg cat gtg gcc      149
Phe Ser Leu Leu Phe Ile Pro Val Phe Ser Lys Gly Met His Val Ala
                 30                  35                  40

cac cct gca gtg gtg ctg gcc agc agc cga ggt gtc gcc agc ttc gtg      197
His Pro Ala Val Val Leu Ala Ser Ser Arg Gly Val Ala Ser Phe Val
             45                  50                  55

tgt gaa tat ggg tct tca ggc aat gcc gcc aaa ttc cga gtg act gtg      245
Cys Glu Tyr Gly Ser Ser Gly Asn Ala Ala Lys Phe Arg Val Thr Val
         60                  65                  70

ctg agg caa act ggc agc caa atg act gaa gtc tgt gct gcg aca tac      293
Leu Arg Gln Thr Gly Ser Gln Met Thr Glu Val Cys Ala Ala Thr Tyr
```

```
     75                  80                  85

aca gtg gag aat gag ttg gcc ttc cta aat gat tcc acc tgc act ggc      341
Thr Val Glu Asn Glu Leu Ala Phe Leu Asn Asp Ser Thr Cys Thr Gly
 90                  95                 100                 105

atc tcc agc gga aac aaa gtg aac ctc acc atc caa ggg ttg agg gcc      389
Ile Ser Ser Gly Asn Lys Val Asn Leu Thr Ile Gln Gly Leu Arg Ala
                110                 115                 120

atg gac acg gga ctc tac atc tgc aag gtg gag ctc atg tac cca cca      437
Met Asp Thr Gly Leu Tyr Ile Cys Lys Val Glu Leu Met Tyr Pro Pro
            125                 130                 135

ccc tac tat gca ggc atg ggc aat gga acc cag att tat gtc atc gat      485
Pro Tyr Tyr Ala Gly Met Gly Asn Gly Thr Gln Ile Tyr Val Ile Asp
        140                 145                 150

cct gaa cct tgc cca gat tct gac ttc ctc ctc tgg atc ctc gca gca      533
Pro Glu Pro Cys Pro Asp Ser Asp Phe Leu Leu Trp Ile Leu Ala Ala
    155                 160                 165

gtc agt tca gga ttg ttt ttt tat agc ttc ctt atc aca gct gtt tct      581
Val Ser Ser Gly Leu Phe Phe Tyr Ser Phe Leu Ile Thr Ala Val Ser
170                 175                 180                 185

ttg agc aaa atg cta aag aaa aga agc cct ctt act aca ggg gtc tat      629
Leu Ser Lys Met Leu Lys Lys Arg Ser Pro Leu Thr Thr Gly Val Tyr
                190                 195                 200

gtg aaa atg ccc cca aca gag cca gaa tgt gaa aag caa ttt cag cct      677
Val Lys Met Pro Pro Thr Glu Pro Glu Cys Glu Lys Gln Phe Gln Pro
            205                 210                 215

tat ttt att ccc atc aat tga cacaccgtta tgaagaagga agaacactgt         728
Tyr Phe Ile Pro Ile Asn
        220

ccaatttcta agagctgagg c                                              749


<210> SEQ ID NO 10
<211> LENGTH: 223
<212> TYPE: PRT
<213> ORGANISM: feline CTLA-4

<400> SEQUENCE: 10

Met Ala Cys Phe Gly Phe Arg Arg His Gly Ala Gln Leu Asp Leu Ala
  1               5                  10                  15

Ser Arg Thr Trp Pro Cys Thr Ala Leu Phe Ser Leu Leu Phe Ile Pro
            20                  25                  30

Val Phe Ser Lys Gly Met His Val Ala His Pro Ala Val Val Leu Ala
        35                  40                  45

Ser Ser Arg Gly Val Ala Ser Phe Val Cys Glu Tyr Gly Ser Ser Gly
    50                  55                  60

Asn Ala Ala Lys Phe Arg Val Thr Val Leu Arg Gln Thr Gly Ser Gln
 65                  70                  75                  80

Met Thr Glu Val Cys Ala Ala Thr Tyr Thr Val Glu Asn Glu Leu Ala
                85                  90                  95

Phe Leu Asn Asp Ser Thr Cys Thr Gly Ile Ser Ser Gly Asn Lys Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Ala Gly Met Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
```

-continued

```
                165                 170                 175

Tyr Ser Phe Leu Ile Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220


<210> SEQ ID NO 11
<211> LENGTH: 40
<212> TYPE: DNA
<213> ORGANISM: feline CD80 primer

<400> SEQUENCE: 11

cgcggatccg caccatgggt cacgcagcaa agtggaaaac                           40


<210> SEQ ID NO 12
<211> LENGTH: 25
<212> TYPE: DNA
<213> ORGANISM: feline CD80 primer

<400> SEQUENCE: 12

cctagtagag aagagctaaa gaggc                                           25


<210> SEQ ID NO 13
<211> LENGTH: 33
<212> TYPE: DNA
<213> ORGANISM: feline CD28 primer

<400> SEQUENCE: 13

cgcggatcca ccggtagcac aatgatcctc agg                                  33


<210> SEQ ID NO 14
<211> LENGTH: 31
<212> TYPE: DNA
<213> ORGANISM: feline CD28 primer

<400> SEQUENCE: 14

cgcggatcct ctggataggg gtccatgtca g                                    31


<210> SEQ ID NO 15
<211> LENGTH: 27
<212> TYPE: DNA
<213> ORGANISM: feline CTLA-4 primer

<400> SEQUENCE: 15

atggcttcgc cttggatttc cagcagg                                         27


<210> SEQ ID NO 16
<211> LENGTH: 29
<212> TYPE: DNA
<213> ORGANISM: feline CTLA-4 primer

<400> SEQUENCE: 16

tcaattgaat gaggaataaa ataaggctg                                       29


<210> SEQ ID NO 17
<211> LENGTH: 28
<212> TYPE: DNA
<213> ORGANISM: feline CTLA-4 primer

<400> SEQUENCE: 17
```

-continued tgttgggttt ctgactctga cttccctg 28

<210> SEQ ID NO 18
<211> LENGTH: 24
<212> TYPE: DNA
<213> ORGANISM: feline CTLA-4 primer

<400> SEQUENCE: 18
gcatagtagg gtggtgggta catg 24

<210> SEQ ID NO 19
<211> LENGTH: 28
<212> TYPE: DNA
<213> ORGANISM: feline CTLA-4 primer

<400> SEQUENCE: 19
tgttgggttt ctgactctga cttccctg 28

<210> SEQ ID NO 20
<211> LENGTH: 20
<212> TYPE: DNA
<213> ORGANISM: feline CTLA-4 primer

<400> SEQUENCE: 20
acatgagctc caccttgcag 20

<210> SEQ ID NO 21
<211> LENGTH: 27
<212> TYPE: DNA
<213> ORGANISM: feline CTLA-4 primer

<400> SEQUENCE: 21
ccatcctaat acgactcact atagggc 27

<210> SEQ ID NO 22
<211> LENGTH: 24
<212> TYPE: DNA
<213> ORGANISM: feline CTLA-4 primer

<400> SEQUENCE: 22
gtgaatatgg gtcttcaggc aatg 24

<210> SEQ ID NO 23
<211> LENGTH: 23
<212> TYPE: DNA
<213> ORGANISM: feline CTLA-4 primer

<400> SEQUENCE: 23
actcactata gggctcgagc ggc 23

<210> SEQ ID NO 24
<211> LENGTH: 23
<212> TYPE: DNA
<213> ORGANISM: feline CTLA-4 primer

<400> SEQUENCE: 24
gaaatccgag tgactgtgct gag 23

<210> SEQ ID NO 25
<211> LENGTH: 24
<212> TYPE: DNA
<213> ORGANISM: feline CTLA-4 primer

<400> SEQUENCE: 25

-continued aacctgaaca ctgctcccat aaag 24

<210> SEQ ID NO 26
<211> LENGTH: 25
<212> TYPE: DNA
<213> ORGANISM: feline CTLA-4 primer

<400> SEQUENCE: 26
gcctcagctc ttagaaattg gacag 25

<210> SEQ ID NO 27
<211> LENGTH: 21
<212> TYPE: DNA
<213> ORGANISM: feline CD86 primer

<400> SEQUENCE: 27
tagtattttg gcaggaccag g 21

<210> SEQ ID NO 28
<211> LENGTH: 23
<212> TYPE: DNA
<213> ORGANISM: feline CD86 primer

<400> SEQUENCE: 28
ctgtgacatt atcttgagat ttc 23

<210> SEQ ID NO 29
<211> LENGTH: 23
<212> TYPE: DNA
<213> ORGANISM: feline CD86 primer

<400> SEQUENCE: 29
gagcatgcac taatgggact gag 23

<210> SEQ ID NO 30
<211> LENGTH: 23
<212> TYPE: DNA
<213> ORGANISM: feline CD86 primer

<400> SEQUENCE: 30
ctgtgacatt atcttgagat ttc 23

<210> SEQ ID NO 31
<211> LENGTH: 27
<212> TYPE: DNA
<213> ORGANISM: feline CD86 primer

<400> SEQUENCE: 31
ccatcctaat acgactcact atagggc 27

<210> SEQ ID NO 32
<211> LENGTH: 28
<212> TYPE: DNA
<213> ORGANISM: feline CD86 primer

<400> SEQUENCE: 32
tgggtaacct tgtatagatg agcaggtc 28

<210> SEQ ID NO 33
<211> LENGTH: 23
<212> TYPE: DNA
<213> ORGANISM: feline CD86 primer -continued

<400> SEQUENCE: 33
actcactata gggctcgagc ggc 23

<210> SEQ ID NO 34
<211> LENGTH: 25
<212> TYPE: DNA
<213> ORGANISM: feline CD86 primer

<400> SEQUENCE: 34
caggttgact gaagttagca agcac 25

<210> SEQ ID NO 35
<211> LENGTH: 27
<212> TYPE: DNA
<213> ORGANISM: feline CD86 primer

<400> SEQUENCE: 35
ccatcctaat acgactcact atagggc 27

<210> SEQ ID NO 36
<211> LENGTH: 25
<212> TYPE: DNA
<213> ORGANISM: feline CD86 primer

<400> SEQUENCE: 36
ggacaagggc acatatcact gtttc 25

<210> SEQ ID NO 37
<211> LENGTH: 23
<212> TYPE: DNA
<213> ORGANISM: feline CD86 primer

<400> SEQUENCE: 37
actcactata gggctcgagc ggc 23

<210> SEQ ID NO 38
<211> LENGTH: 25
<212> TYPE: DNA
<213> ORGANISM: feline CD86 primer

<400> SEQUENCE: 38
cagtgcttgc taacttcagt caacc 25

<210> SEQ ID NO 39
<211> LENGTH: 23
<212> TYPE: DNA
<213> ORGANISM: feline CD86 primer

<400> SEQUENCE: 39
cgggaatgtc actgagctta tag 23

<210> SEQ ID NO 40
<211> LENGTH: 23
<212> TYPE: DNA
<213> ORGANISM: feline CD86 primer

<400> SEQUENCE: 40
gatctttttc aggttagcag ggg 23

<210> SEQ ID NO 41
<211> LENGTH: 20
<212> TYPE: DNA
<213> ORGANISM: feline CD80 primer

<400> SEQUENCE: 41
atgggtcacg cagcaaagtg 20

<210> SEQ ID NO 42
<211> LENGTH: 20
<212> TYPE: DNA
<213> ORGANISM: feline CD80 primer

<400> SEQUENCE: 42
ctatgtagac aggtgagatc 20

<210> SEQ ID NO 43
<211> LENGTH: 17
<212> TYPE: DNA
<213> ORGANISM: feline CD80 primer

<400> SEQUENCE: 43
caggaaacag ctatgac 17

<210> SEQ ID NO 44
<211> LENGTH: 18
<212> TYPE: DNA
<213> ORGANISM: feline CD80 primer

<400> SEQUENCE: 44
aatacgactc actatagg 18

<210> SEQ ID NO 45
<211> LENGTH: 21
<212> TYPE: DNA
<213> ORGANISM: feline CD80 primer

<400> SEQUENCE: 45
aacaccattt catcatcctt t 21

<210> SEQ ID NO 46
<211> LENGTH: 23
<212> TYPE: DNA
<213> ORGANISM: feline CD80 primer

<400> SEQUENCE: 46
atacaagtgt atttgccatt gtc 23

<210> SEQ ID NO 47
<211> LENGTH: 20
<212> TYPE: DNA
<213> ORGANISM: feline CD80 primer

<400> SEQUENCE: 47
agctctgacc aataacatca 20

<210> SEQ ID NO 48
<211> LENGTH: 22
<212> TYPE: DNA
<213> ORGANISM: feline CD80 primer

<400> SEQUENCE: 48
attagaaatc cagttcactg ct 22

<210> SEQ ID NO 49
<211> LENGTH: 21
<212> TYPE: DNA

-continued

<213> ORGANISM: feline CD80 primer

<400> SEQUENCE: 49
tcatgtctgg caaagtacaa g 21

<210> SEQ ID NO 50
<211> LENGTH: 18
<212> TYPE: DNA
<213> ORGANISM: feline CD80 primer

<400> SEQUENCE: 50
attcactgac gtcaccga 18

<210> SEQ ID NO 51
<211> LENGTH: 16
<212> TYPE: DNA
<213> ORGANISM: feline CD80 primer

<400> SEQUENCE: 51
aaggctgtgg ctctga 16

<210> SEQ ID NO 52
<211> LENGTH: 29
<212> TYPE: DNA
<213> ORGANISM: feline CD80 primer

<400> SEQUENCE: 52
tcgagaattc gggtcacgca gcaaagtgg 29

<210> SEQ ID NO 53
<211> LENGTH: 32
<212> TYPE: DNA
<213> ORGANISM: feline CD80 primer

<400> SEQUENCE: 53
gctaggatcc aatctatgta gacaggtgag at 32

<210> SEQ ID NO 54
<211> LENGTH: 32
<212> TYPE: DNA
<213> ORGANISM: feline CD80 primer

<400> SEQUENCE: 54
gatgaattcc atgatcctca ggctgggctt ct 32

<210> SEQ ID NO 55
<211> LENGTH: 29
<212> TYPE: DNA
<213> ORGANISM: feline CD80 primer

<400> SEQUENCE: 55
gatcagatct caggaacggt atgccgcaa 29

<210> SEQ ID NO 56
<211> LENGTH: 22
<212> TYPE: DNA
<213> ORGANISM: B7-2 primer

<400> SEQUENCE: 56
ggcccgagta kaagaaccgg ac 22

<210> SEQ ID NO 57
<211> LENGTH: 24

-continued

<212> TYPE: DNA
<213> ORGANISM: B7-3 primer

<400> SEQUENCE: 57
cagwttcagg atcytgggaa aytg 24

<210> SEQ ID NO 58
<211> LENGTH: 20
<212> TYPE: DNA
<213> ORGANISM: B7-284 primer

<400> SEQUENCE: 58
ttatactagg gacagggaag 20

<210> SEQ ID NO 59
<211> LENGTH: 20
<212> TYPE: DNA
<213> ORGANISM: B7-190 primer

<400> SEQUENCE: 59
aggctttgga aaacctccag 20

<210> SEQ ID NO 60
<211> LENGTH: 21
<212> TYPE: DNA
<213> ORGANISM: B7-20 primer

<400> SEQUENCE: 60
ttgttatcgg tgacgtcagt g 21

<210> SEQ ID NO 61
<211> LENGTH: 22
<212> TYPE: DNA
<213> ORGANISM: B7-135 primer

<400> SEQUENCE: 61
caataacatc accgaagtca gg 22

<210> SEQ ID NO 62
<211> LENGTH: 22
<212> TYPE: DNA
<213> ORGANISM: B7-s220 primer

<400> SEQUENCE: 62
gtcatgtctg gcaaagtaca ag 22

<210> SEQ ID NO 63
<211> LENGTH: 22
<212> TYPE: DNA
<213> ORGANISM: B7-50 primer

<400> SEQUENCE: 63
cactgacgtc accgataacc ac 22

<210> SEQ ID NO 64
<211> LENGTH: 22
<212> TYPE: DNA
<213> ORGANISM: B7-140 primer

<400> SEQUENCE: 64
ctgacttcgg tgatgttatt gg 22

<210> SEQ ID NO 65

-continued

<211> LENGTH: 21
<212> TYPE: DNA
<213> ORGANISM: B7-550 primer

<400> SEQUENCE: 65
gccatcaaca caacagtttc c 21

<210> SEQ ID NO 66
<211> LENGTH: 22
<212> TYPE: DNA
<213> ORGANISM: B7-620 primer

<400> SEQUENCE: 66
tatgacaaac aaccatagct tc 22

<210> SEQ ID NO 67
<211> LENGTH: 20
<212> TYPE: DNA
<213> ORGANISM: B7-1281 primer

<400> SEQUENCE: 67
graagawtgc ctcatgakcc 20

<210> SEQ ID NO 68
<211> LENGTH: 17
<212> TYPE: DNA
<213> ORGANISM: B7-1260 primer

<400> SEQUENCE: 68
cayratccaa cataggg 17

<210> SEQ ID NO 69
<211> LENGTH: 21
<212> TYPE: DNA
<213> ORGANISM: B7 start primer

<400> SEQUENCE: 69
atgggtcacg cagcaaagtg g 21

<210> SEQ ID NO 70
<211> LENGTH: 25
<212> TYPE: DNA
<213> ORGANISM: B7-960 primer

<400> SEQUENCE: 70
cctagtagag aagagctaaa gaggc 25

<210> SEQ ID NO 71
<211> LENGTH: 21
<212> TYPE: DNA
<213> ORGANISM: CD28-113 primer

<400> SEQUENCE: 71
caaccttagc tgcaagtaca c 21

<210> SEQ ID NO 72
<211> LENGTH: 20
<212> TYPE: DNA
<213> ORGANISM: CD28-768 primer

<400> SEQUENCE: 72
ggcttctgga tagggatagg 20

-continued

<210> SEQ ID NO 73
<211> LENGTH: 22
<212> TYPE: DNA
<213> ORGANISM: CD28-190 primer

<400> SEQUENCE: 73
cggaggtaga attgcactgt cc 22

<210> SEQ ID NO 74
<211> LENGTH: 21
<212> TYPE: DNA
<213> ORGANISM: CD28-239 primer

<400> SEQUENCE: 74
attttgcaga agtaaatatc c 21

<210> SEQ ID NO 75
<211> LENGTH: 33
<212> TYPE: DNA
<213> ORGANISM: feCD28 primer

<400> SEQUENCE: 75
cgcggatcca ccggtagcac aatgatcctc agg 33

<210> SEQ ID NO 76
<211> LENGTH: 31
<212> TYPE: DNA
<213> ORGANISM: feCD28 primer

<400> SEQUENCE: 76
cgcggatcct ctggatagcc ctccatgtca g 31

<210> SEQ ID NO 77
<211> LENGTH: 31
<212> TYPE: DNA
<213> ORGANISM: FIV PPR upstream primer

<400> SEQUENCE: 77
gcccggatcc tatggcagaa gggtttgcag c 31

<210> SEQ ID NO 78
<211> LENGTH: 31
<212> TYPE: DNA
<213> ORGANISM: FIV PPR downstream primer

<400> SEQUENCE: 78
ccgtggatcc ggcactccat cattcctcct c 31

<210> SEQ ID NO 79
<211> LENGTH: 32
<212> TYPE: DNA
<213> ORGANISM: FIV PPR upstream primer

<400> SEQUENCE: 79
gcgtgaattc ggggaatgga caggggcgag at 32

<210> SEQ ID NO 80
<211> LENGTH: 28
<212> TYPE: DNA
<213> ORGANISM: FIV PPR downstream primer

<400> SEQUENCE: 80
gagccagatc tgctcttttt actttccc 28

-continued

```
<210> SEQ ID NO 81
<211> LENGTH: 36
<212> TYPE: DNA
<213> ORGANISM: IFN primer

<400> SEQUENCE: 81

tcgagaattc gatgaattac acaagtttta ttttcg                              36


<210> SEQ ID NO 82
<211> LENGTH: 33
<212> TYPE: DNA
<213> ORGANISM: IFN primer

<400> SEQUENCE: 82

tcgaggatcc ttatttcgat gctctacggc ctc                                 33
```

RECOMBINANT VIRUS EXPRESSING FOREIGN DNA ENCODING FELINE CD86 AND USES THEREOF

This application claims the benefit of U.S. Provisional Application No. 60/083,870, filed May 1, 1998, now expired, the content of which is hereby incorporated into this application by reference. Throughout this application various publication are referenced in parentheses. Full citations for these publications may be found at the end of the specification immediately preceding the sequence listing section. The disclosures of these publications are in their entirety hereby incorporated by reference into this application to more fully describe the state of the art to which this invention pertains.

BACKGROUND OF THE INVENTION

The stimulation of T-cell activation and proliferation in response to disease in the host is believed to be dependent on two interactions: the recognition of the T-cell receptor (TCR) with immunogenic peptides in the context of the MHC class I molecules and the secondary interaction of accessory ligands, such as CD80 and CD86, with their coreceptors, CD-28 and/or CTLA-4 on the T-cell. The successful interaction of these two pathways leads to activation and proliferation of both CD4+ and CD8+ T-cells and the increased production of Th1 and Th2 type immune regulating cytokines. In the absence of adequate co-stimulation of T-cells, an anergic state may develop, whereby T cells fail to proliferate and secrete cytokines. Over the years, two molecules have emerged as key regulators of T cell responses, CD28 and its ligands, CD80 and CD86. CD28 is the primary T-cell co-stimulatory receptor and upon interaction with CD80 and CD86, it enhances T-cell proliferation and cytokine synthesis, preventing T-cell death. CTLA-4 (also called CD152), a CD-28 homologue, also plays an important role in co-stimulation. Although, not completely understood, it appears to inhibit T-cell costimulatory responses. The interaction and interplay among CD28, CTLA-4 and their ligands CD80 and CD86 in co-stimulatory processes is key to the overall induction and suppression of immune responses to disease in the host. (Linsley et al., 1991a; 1993a).

Currently there are no successful vaccines for the prevention of feline immunodeficiency disease and feline infectious peritonitis disease in cats. Current feline leukemia virus vaccines are available, but their level of efficacy remains questionable and in some cases may cause the disease. Experimental feline infectious peritonitis vaccines have been shown to be non-protective or cause early death, through antibody-mediated enhancement. Therefore, there is a need in the art for agents and compositions that provide protection from these and other diseases where there is not yet an existing vaccine or that improves the efficacy of existing and commonly used vaccines. Furthermore, there is a need in the art for vaccines and agents that induce a cell-mediated response in the absence of disease enhancing antibodies. And finally, vaccination of kittens is difficult due to inability to overcome maternal antibodies in kittens. Safe and effective agents to help overcome these barriers are needed.

In the present invention, by manipulating the expression of feline CD28, feline CTLA-4 and their ligands feline CD80 and feline CD86 costimulatory molecules, it is possible to regulate T-cell responses, through augmentation, suppression or redirection, to raise a desired immune response towards a particular feline pathogen or feline disease condition. In particular, these costimulatory molecules are useful for vaccination against infectious diseases, treatment of infectious diseases, and treatment of neoplastic, degenerative, autoimmune, and immunodeficiency conditions in felines. The present invention overcomes the lack of efficacy and effectiveness of currently available feline vaccines described above.

SUMMARY OF THE INVENTION

The present inventions involves a recombinant virus which comprises at least one foreign nucleic acid inserted within a non-essential region of the viral genome of a virus, wherein each such foreign nucleic acid encodes a protein. The protein which is encoded is selected from the groups consisting of a feline CD28 protein or an immunogenic portion thereof, a feline CD80 protein or an immunogenic portion thereof, a feline CD86 protein or an immunogenic portion thereof, or a feline CTLA-4 protein or an immunogenic portion thereof. The portion is capable of being expressed when the recombinant virus is introduced into an appropriate host.

The present invention also involves a recombinant virus further comprising a foreign nucleic acid encoding an immunogen derived from a pathogen. The present invention also comprises recombinant viruses which are capable of enhancing an immune response in a feline. The present invention also comprises recombinant viruses which are capable of suppression an immune response in a feline.

BRIEF DESCRIPTION OF THE FIGURES

FIG. 1A: DNA and animo acid sequence of feline CD80 (B7-1) (TAMU). (SEQ ID NO. 1 and 2)

FIG. 2A: DNA and amino acid sequence of feline CD80 (b7-1) (SYNTRO). (SEQ ID NO. 3 and 4)

FIG. 3A: DNA and animo acid sequence of feline CD86 (B7-2). (SEQ ID NO. 5 and 6)

FIG. 4A: DNA and amino acid sequence of feline CD28. (SEQ ID NO. 7 and 8)

FIG. 4B: Hydrophobicity plot of amino acid sequence of feline CD28.

FIG. 5A: DNA and animo acid sequence of feline CTLA-4 (CD152). (SEQ ID NO. 9 and 10)

DETAILED DESCRIPTION OF THE INVENTION

Figure 1B:
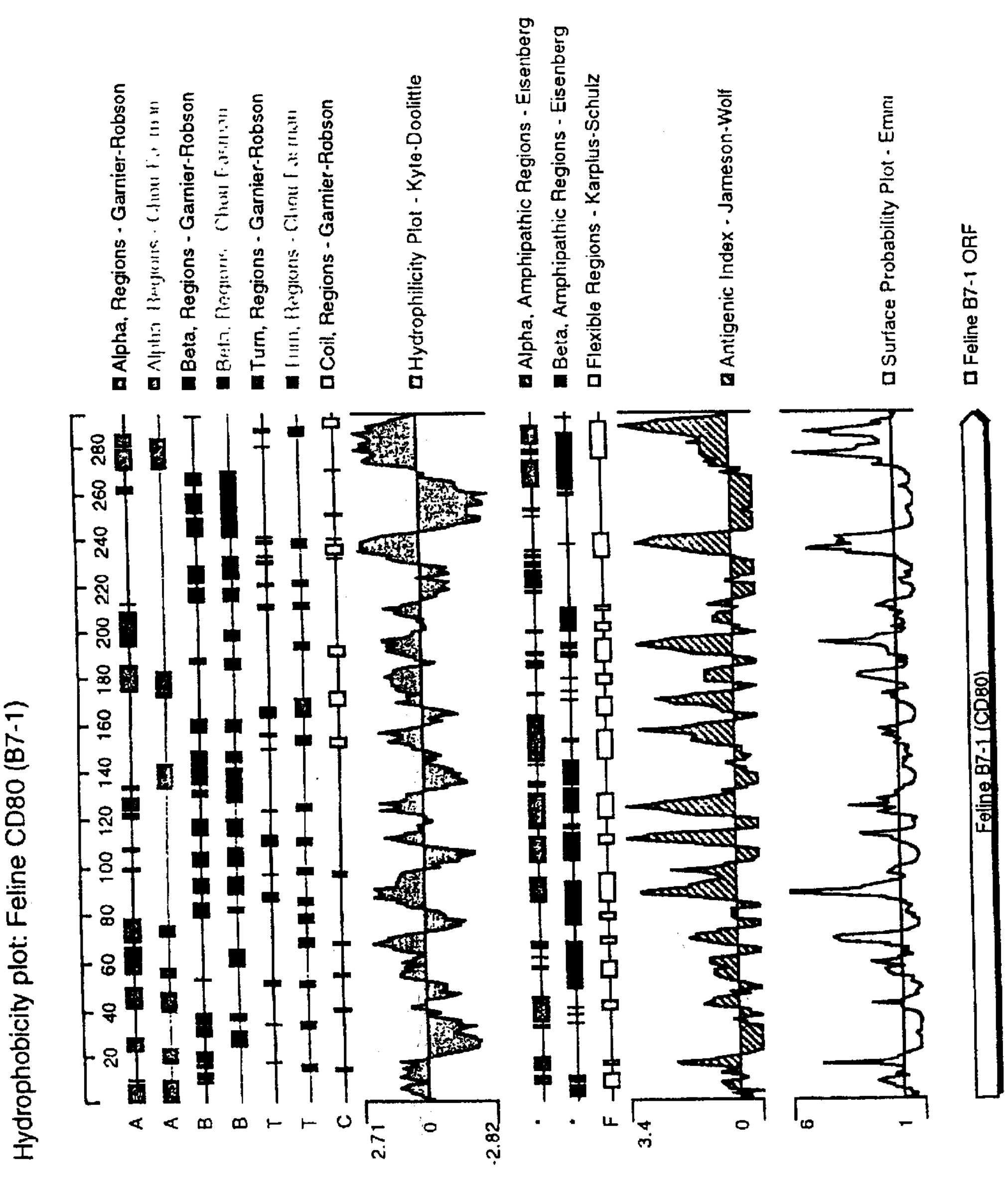
FIG. 1B: Hydrophobicity plot of amino acid sequence of feline CD80 (B7-1) (TAMU).

The present invention involves a recombinant virus which comprises at least one foreign nucleic acid inserted within a non-essential region of the viral genome of a virus, wherein each such foreign nucleic acid (a) encodes a protein selected from the groups consisting of a feline CD28 protein or an immunogenic portion thereof; a feline CD80 protein or an immunogenic portion thereof; a feline CD86 protein or an immunogenic portion thereof; of a feline CTLA-4 protein or an immunogenic portion thereof and (b) is capable of being expressed when the recombinant virus is introduced into an appropriate host.

In an embodiment of the above-described invention the recombinant virus comprises at least two foreign nucleic acids, each inserted within a non-essential region of the viral genome.

In another embodiment of the invention the recombinant virus comprises at least three foreign nucleic acids, each inserted within a non-essential region of the viral genome.

In another embodiment of the invention the recombinant virus comprises four foreign nucleic acids, each inserted within a non-essential region of the viral genome.

In another embodiment the recombinant virus includes but is not limited to a raccoonpox virus, a swinepox virus, or a feline herpesvirus.

In a further embodiment of the above-identified invention the recombinant virus comprises more than one foreign nucleic acid, and each foreign nucleic acids is inserted into the same nonessential region. In another embodiment the recombinant virus of any comprises more than one foreign nucleic acid wherein all such foreign nucleic acids are not inserted into the same nonessential region.

In a separate embodiment the recombinant virus of any of comprises a foreign nucleic acid which encodes an immunogen derived from a pathogen. In a further embodiment of the invention the recombinant virus encodes a feline pathogen, a rabies virus pathogen, a Chlamydia pathogen, a Toxoplasmosis gondii pathogen, a Dirofilaria immitis pathogen, a flea pathogen, or a bacterial pathogen. In another embodiment of the invention the recombinant virus encodes a feline immunodeficiency virus (FIV), feline leukimia virus (FeLV), feline infectious peritonitis virus (FIP), feline panleukopenia virus, feline calicivirus, feline reovirus type 3, feline rotavirus, feline coronavirus, feline syncytial virus, feline sarcoma virus, feline herpesvirus, feline Borna disease virus, or a feline parasite.

In a further embodiment of the invention the recombinant virus comprises at least one foreign nucleic acid which comprises a promoter for expressing the foreign nucleic acid. In another embodiment the recombinant virus expresses at least one foreign nucleic acid under the control of a promoter endogenes to the virus.

In one embodiment of the invention the recombinant virus further comprises a foreign nucleic acid encoding a detectable marker. In a further embodiment of the the invention the detectable marker is *E. coli* beta galactosidase.

The invention further provides a recombinant virus encoding immunogens from a FIV gag protease, a FIV envelope protein, a FeLV gag protease, or a FeLV envelope protein.

The invention provides for a recombinant virus further comprising a nucleic acid encoding feline immunodeficiency virus genome or a portion thereof. The invention provides for a recombinant virus further comprising a nucleic acid encoding feline leukemia virus genome or a portion thereof. The invention provides for a recombinant virus further comprising a nucleic acid encoding feline IL12, GM-CSF, p35 or p40. The invention further provides for a vaccine which comprises an effective immunizing amount of such recombinant virus and a suitable carrier.

The invention provides a recombinant feline herpesvirus containing a nonessential region is the glycoprotein G gene of feline herpes virus. The invention provides for a recombinant feline herpesvirus of claim 12 designated S-FHV-031 (ATCC Accession No. VR-2604). This virus was deposit on May 1, 1998 with the American Type Culture Collection (ATCC), 10801 University Boulevard, Manassas, Va. 20108-0971, U.S.A. under the provision of the Budapest Treaty for the International Recognition of the Deposit of Microorganism for the Purpose of Patent Procedure.

The invention provides for a recombinant swinepox virus with a nonessential region in the larger Hind III to Bgl II subfragment of the Hind III M fragment of swinepox virus. The invention further provides a recombinant feline swinepox of claim 14 designated S-SPV-246 (ATCC Accession No. VR-2603). This virus was deposited on May 1, 1998 with the American Type Culture Collection (ATCC), 10801 University Boulevard, Manassas, Va. 20108, U.S.A. under the provision of the Budapest Treaty for the International Recognition of the Deposit of Microorganism for the Purpose of Patent Procedure.

In an embodiment of the above-described invention the recombinant virus, the portion of the CD28, CD80, or CD86 protein in the soluble portion of the protein. In another embodiment of the invention the recombinant virus contains foreign nucleic acid which encodes the feline CTLA-4 protein.

The above-described invention for a vaccine which comprises an effective immunizing amount of a recombinant virus and a suitable carrier. In one embodiment of the invention a vaccine contains an effective immunizing amount of the recombinant virus between about $1\times10^5$ pfu/ml and about $1\times10^8$ cfu/ml and about cfu/ml. In another embodiment the invention provides a vaccine which further comprises an admixture with the recombinant virus and an effective immunizing amount of an a second immunogen.

The invention provides for a method for enhancing an immune response in a feline which comprises administering to the feline an effective immunizing amount of any of the above-identified recombinant viruses. The invention further provides for a method for immunizing a feline by administering to the feline an effective immunizing amount of the any of the above-identified recombinant viruses.

The invention provides for method for suppressing an immune response in a feline by administering to the feline any effective suppressing amount a recombinant virus containing a soluble CD28, CD80, or CD86. The invention provides for a method for suppressing an immune response in a feline by administering to the feline any effective suppressing amount a recombinant virus containing feline CTLA-4 protein.

The invention provides for administering the above described recombinant virus by intravenous, subcutaneous, intramuscular, transmuscular, topical, oral, or intraperitoneal routes.

In one embodiment, the invention provides a method of suppressing the immune response in a feline when the feline is the recipient of a transplanted organ or tissue of is suffering from an immune response. In a further embodiment the invention provides a method for suppressing an immune response in a feline which comprises administering to the feline an antisense nucleic acid capable of hybridizing to and inhibiting translation of: (a) a feline CD28 mRNA transcript , (b) a feline CD80 transcript, or (c) a feline CD86 mRNA transcript the antisense nucleic acid begin present in an amount effective to inhibit translation and thus suppress the immune response in the feline.

In one embodiment the above-described invention provides a method for reducing or abrogating a tumor in a feline which comprises administering to the tumor in the feline a recombinant virus containing nucleic acid which encodes a feline CD80 protein, a feline CD80 protein or a combinantion thereof in an amount effective to reduce or abrogate the tumor.

In one embodiment the invention provides a method for reducing or abrogating a tumor in a feline wherein the recombinant virus further comprises, and is capable of expressing a feline tumor associated antigen and the administration is effected systemically.

The present invention provides isolated and purified DNA encoding feline CD80 (B7-1) ligand or feline CD86 (B7-2) ligand or feline CD28 receptor or feline CTLA-4 (CD152) receptor, as well as cloning and expression vectors comprising CD80 or CD86 or CD28 or CTLA-4 or RNA, in part or whole, and cells transformed with CD80-encoding vectors or CD86-encoding vectors or CD28-encoding vectors or CTLA-4-encoding vectors. Feline species from which CD80 or CD86 or CD28 or CTLA-4 are selected are from the group comprising, but not limited to domestic cats, lions, pumas, bobcats, and cheetans.

The invention provides isolated and purified feline CD80 (B7-1) cDNA of approximately 941 nucleotides. The inventio also provides isolated and purified feline CD80 polypeptide of approximately 292 amino acids, the native membrane bound or mature form which as a molecular mass of about 33,485 kDa, an isoelectric point of about 9.1, a net charge at pH 7.0 of 10. The coexpression of CD80, with the costimulatory molecule CD28, and a tumor antigen or an antigen from a pathogenic organism, has the ability to activate or enhance activation of T-lymphocytes, inducing the production of immune stimulating cytokine and to regulate the growth of other cell types. The coexpression of Cd80, with costimulatory molecule CTLA-4, has the ability to regulate activation of T-lymphocytes.

The invention provides isolated and purified feline CD86 (B7-2) cDNA of approximately 1176 nucleotides. The invention also provides isolated and purified feline CD86 polypeptide of approximately 320 amino acids, the native membrane bound or mature form of which has a molecular mass of approximately 36,394 kDa, an isoelectric point of about 9.19, a net charge at pH 7.0 of 11.27. The coexpression of CD86, with costimulatory molecules CD28 and a tumor antigen or an antigen from a pathogenic organism, has the ability to activate or rehance activation of T-lymphhocytes, inducing the production of immune stimulating cytokines and to regulate the growth of other cell types. The coexpression of CD86, with constimulatory molecule CTLA-4, has the ability to regulate activation of T-lymphocytes.

Feline CD80 or CD86 according to the present invention are obtained from native or recombinant sources. Feline CD80 or CD86 according to the present invention comprises the native and membrane bound form or a secreted form lacking the transmembrane domain.

The invention provides isolated and purified feline CD28 cDNA of approximately 689 nucleotides. The invention also provides isolated and purified feline CD28 polypeptide of approximately 221 amino acids, the native membrane bound or mature form which has a molecular mass of about 25,319 kDa, an isoelectric point of about 9.17, a net charge at pH 7.0 of 9.58.

The invention provides isolated and purified feline CTLA-4 cDNA of approximately 749 nucleotides. The invention also provides isolated and purified feline CTLA-4 polypeptides of approximately 223 amino acids, that native membrane bound or mature form which has a molecular mass of about 24,381 kDa an isoelectric point of about 6.34, a net charge at pH 7.0 of −0.99.

The invention provides a recombinant swinepox virus expressing foreign DNA, the foreign DNA encoding Feline CD80, Feline CD86, Feline CD28, and Feline CTLA-4 cDNA and polypeptides.

The invention provides a recombinant raccoonpox virus expressing foreign DNA, the foreign DNA encoding Feline CD80, Feline CD86, Feline CD28, and Feline CTLA-4 cDNA and polypeptides.

The invention provides a recombinant feline herpesvirus expressing foreign DNA, the foreign DNA encoding Feline CD80, Feline CD86, Feline CD28, and Feline CTLA-4 cDNA and polypeptides.

In another aspect, the invention provides a method of enhancing an immune response in a felid to an immunogen, which is achieved by administering the immunogen before, after or substantially simultaneously with the feline CD80 or feline CD86 with our without feline CD28 or feline CTLA-4 in a recombinant swinepox virus vector, recombinant raccoonpox virus vector, or recombinant feline herpesvirus vector, in an amount effective to enhance the immune response.

In another aspect, the invention provides a method of suppressing an immune response in a felid to an immunogen, which is achieved by administering the immunogen before, after or substantially simultaneous with the feline CD80 or feline CD86 with or without feline CD28 or feline CTLA-4 or with antisense RNA or DNA, in part or whole, encoding feline CD80 or feline CD86 or feline CD28 or feline CTLA-4, in a recombinant swinepox virus vector, recombinant raccoonpox virus vector, or recombinant feline herpesvirus vector, in an amount effective to suppress the immune response.

In another aspect, the invention provides a vaccine for inducing an immune response in felids to an immunogen comprising the immunogen and an effective amount of feline CD80 in a recombinant swinepox virus vector, recombinant raccoonpox virus vector, or recombinant feline herpesvirus vector, for immune response enhancement. The immunogen is derived, for example, from feline pathogens such as feline immunodeficiency virus, feline leukemia virus, feline parvovirus, feline coronavirus, feline leptovirus, and the like.

In another aspect, the invention provides a vaccine for inducing an immune response in fields to an immunogen, which is achieved by administering a recombinant swinepox virus vector, recombinant raccoonpox virus vector, or recombinant feline herpesvirus vector, expressing DNA or RNA of an immunogen and DNA or RNA of feline CD80, CD86, CD28 accessory molecules, in any combination, encoding the proteins or fragment of proteins in an amount effective to modulate the immune response.

The feline CD80 protein has an amino acid sequence which is 59% and 46% identical with the human and mouse proteins, respectively. The feline CD86 protein has an amino acid sequence which is 68% and 64% identical with the human and rabbit proteins, respectively. The feline CD28 protein has an animo acid sequence which is 82% and 74% identical with the human and mouse proteins, respectively. The feline CTLA-4 proteins has an animo acid sequence which is 88% and 78% identical with the human and mouse proteins, respectively. The human or mouse CD80 or CD86 proteins cannot functionally replace the feline CD80 or CD86 proteins. Therefore, the feline CD80, feline CD86, feline CD28 and feline CTLA-4 are novel reagents required for the regulation of immunity in felids.

The present invention encompasses T-cell regulatory accessory molecules, CD80 (B7-1) or CD86 (B7-2) or CD28 or CTLA-4 (CD152) from feline species. The invention provides isolated and purified nucleic acids encoding, in part or whole, feline CD80 or feline CD86 or feline CD28 or feline CTLA-4, as well as CD80, CD86, CD28 or CTLA-4 polypeptides purified from either native or recombinant sources. Feline CD80, CD86, CD28 or CTLA-4 produced according to the present invention is used to enhance the efficiency of feline vaccines against tumors and pathogenic organism and as a therapeutic to treat viral and bacterial disease in cats. Feline CD80, CD86, CD28 or CTLA-4 produced according to the present invention is also used to alleviate disease due to overactive, hyperactive or misdirected immune response.

Nucleic Acids, Vectors, Transformants

The sequences of the cDNA encoding feline CD80 (SEQ ID NO: 1, 3), feline CD86 (SEQ ID NO: 5), feline CD28 (SEQ ID NO: 7), or feline CTLA-4 (SEQ ID NO: 9), are shown in FIGS. 1 to 5, and the predicted amino acid sequences of feline CD80 (SEQ ID NO: 2, 4), feline CD86 (SEQ ID NO: 6), feline CD28 (SEQ ID NO: 8), or feline CTLA-4 (SEQ ID NO: 10), are shown in FIGS. 1 to 5. The designation of these feline polypeptides as CD80, CD86, CD28 or CTLA-4 is based on partial amino acid sequence homology to human or mouse or rabbit homologue of these polypeptides, and the ability of the CD 80 or CD86 polypeptides to bind to feline CD28 receptor (see below) or to CTIA-4 and to activate or stimulate or otherwise regulate activation of T-lymphocytes. Furthermore, without wishing to be bound by theory, it is predicted that feline CD80 or feline CD86 polypeptides also exhibit one or more of the following bioactivities: activation of NK (natural killer) cells, stimulation of B-cell maturation, activation of MHC restricted cytotoxic T-lymphocytes, proliferation of mast cells, interaction with cytokine receptors and induction of immune-regulating cytokines.

Because of the degeneracy of the genetic code (i.e., multiple codon encode certain amino acids), DNA sequences other than that shown in FIGS. 1 to 5 can also encode the feline CD80, CD86, CD28 or CTLA-4 amino acid sequences shown in FIGS. 1 to 5. Such other DNAs include those containing “sequence-conservative” variations in which a change in one or more nucleotides in a given codon results in no alteration in the amino acid encoded at that position. Furthermore, a given amino acid residue in a polypeptide can often be changed without altering the overall conformation and function of the native polypeptide. Such “function-conservative” variants include, but are not limited to, replacement of an amino acid with one having similar physico-chemical properties, such as, for example, acidic, basic, hydrophobic, hydrophilic, aromatic and the like (e.g., replacement of lysine with arginine, aspartate with glutamate, or glycine with alanine). In addition, amino acid sequences are added or deleted without destroying the bioactivity of the molecule. For example, additional amino acid sequences are added at either amino- or carboxy-terminal ends to serve as purification tags, such as histidine tags, (i.e., to allow one-step purification of the protein, after which they are chemically or enzymatically removed). Alternatively, the additional sequences confer an additional cell-surface binding site or otherwise alter the target cell specificity of feline CD80, CD86, CD28 or CTLA-4, such as with the addition of an antigen binding site for antibodies.

The feline CD80 or feline CD86 or feline CD28 or feline CTLA-4 cDNAs within the scope of the present invention are those of FIGS. 1 to 5, sequence-conservative variant DNAs, DNA sequences encoding function-conservative variant polypeptides, and combinations thereof. The invention encompasses fragments of feline CD80, CD86, CD28 or CTLA-4 that exhibit a useful degree of bioactivity, either alone or in combination with other sequences or components. As explained below, it is well within the ordinary skill in the art to predictively manipulate the sequence of CD80, CD86, CD28 or CTLA-4 and establish whether a given feline CD80, CD86, CD28 or CTLA-4 variant possesses an appropriate stability and bioactivity for a given application, or variations that affect the binding activities of these molecules resulting in increased effectiveness. Feline CD80 and CD86 will each bind to coreceptor CD28 or to coreceptor CTLA-4. This can be achieved by expressing and purifying the variant CD80, CD86, CD28 or CTLA-4 polypeptide in a recombinant system and assaying its T-cell stimulatory activity and/or growth-promoting activity in cell culture and in animals, followed by testing in the application. The variant CD80 is tested for bioactivity by functional binding to the CD28 or CTLA-4 receptors. The variant CD86 is tested for bioactivity by functional binding to the CD28 or CTLA-4 receptors. In a similar manner, variant CD28 or variant CTLA-4 is tested for bioactivity.

The present invention also encompasses feline CD80, CD86, CD28 or CTLA-4 DNAs (and polypeptides) derived from other feline species, including without limitation domestic cats, lions, tigers, cheetahs, bobcats and the like. Feline CD80, CD86, CD28 or CTLA-4 homologue of the sequence shown in FIGS. 1 to 5 are easily identified by screening cDNA or genomic libraries to identify clones that hybridize to probes comprising all or part of the sequence of FIGS. 1 to 5. Alternatively, expression libraries are screened using antibodies that recognize feline CD80, CD86, CD28 or CTLA-4. Without wishing to be bound by theory, it is anticipated that CD80 or CD86 genes from other feline species will share at least about 70% homology with the feline CD80, CD86, CD28 or CTLA-4 genes. Also within the scope of the invention are DNAs that encode homologue of CD80, CD86, CD28 or CTLA-4, defined as DNA encoding polypeptides that share at least about 25% amino acid identity with feline CD80, CD86, CD28 or CTLA-4.

Generally, nucleic acid manipulations according to the present invention use methods that are well known in the art, such as those as disclosed in, for example, *Molecular Cloning, A Laboratory Manual* (2nd Ed., Sambrook, Fritsch and Maniatis, Cold Spring Harbor), or *Current Protocols in Molecular Biology* (Eds. Aufubel, Brent, Kingston, More, Feidman, Smith and Stuhl, Greene Publ. Assoc., Wiley-Interscience, NY, N.Y., 1992).

The present invention encompasses cDNA and RNA sequences and sense and antisense. The invention also encompasses genomic feline CD80, CD86, CD28 or CTLA-4 DNA sequences and flanking sequences, including, but not limited to, regulatory sequences. Nucleic acid sequences encoding feline CD80, CD86, CD28 or CTLA-4 polypeptide(s) are also associated with heterologous sequences, including promoters, enhances, response elements, signal sequences, polyadenylation sequences, introns, 5'- and 3'-noncoding regions, and the like. Transcriptional regulatory elements that are operably linked to feline CD80, CD86, CD28 or CTLA- 4 cDNA sequence(s) include without limitation those that have the ability to direct the expression of genes derived from prokaryotic cells, eukaryotic cells, viruses of prokaryotic cells, viruses of eukaryotic cells, and any combination thereof. Other useful heterologous regulatory sequences are known to those skilled in the art.

The nucleic acids of the present invention are modified by methods known to those skilled in the art to alter their stability, solubility, binding affinity, and specificity. For example, the sequences are selectively methylated. The nucleic acid sequences of the present invention are also modified with a label capable of providing a detectable signal, either directly or indirectly. Exemplary labels include radioisotopes, fluorescent molecules, biotin, and the like.

The present invention also provides vectors that include nucleic acids encoding CD80, CD86, CD28 or CTLA-4 polypeptide(s) in part or in whole. Such vectors include, for example, plasmid vectors for expression in a variety of eukaryotic and prokaryotic hosts. Preferably, vectors also include a promoter operably linked to the feline CD80, CD86, CD28 or CTLA-4 polypeptide encoding portion. The encoded feline CD80, CD86, CD28 or CTLA-4 polypeptide(s) are expressed by using any suitable vectors and host cells as explained herein or otherwise known to those skilled in the art.

The present invention also provides vectors that include nucleic acids encoding the feline CD80, CD86, CD28 or CTLA-4 polypeptide(s) in part or in whole. Such vectors include, for example, live viral vectors for expression in a variety of eukaryotic hosts, or for the expression of DNA or RNA vaccines. In one embodiment, the live viral vector is attenuated. In another embodiment, the live viral vector is attenuated by a gene deletion. In another embodiment, the viral vector is inactivated by chemical treatment or heat. The live viral vector is selected from the group comprising, but is not limited to, herpesvirus, poxvirus, adenovirus, adeno-associated virus, retrovirus, baculovirus, alphavirus, rhabdovirus, picornavirus. The live viral vector is selected from the group comprising, but is not limited to, feline herpesvirus, canine herpesvirus, avian herpesvirus, bovine herpesvirus, equine herpesvirus, pseudorabies virus, swine-pox virus, avipox virus, fowlpox virus, raccoonpox virus, canarypox virus, vaccinia virus, Malony murine leukemia virus, Sindbis virus, and Semliki Forest virus The live viral vector is a recombinant viral vector expressing a foreign DNA which is feline CD80, CD86, CD28 or CTLA-4 cDNA in part or in whole. The foreign DNA is also a cDNA for an antigen from a pathogenic organism. The recombinant viral vector is constructed by homologous recombinant or cosmid reconstruction methods known to those skilled in the art. Preferably, vectors also include a promoter operably linked to the feline CD80, CD86, CD28 or CTLA-4 polypeptide encoding portion. The promoter is selected from the group comprising, but is not limited to, feline herpesvirus gE promoter, poxvirus synthetic late/early promoter, human cytomegalovirus immediate early promoter, pseudorabies virus gX promoter. Promotion of gene expression also includes the expression of CD80, CD86, CD28 or CTLA-4 cDNA from an internal ribosome entry site (IRES) element contained in a cassette (pCITE vector, Novagen, Madison, Wis.). The cell lines for growing viral vectors include, but are not limited to, Crandell feline kidney cells (CRFK), chick embryo fibroblasts, embryonic swine kidney cells (ESK-4), porcine kidney cells (PK) . The encoded feline CD80, CD86, CD28 or CTLA-4 polypeptide(s) are expressed by using any suitable vectors and host cells as explained herein or otherwise known to those skilled in the art.

In a preferred embodiment, the genes encoding feline CD80 and CD28, CD80 and CTLA-4, CD86 and CD28, or CD86 and CTLA-4, in combination with genes for an immunogen derived from a feline pathogen, are incorporated into a single recombinant viral vector and then formulated into a live vaccine. The feline CD80, CD86, CD28 or CTLA-4 genes, alone or in combination with feline genes derived from feline pathogens are incorporated into the recombinant virus so that the expression of these genes is controlled by an appropriate promoter. In another embodiment, the genes encoding feline CD80, CD86, CD28 or CTLA-4, alone or in combination, are incorporated into a recombinant viral vector, and co-administered in a vaccine with a second recombinant viral vector which encodes genes for immunogen(s) derived from feline pathogens. These two embodiments provide the desired immune responses in the same cell or in cells in close proximity to achieve enhancement, suppression or redirection of the desired immune response.

The immunogen is selected from the group comprising, but not limited to, feline pathogens such as feline immunodeficiency virus, feline leukemia virus, feline infectious peritonitis virus, feline panleukopenia virus (parvovirus), feline calicivirus, feline reovirus type 3, feline rotavirus, feline coronavirus (Infectious peritonitis virus), rabies virus, feline syncytial virus, feline sarcoma virus, feline herpesvirus (rhinotracheitis virus), feline Borna disease virus, Chlamydia, Toxoplasmosis gondii, feline parasites, Dirofilaria immitis, fleas, bacterial pathogens, and the like.

Vectors or live viral vectors will often include one or more replication system for cloning or expression, one or more markers for selection in the host such as, for example, antibiotic resistance, or calorimetric markers such as β-galactosidase(lacZ) or β-glucuronidase (uidA), or fluorescent markers, such as green fluorescent protein, and one or more expression cassettes. The inserted coding sequences are synthesized, isolated from natural sources, prepared as hybrids, or the like. Ligation of the coding sequences to the transcriptional regulatory sequences are achieved by methods known to those skilled in the art. Suitable host cells are transformed/transfected/infected by any suitable method including electroporation, $CaCl_2$- or liposome- mediated DNA uptake, fungal infection, microinjection, microprojectile, or the like.

Suitable vectors for use in practicing the present invention include without limitation YEp352, pcDNAI (Invitrogen, Carlsbad, Calif.), pRc/CMV (Invitrogen), and pSFVl (GIBCO/BRL, Gaithersburg, Md.). One preferred vector for use in the invention is pSFV1. Suitable host cells include *E. Coli*, yeast, COS cells, PC12 cells, CHO cells, GH4C1 cells, BHK-21 cells, and amphibian melanophore cells. BHK-21 cells are a preferred host cell line for use in practicing the present invention. Suitable vectors for the construction of naked DNA or genetic vaccinations include without limitation pTarget (Promega, Madison, Wis.), pSI (Promege, Madison, Wis.) and pcDNA (Invitrogen, Carlsbad, Calif.).

Nucleic acids encoding feline CD80, CD86, CD28 or CTLA-4 polypeptide(s) are also introduced into cells by recombination events. For example, such a sequence is microinjected into a cell, effecting homologous recombination at the site of an endogenous gene encoding the polypeptide, an analog or pseudogene thereof, or a sequence with substantial identity to an feline CD80, CD86, CD28 or CTLA-4 polypeptide-encoding gene. Other recombination-based methods such as non-homologous recombinations, and deletion of endogenous gene by homologous recombination, especially in pluripotent cells, are also used.

The present invention provides a method of enhancing an immune response in a felid to an immunogen, which is achieved by administering the immunogen before, after or substantially simultaneously with the feline CD80 or feline CD86 with or without feline CD28 or feline CTLA-4 in an amount effective to enhance the immune response.

The present invention provides a method of enhancing an immune response in a felid to an immunogen, which is achieved by administering an expression vector which contains an immunogen derived from a feline pathogen and the feline CD80 or feline CD86 accessory molecules with or without feline CD28 or feline CTLA-4 in an amount effective to enhance the immune response.

The present invention provides a method of redirecting an immune response in a felid to an immunogen, which is achieved by administering an expression vector which contains an immunogen derived from a feline pathogen and the feline CD80 or feline CD86 accessory molecules with or without feline CD28 or feline CTLA-4 in an amount effective to enhance the immune response.

The present invention provides a method of suppressing an immune response in a felid to an immunogen, which is achieved by administering the immunogen before, after or substantially simultaneously with the feline CD80 or feline CD86 with or without feline CD28 or feline CTLA-4 or with antisense RNA or DNA encoding feline CD80 or feline CD86 or feline CD28 or feline CTLA-4, in an amount effective to suppress the immune response.

The present invention provides a vaccine for inducing an immune response in a felid to an immunogen(s), comprising the immunogen and effective amount of feline CD80 or feline CD86 with or without feline CD28 or feline CTLA-4 for immune response enhancement, or feline CD80 or feline CD86 with feline CTLA-4 for immune response suppression. In another embodiment the invention provides a vaccine comprising an expression vector containing genes for immunogen(s) to feline pathogens and genes for CD80, CD86, with or without feline CD28 or feline CTLA-4 for immune response enhancement or suppression.

Feline CD80, CD86, CD28 or CTLA-4 Polypeptides

Figure 2B:
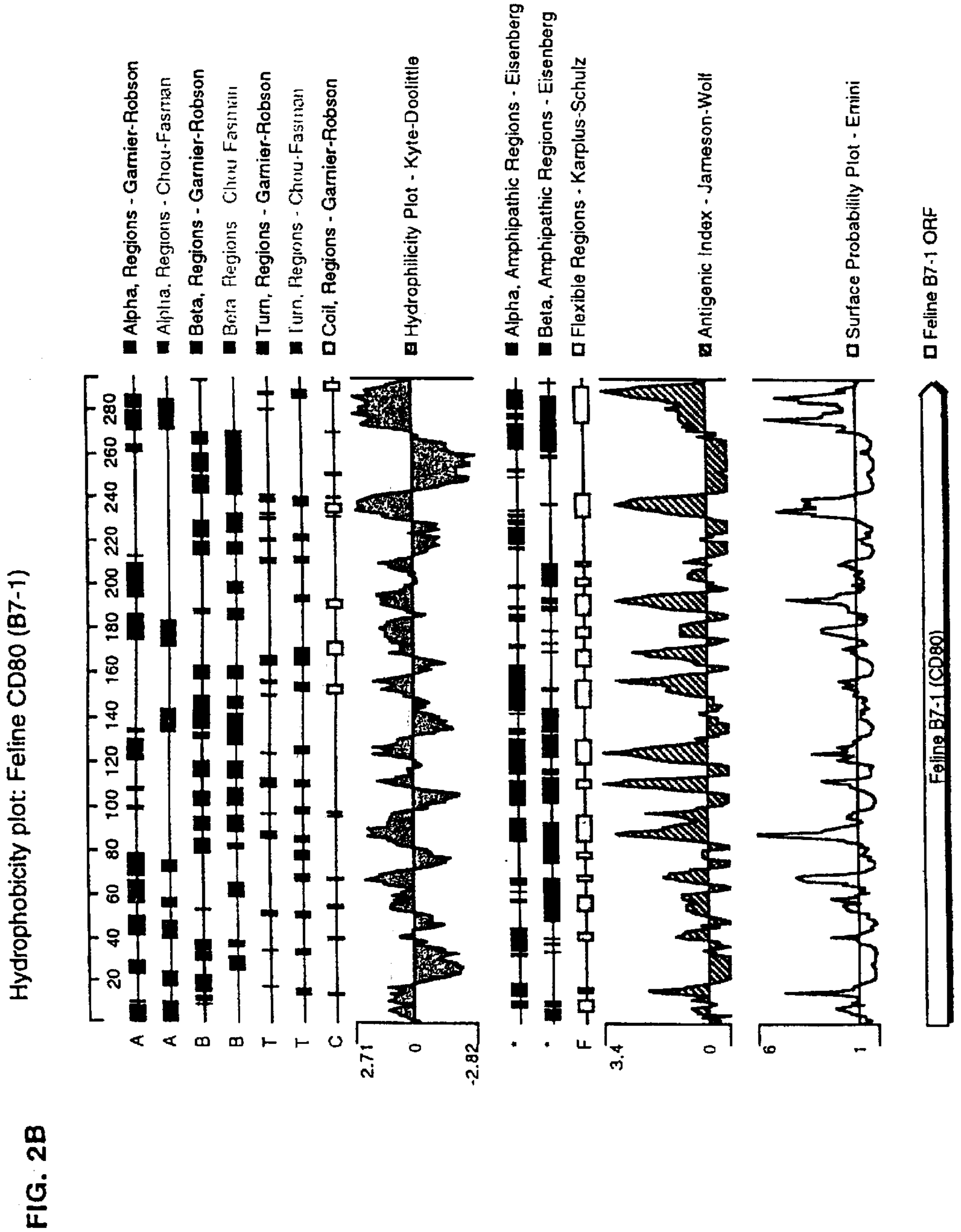
FIG. 2B: Hydrophobicity plot of amino acid sequence of feline CD80 (B7-1) (SYNTRO).
Figure 3B:
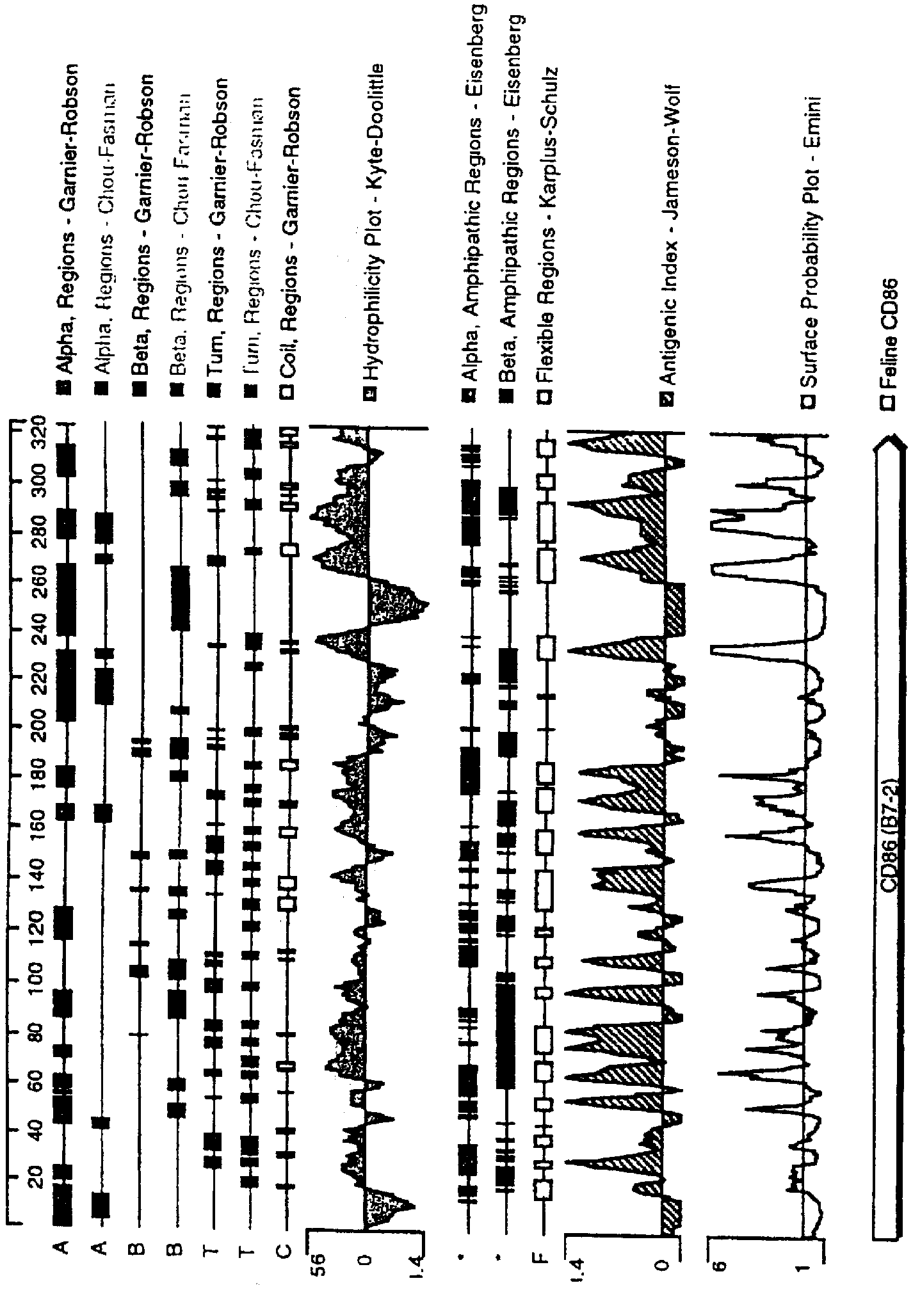
FIG. 3B: Hydrophobicity plot of amino acid sequence of feline CD86 (B7-2).
Figure 5B:
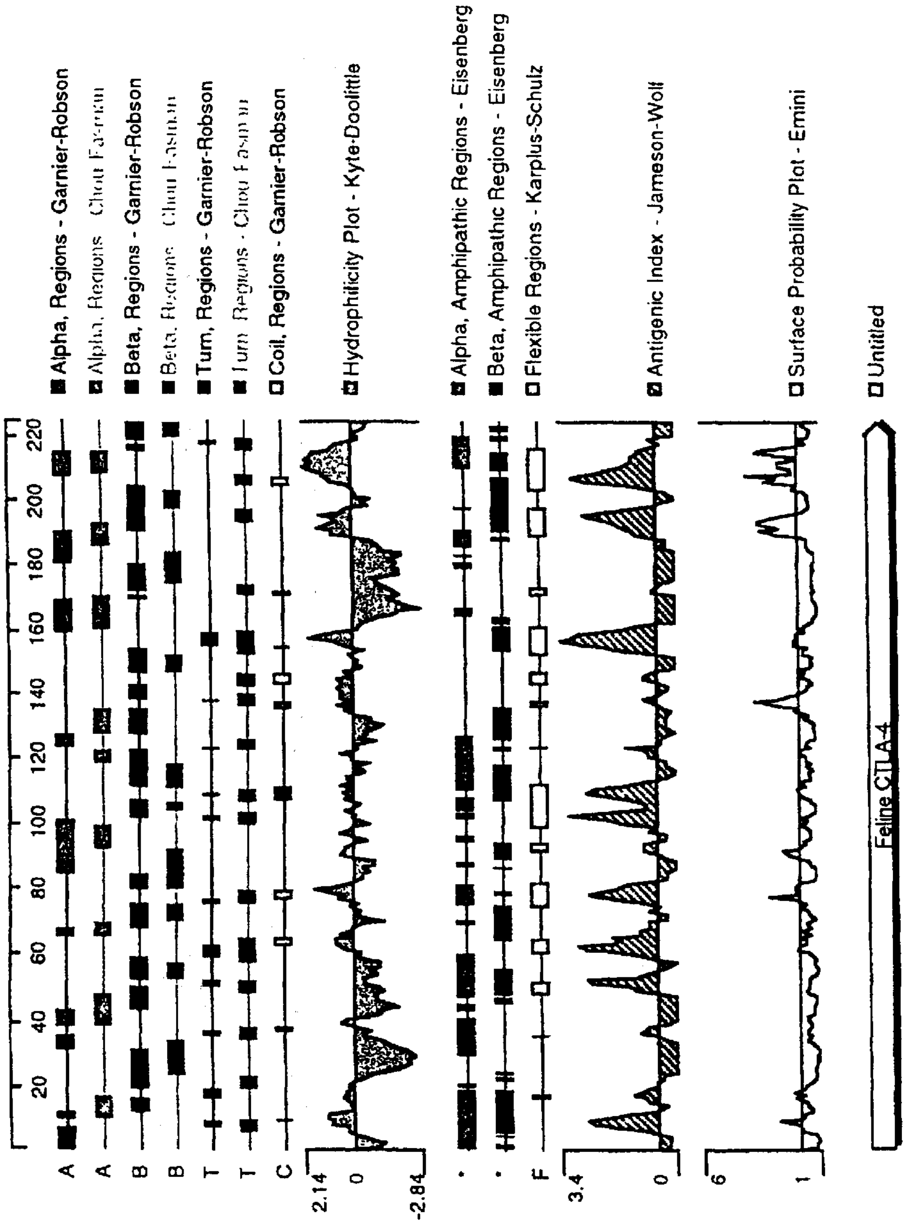
FIG. 5B: Hydrophobicity plot of amino acid sequence of feline CTLA-4 (CD152).

The feline CD80 gene (the DNA and amino acid sequence of which is shown in FIGS. 1 and 2) encodes a polypeptide of approximately 292 amino acids. The feline CD86 gene (the DNA and amino acid sequence of which is shown in FIG. 3) encodes a polypeptide of approximately 320 amino acids. The feline CD28 gene (the DNA and amino acid sequence of which is shown in FIG. 4) encodes a polypeptide of approximately 221 amino acids. The feline CTLA-4 gene (the DNA and amino acid sequence of which is shown in FIG. 5) encodes a polypeptide of approximately 223 amino acids.

Purification of feline CD80, CD86, CD28 or CTLA-4 from natural or recombinant sources is achieved by methods well-known in the art, including, but not limited to, ion-exchange chromatography, reverse-phase chromatography on C4 columns, gel filtration, isoelectric focusing, affinity chromatography, and the like. In a preferred embodiment, large quantities of bioactive feline CD80, CD86, CD28 or CTLA-4 is obtained by constructing a recombinant DNA sequence comprising the coding region for feline CD80, CD86, CD28 or CTLA-4 fused in frame to a sequence encoding 6 C-terminal histidine residues in the pSFV1 replicon (GIBCO/BRL). mRNA encoded by this plasmid is synthesized using techniques well-known to those skilled in the art and introduced into BHK-21 cells by electroporation. The cells synthesize and secrete mature glycosylated feline CD80, CD86, CD28 or CTLA-4 polypeptides containing 6 C-terminal histidines. The modified feline CD80, CD86, CD28 or CTLA-4 polypeptides are purified from the cell supernatant by affinity chromatography using a histidine-binding resin (His-bind, Novagen, Madison, Wis.).

Feline CD80 or feline CD86 polypeptides isolated from any source are modified by methods known in the art. For example, feline CD80, CD86, CD28 or CTLA-4 are phosphorylated or dephosphorylated, glycosylated or deglycosylated, and the like. Especially useful are modifications that alter feline CD80, CD86, CD28 or CTLA-4 solubility, stability, and binding specificity and affinity.

Feline CD80, CD86, CD-28, CTLA-4 Chimeric Molecules.

The present invention encompasses the production of chimeric molecules made from fragments of feline CD80, CD86, CD-28 and CTLA-4 in any combination. For example, introducing the binding site of CTLA-4 in place of the CD-28 binding site, to increase the binding affinity of CD28 while maintaining enhancement of the immune response.

In one embodiment, the binding sites for CD80 or CD86 on CTLA-4 and CD28 are exchanged such that a binding region on CD28 is replaced by a binding region of CTLA-4. The effect of the chimeric CD28 molecule with a CTLA-4 binding region is to increase the affinity of CD28 for CD80 or CD86 and increase the magnitude of enhancement of the immune response. In an alternative embodiment, chimeric molecules of CD80 and CD28 or CD86 and CD28, or fragments thereof, are membrane bound and improve the immune enhancing capabilities of these molecules. In an alternative embodiment, chimeric molecules of CD80 and CTLA-4 or CD86 and CTLA-4, or fragments thereof, are membrane bound and improve the immune suppressing capabilities of these molecules. In an alternative embodiment, chimeric molecules of CD80 and CTLA-4 or CD86 and CTLA-4, or fragments thereof, are membrane bound and redirect the immune response to achieve the desired effect.

In an alternative embodiment, the feline CD80, CD86, CD28 or CTLA-4 is a fusion protein to another polypeptide. The polypeptide includes, but is not limited to, an immunoglobulin, antigen, tumor antigen, cell surface receptor, or cell surface ligand.

Anti-Feline CD80, CD86, CD28 or CTLA-4 Antibodies

The present invention encompasses antibodies that are specific for feline CD80, CD86, CD28 or CTLA-4 polypeptides identified as described above. The antibodies are polyclonal or monoclonal, and discriminate feline CD80, CD86, CD28 or CTLA-4 from different species, identify functional domains, and the like. Such antibodies are conveniently made using the methods and compositions disclosed in Harlow and Lane, *Antibodies, A Laboratory Manual*, Cold Spring Harbor Laboratory, 1988, as well as immunological and hybridoma technologies known to those skilled in the art. Where natural or synthetic feline CD80, CD86, CD28' or CTLA-4-derived peptides are used to induce an feline CD80, CD86, CD28 or CTLA-4-specific immune response, the peptides are conveniently coupled to a suitable carrier such as KLH and administered in a suitable adjuvant such as Freund's. Preferably, selected peptides are coupled to a lysine core carrier substantially according to the methods of Tan (1988) *Proc. Natl. Acad. Sci. USA,* 85:5409-5413. The resulting antibodies, especially internal imaging anti-idiotypic antibodies, are also prepared using known methods.

In one embodiment, purified feline CD80, CD86, CD28 or CTLA-4 is used to immunize mice, after which their spleens are removed, and splenocytes used to form cell hybrids with myeloma cells to obtain clones of antibody-secreting cells according to techniques that are standard in the art. The resulting monoclonal antibodies secreted by such cells are screened using in vitro assays for the following activities: binding to feline CD80, CD86, CD28 or CTLA-4, inhibiting the receptor-binding activity of CD80, CD86, CD28 or CTLA-4, and inhibiting the T-cell stimulatory activity of CD80, CD86, CD28 or CTLA-4.

Anti-feline CD80, anti-feline CD86, anti-feline CD28 or anti-feline CTLA-4 antibodies are used to identify and quantify feline CD80, CD86, CD28 or CTLA-4, using immunoassays such as ELISA, RIA, and the like. Anti-feline CD80, anti-feline CD86, anti-feline CD28 or anti-feline CTLA-4 antibodies are also be used to immunodeplete extracts of feline CD80 or feline CD86 or feline CD28 or feline CTLA-4. In addition, these antibodies can be used to identify, isolate and purify feline CD80, CD86, CD28 or CTLA-4 from different sources, and to perform subcellular and histochemical localization studies.

Applications

Feline CD80 (B7-1) ligand, feline CD86 (B7-2) ligand, feline CD28 receptor or feline CTLA-4 (CD152) receptor produced according to the present invention can be used beneficially as a vaccine to prevent infectious disease or to promote growth in homologous or heterologous feline species. For example, the coexpression of CD80 or CD86, with costimulatory molecules CD28 or CTLA-4, in any combination, and a tumor antigen or antigens from a pathogenic organism. The coexpression of feline CD80 or CD86, with a feline CTLA-4 receptor has the ability to inhibit activation of T-lymphocytes and suppress an immune response. A specific example would be to coexpress CD80 or CD86, with FIV, FeLV, or FIP derived immunogens in a viral vector or DNA expression vector, which, when administered as a vaccine would activate, enhance or regulate the proliferation of CD4+ and CD8+ T-lymphocytes, and induce immune-regulating cytokines such as IL-2, IFN-g, IL-12, TNFa, IL-6 and the like. Another specific example would be to express CD80, CD86, CD28 or CTLA-4 in a viral vector or DNA expression vector, which, when administered as a therapeutic would regulate or re-direct the immune response.

Enhancement of immunity through the interaction of feline CD80 or CD86 with CD28 or CTLA-4 or inhibition of an immune response through the interaction of feline CD80 or CD86 with CTLA-4 takes advantage of the natural process of regulation rather than adding foreign substances that could have multiple even detrimental effects on overall or long term health. The CD80, CD86, CD28 or CTLA-4 molecules are administered with other recombinant molecules, such as those encoding antigens that are desirable for induction of immunity. The feline CD80, CD86, CD28 and/or CTLA-4 gene is inserted into an expression vector and infected or transfected into a target cell and expresses the gene product within the target cell so that it is anchored into the plasma membrane of the target cell or antigen presenting cell, or secreted outside the target cell or antigen presenting cell. An expression vector, such as a plasmid, Semliki Forest virus, a poxvirus or a herpesvirus, transfers the gene to the antigen presenting cell. The feline CD80, CD86, CD28 and/or CTLA-4 gene or fragments of genes in any combination is inserted into a DNA or RNA expression vector and injected into a felid and expresses the gene product in the felid as a "naked" DNA/RNA or genetic vaccine. The co-expression of immunogen and the CD80, CD86, CD28 and/or CTLA-4 within a target cell or felid contributes to the activation, enhanced activation, or regulation of T lymphocytes, B lymphocytes and other cells. Alternatively, the expressed protein could be administered following expression in a prokaryotic or eukaryotic system, such as a plasmid, Semliki Forest virus, a poxvirus or a herpesvirus or other viral or bacterial vector. The feline CD80, CD86, CD28, or CTLA-4 proteins normally function anchored in the cell membrane as plasma membrane accessory molecules, but may be presented in other forms, particularly without membrane anchors.

In an one embodiment, the feline CD80 and feline CD86 are soluble, lacking a transmembrane domain or hydrophobic region, and interact with costimulatory molecules CD28 or CTLA-4, in either a membrane bound or soluble form. In an alternative embodiment, the feline CD80 or feline CD86 are membrane bound and the costimulatory molecules CD28 or CTLA-4 are in a soluble form, lacking a transmembrane domain or hydrophobic region. The soluble CD28 or CTLA-4, preferably in a dimeric form, is useful for treating disease related to T-cell mediated immunosuppression in cats. Soluble CD28 or CTLA-4 prevents rejection of transplanted tissue and can be used to treat autoimmune disease. Specifically soluble CD28 or CTLA-4 is useful for preventing graft versus host disease in a bone marrow transplant. Soluble CD28 or CTLA-4 prevents binding of a cell containing membrane bound feline CD80 or CD86.

In another embodiment, the feline CTLA-4 is fused to an immunoglobulin (Ig). The CTLA-4-Ig fusion is useful to suppress an immune response or to treat an autoimmune disease. The autoimmune disease includes, but is not limited to, arthritis, psoriasis, organ transplant rejection, graft vs. host disease.

In one embodiment, the feline CD80, and/or CD86 proteins expressed in either a bound or soluble form would be used for treatment in the reduction or abrogation of feline tumors. Specifically, the feline CD80 and/or CD86 proteins would be expressed from a viral vector or from naked DNA through direct tumor injection or administered systemically in combination with or without co-vectored feline tumor associated antigens.

Sequence-conservative and functional conservative variants of feline CD80, CD86, CD28 or CTLA-4 DNA and polypeptides or a bioactive feline CD80, CD86, CD28 or CTLA-4 fragment or sub-fragment are fused in frame to another sequence, such as a cytokine, interleukin, interferon, colony stimulating factor, antigen from a pathogenic microorganism, antibody, or purification sequence, such as a his-tag or a reporter gene, such as *E. coli* lacZ, *E. coli* uidA, or green fluorescent protein.

Vaccines

The present invention encompasses methods and composition for enhancing the efficacy of an immune response in feline species. In this embodiment, feline CD80, CD86, CD28 or CTLA-4 are used in conjunction with an immunogen for which it is desired to elicit an immune response. For example, in feline vaccines containing immunogens from pathogens such as feline immunodeficiency virus and feline leukemia virus, and other pathogens such as feline parvovirus, feline leptovirus, and feline coronavirus, it is desirable to include feline CD80, CD86, CD28 or CTLA-4 in the vaccine to regulate the magnitude and quality of the immune response. For this purpose, feline CD80, CD86, CD28 or CTLA-4 purified from native or recombinant sources as described above is included in the vaccine formulation at a concentration ranging from about 0.01 to 100.0 mg per vaccine per cat. Alternatively a recombinant vector expressing feline CD80, CD86, CD28 and/or CTLA-4 and an immunogen from a feline pathogen is included in the vaccine formulation at a concentration ranging from about 0.01 to 100.0 mg per vaccine per cat in amounts, preferably in a vaccine formulation at a concentration ranging from about 0.25 mg/kg/day to about 25 mg/kg/day.

Feline CD80, CD86, CD28 or CTLA-4 are administered in conjunction with a live (i.e., replicating) viral vaccine or a non-replicating vaccine. Non-limiting examples of replicating vaccines are those comprising native or recombinant viruses or bacteria, such as modified feline herpesvirus or modified raccoonpox virus. Non-limiting examples of live viral vaccines with limited or no replication in a feline host, but expression of foreign DNA (such as feline CD80, CD86, CD28 or CTLA-4 or an immunogen from a feline pathogen) in a host cell, are modified fowlpox virus, modified swinepox virus or Semliki Forest virus. Non-limiting examples of non-replicating vaccines are those comprising killed or inactivated viruses or other microorganisms, or crude or purified antigens derived from native, recombinant, or synthetic sources, such as, for example, feline leukemia virus vaccines.

Commercial sources of feline vaccines are known to those skilled in the art (Compendium of Veterinary Pharmaceuticals, 1997) and are used in combination with the present invention for a more effective vaccine.

A vaccine for inducing and regulating an immune response in a felid to an immunogen, is comprised of an immunogen and an effective amount of feline CD80 or feline CD86 with or without feline CD28 or feline CTLA-4 for immune response enhancement, or feline CD80 or feline CD86 with feline CTLA-4 for immune response suppression.

The immunogen is selected from the group comprising, but not limited to, feline pathogens such as feline immunodeficiency virus, feline leukemia virus, feline infectious peritonitis virus, feline panleukopenia virus (parvo), feline calicivirus, feline reovirus type 3, feline rotavirus, feline coronavirus (Infectious peritonitis), rabies virus, feline syncytial virus, feline sarcoma virus, feline herpesvirus (rhinotracheitis virus), feline Borna disease virus, Chlamydia, Toxoplasmosis gondii, feline parasites, Dirofilaria immitis, fleas, bacterial pathogens, and the like.

Regulation of the growth or regulation of activation of a cell type, such as a T-lymphocyte, indicates that the regulatory response either stimulates or suppresses cell growth. Regulation of an immune response in a felid indicates that the immune response is either stimulated or suppressed to treat the disease or infectious agent in the felid.

In a preferred embodiment, the genes encoding feline CD80 and CD28, CD80 and CTLA-4, CD86 and CD28, or CD86 and CTLA-4, in combination with genes for an immunogen from a feline pathogen, are incorporated into a single recombinant viral vector and then formulated into a live vaccine. The feline CD80, CD86, CD28 or CTLA-4 genes, alone or in combination with feline immunogen genes are incorporated into the recombinant virus so that the expression of these genes is controlled by an appropriate promoter. Administration of the vaccine results in the expression of bioactive feline CD80 or CD86 ligands, and CD28 or CTLA-4 receptors and expression of the feline immunogen(s), in the same cell, thus providing primary and secondary costimulatory signals which are needed for enhancing the desired immune response. This embodiment provides for an early, localized, immune response to the feline immunogen and a vaccine against feline disease with improved efficacy.

In another embodiment, the genes encoding feline CD80, CD86, CD28 or CTLA-4, alone or in combination, are incorporated into a recombinant viral vector, and co-administered in a vaccine with a second recombinant viral vector which encodes genes for feline immunogen(s), thus providing the desired responses in the same cell or in cells in close proximity to achieve enhancement of the desired immune response and a vaccine against feline disease with improved efficacy.

The following are examples of recombinant viral vectors for use in expression of feline CD80, CD86, CD28, and CTLA4, and for use in a vaccine to produce an improved protective immune response to challenge with a pathogenic microorganism:

1. Expression of feline CD80, CD86, CD28, and CTLA4, alone or in any combination there of, in part or in whole, in a recombinant swinepox virus (inserted into any non-essential insertion site). For non-replicating vaccination purposes, used alone, or in combination with another vaccine or therapeutic agent (recombinant, live, or killed) for use in felids, but not limited to, felids.
2. Expression of feline CD80, CD86, CD28, and ° CTLA4, alone or in any combination there of, in part or in whole, in a recombinant feline herpesvirus (inserted into the FHV gE site, or any non-essential insertion site). For replicating vaccination purposes, used alone, or in combination with a vaccine or therapeutic agent (recombinant, live, or killed) for use in felids, but not limited to felids.
3. Expression of feline CD80, CD86, CD28, and CTLA4, alone or in any combination there of, in part or in whole, in a recombinant raccoonpox virus (inserted into any non-essential insertion site). For replicating vaccination purposes, used alone, or in combination with another vaccine or therapeutic agent (recombinant, live, or killed) for use in felids, but not limited to felids.
4. Expression of feline CD80, CD86, CD28, and CTLA4, alone or in any combination, in part or in whole, in a recombinant swinepox virus containing genes for FIV gag-protease and/or envelope.
5. Expression of feline CD80, CD86, CD28, and CTLA4, alone or in any combination, in part or in whole, in a recombinant feline herpesvirus containing genes for FIVgag-protease and/or envelope.
6. Expression of feline CD80, CD86, CD28, and CTLA4, alone or in any combination, in part or in whole, in a recombinant raccoonpox virus containing genes for FIVgag-protease and/or envelope.
7. Expression of feline CD80, CD86, CD28, and CTLA4, alone or in any combination, in a recombinant swinepox virus containing genes for FeLV gag-protease and/or envelope.
8. Expression of feline CD80, CD86, CD28, and CTLA4, alone or in any combination, in part or in whole, in a recombinant feline herpesvirus containing genes for FeLV gag-protease and/or envelope.
9. Expression of feline CD80, CD86, CD28, and CTLA4, alone or in any combination, in part or in whole, in a recombinant raccoonpox virus containing genes for FeLV gag-protease and/or envelope.
10. Expression of feline CD80, CD86, CD28, and CTLA4, alone or in any combination, in part or in whole, in a recombinant swinepox virus containing genes for FeLV gag-protease and/or envelope and FIVgag-protease and/or envelope, or any combination thereof.
11. Expression of feline CD80, CD86, CD28, and CTLA4, alone or in any combination, in part or in whole, in a recombinant feline herpesvirus containing genes for FeLV gag-protease and/or envelope and FIVgag-protease and/or envelope, or any combination thereof.
12. Expression of feline CD80, CD86, CD28, and CTLA4, alone or in any combination, in part or in whole, in a recombinant raccoonpox virus containing genes for FeLV gag-protease and/or envelope and FIV gag-protease and/or envelope, or any combination thereof.

13. Expression of feline CD80, CD86, CD28, or CTLA4, alone or in any combination, in part or in whole, in swinepox virus or raccoonpox virus, or any other expression system including, but not limited to *E. coli*, Semliki forest virus and baculovirus, for the purposes of generating unpurified or purified polypeptide. Uses including, but not limited to generation of polyclonal and monoclonal antibodies, and generation of reagents for functional assay development.
14. Expression of feline CD80, CD86, CD28, or CTLA-4, alone or in any combination in a FIV or FeLV attenuated viral vector. In one embodiment the FIV or FeLV viral vector is attenuated by gene deletion.
15. Expression of feline CD80, CD86, CD28, or CTLA-4, alone or in any combination in part or in whole, in an expression vector containing gene(s) for feline immunogens for the purpose of administering as a genetic vaccine or naked DNA vaccine. Vectors include but are not limited to: pTarget( Promega, Madison, Wis.), pcDNA (Invitrogen, Carlsbad, Calif.). (Donnelly J J, et al., 1997; Hassett and Whitton, 1996.)
16. The genes or fragments of the genes for CD80, CD86, CD28, and CTLA-4, alone or in any combination, in part or in whole, may be inserted or transfected into the chromosomes of a felid or other mammal. Such integration of these genes or fragments of these genes as may be achieved with a retroviral vector and may be used as a form of gene therapy.

The present invention provides methods and compositions for improving resistance to disease of feline species for medical and/or commercial purposes. In this embodiment, feline CD80, CD86, CD28 or CTLA-4, expressed alone or in any combination, in part or in whole, and in combination with or without genes encoding feline immunogens, is administered to felids using any appropriate mode of administration. For growth promotion or disease resistance, feline CD80, CD86, CD28 or CTLA-4, expressed alone or in any combination is administered in a formulation at a concentration ranging from about 0.01 to 100.0 mg per vaccine per cat in amounts, preferably in a formulation at a concentration ranging from about 0.25 mg/kg/day to about 25 mg/kg/day. For growth promotion or disease resistance, a recombinant viral vector expressing feline CD80, CD86, CD28 or CTLA-4, alone or in any combination is administered in a formulation at a concentration ranging from about 0.01 to 100.0 mg per vaccine per cat in amounts, preferably in a formulation at a concentration ranging from about 0.25 mg/kg/day to about 25 mg/kg/day. It will be understood that the required amount of feline CD80, CD86, CD28 or CTLA-4 can be determined by routine experimentation well-known in the art, such as by establishing a matrix of dosages and frequencies and comparing a group of experimental units or subjects to each point in the matrix.

According to the present invention, native or recombinant feline CD80, CD86, CD28 or CTLA-4 is formulated with a physiologically acceptable carrier, such as, for example, phosphate buffered saline or deionized water. The formulation may also contain excipients, including lubricant(s), plasticizer(s), absorption enhancer(s), bactericide(s), and the like that are well-known in the art. The feline CD80, CD86, CD28 or CTLA-4 polypeptide of the invention is administered by any effective means, including without limitation intravenous, subcutaneous, intramuscular, transmuscular, topical, or oral routes. For subcutaneous administration, for example, the dosage form consists of feline CD80, CD86, CD28 or CTLA-4 in sterile physiological saline. For oral or respiratory administration, feline CD80, CD86, CD28 or CTLA-4 , with or without excipients, is micro- or macro-encapsulated in, e.g., liposomes and microspheres. Dermal patches (or other slow-release dosage forms) are also be used.

MATERIALS AND METHODS

Preparation of raccoonpox virus stock samples.

Raccoonpox virus(RPV) isolate ATCC VR-838 was used for preparation of raccoonpox virus stock samples and raccoonpox virus genomic DNA. Another RPV isolate available is V71-I-85A from Center for Disease Control (CDC; Atlanta, Ga.). Raccoonpox virus (RPV) samples were prepared by infecting VERO cells, CRFK cells or MDCK cells at a multiplicity of infection of 0.01 PFU/cell in Dulbecco's Modified Eagle's Medium containing 2 mM glutamine, 100 units/ml penicillin, 100 units/ml streptomycin (these components were obtained from Sigma or equivalent supplier, and hereafter are referred to as DMEM negative medium). Prior to infection, the cell monolayers were washed once with DMEM negative medium to remove traces of fetal bovine serum. The RPV contained in the initial inoculum (0.5 ml for 10 cm plate; 10 ml for T225 cm flask) was then allowed to absorb onto the cell monolayer for two hours, being redistributed every half hour. After this period, the original inoculum was brought up to the recommended volume with the addition of complete DMEM medium (DMEM negative medium plus 5% fetal bovine serum). The plates were incubated at 37° C. in 5% $CO_2$ until cytopathic effect was complete. The medium and cells were harvested and frozen in a 50 ml conical screw cap tube at −70° C. Upon thawing at 37° C., the virus stock was aliquoted into 1.0 ml vials and refrozen at −70° C. The titers were usually about $10^6$ PFU/ml.

Preparation of swinepox virus stock samples.

Swinepox virus (SPV) samples were prepared by infecting embryonic swine kidney (EMSK) cells, ESK-4 cells, PK-15 cells or Vero cells at a multiplicity of infection of 0.01 PFU/cell in a 1:1 mixture of Iscove's Modified Dulbecco's Medium (IMDM) and RPMI 1640 medium containing 2 mM glutamine, 100 units/ml penicillin, 100 units/ml streptomycin (these components were obtained from Sigma or equivalent supplier, and hereafter are referred to as EMSK negative medium) Prior to infection, the cell monolayers were washed once with EMSK negative medium to remove traces of fetal bovine serum. The SPV contained in the initial inoculum (0.5 ml for 10 cm plate; 10 ml for T175 cm flask) was then allowed to absorb onto the cell monolayer for two hours, being redistributed every half hour. After this period, the original inoculum was brought up to the recommended volume with the addition of complete EMSK medium (EMSK negative medium plus 5% fetal bovine serum). The plates were incubated at 37° C. in 5% $CO_2$ until cytopathic effect was complete. The medium and cells were harvested and frozen in a 50 ml conical screw cap tube at −70° C. Upon thawing at 37° C., the virus stock was aliquoted into 1.0 ml vials and refrozen at −70° C. The titers were usually about $10^6$ PFU/ml.

PREPARATION OF RPV OR SPV DNA. For raccoonpox virus or swinepoxvirus DNA isolation, a confluent monolayer of VERO cells (for RPV) or EMSK cells (for SPV) in a T225 $cm^2$ flask was infected at a multiplicity of 0.1 with raccoonpox virus (ATCC VR-838) and incubated 3–5 days until the cells were showing 100% cytopathic effect. The infected cells were then harvested by scraping the cells into the medium and centrifuging at 3000 rpm for 5 minutes in a clinical centrifuge. The medium was decanted, and the cell pellet was gently resuspended in 1.0 ml Phosphate Buffer Saline (PBS: 1. 5 g $Na_2$–$PO_4$, 0.2 g $KH_2PO_4$, 0.8 g NaCL and 0.2 g Kcl per liter $H_2O$) (per T175) and subjected to two successive freeze-thaws (−70° C. to 37° C.). Upon the last thaw, the cells (on ice) were sonicated two times for 30 seconds each with 45 seconds cooling time in between. Cellular debris was then removed by centrifuging (Sorvall RC-5B superspeed centrifuge) at 3000 rpm for 5 minutes in a HB4 rotor at 4° C. RPV virions, present in the supernatant, were then pelleted by centrifugation at 15,000 rpm for 20 minutes at 4° C. in a SS34 rotor (Sorvall) and resuspended in 10 mM Tris (pH 7.5). This fraction was then layered onto a 36% sucrose gradient (w/v in 10 mM Tris pH 7.5) and centrifuged (Beckman L8–70M Ultracentrifuge) at 18,000 rpm for 60 minutes in a SW41 rotor (Beckman) at 4° C. The virion pellet was resuspended in 1.0 ml of 10 mM Tris pH 7.5 and sonicated on ice for 30 seconds. This fraction was layered onto a 20% to 50% continuous sucrose gradient and centrifuged 16,000 rpm for 60 minutes in a SW41 rotor at 4° C. The RPV virion band located about three quarters down the gradient was harvested, diluted with 20% sucrose and pelleted by centrifugation at 18,000 rpm for 60 minutes in a SW41 rotor at 4° C. The resultant pellet was then washed once with 10 mM Tris pH 7.5 to remove traces of sucrose and finally resuspended in 10 mM Tris pH 7.5. RPV DNA was then extracted from the purified virions by lysis (4 hours at 60° C.) induced by the addition of EDTA, SDS, and proteinase K to final concentrations of 20 mM, 0.5% and 0.5 mg/ml, respectively. After digestion, three phenol:chloroform (1:1) extractions were conducted and the sample precipitated by the addition of two volumes of absolute ethanol and incubation at −20° C. for 30 minutes. The sample was then centrifuged in an Eppendorf minifuge for 5 minutes at full speed. The supernatant was decanted, and the pellet air dried and rehydrated in 0.01 M Tris pH 7.5, 1 mM EDTA at 4° C.

Preparation of FHV virus stock samples

S-FHV-000 was obtained from the ATCC (ATCC No. 636) and S-FHV-001 was obtained from the NVSL (NVSL Challenge Virus Strain SGE, Lot KS). FHV virus stock samples were prepared by infecting Crandell Feline Kidney (CRFK) cells at a multiplicity of infection of 1.0 PFU/cell in Dulbecco's Modified Eagle Medium (DMEM) containing 2 mM glutamine, 100 units/ml penicillin, 100 units/ml streptomycin (these components were obtained from Irvine Scientific or equivalent supplier, and hereafter are referred to as complete DME medium) plus 5% fetal bovine serum. After cytopathic effect was complete, the medium and cells were harvested, aliquoted and frozen at −70° C. The titers were approximately $1\times10^7$ to $1\times10^8$ PFU/ml.

Preparation of herpesvirus DNA:

A confluent monolayer of CRFK cells in a 25 $cm^2$ flask or 60 mm petri dish was infected with 100 ml of virus sample. After overnight incubation, or when the cells were showing 100% cytopathic effect, the cells were scraped into the medium. The cells and medium were centrifuged at 3000 rpm for 5 minutes in a clinical centrifuge. The medium was decanted, and the cell pellet was gently resuspended in 0.5 ml solution containing 0.5% NONIDET P-40® (octyl phenol ethylene oxide condensate containing an average of 9 moles of ethylene oxide per molecule) (NP-40®, purchased from Sigma Chemical Co., St. Louis, Mo.). The sample was incubated at room temperature for 10 minutes. Ten ml of a stock solution of RNase A (Sigma Chemical Co., St. Louis, Mo.) were added (stock was 10 mg/ml, boiled for 10 minutes to inactivate DNAse). The sample was centrifuged to pellet nuclei. The DNA pellet was removed with a pasteur pipette or wooden stick and discarded. The supernatant fluid was decanted into a 1.5 ml Eppendorf tube containing 25 ml of 20% sodium dodecyl sulfate (Sigma) and 25 ml proteinase-K (10 mg/ml; Boehringer Mannheim Biochemicals, Indianapolis, Ind.). The sample was mixed and incubated at 37° C. for 30–60 minutes. An equal volume of water-saturated phenol was added and the sample was mixed briefly. The sample was centrifuged in an Eppendorf minifuge for 5 minutes at full speed. The upper aqueous phase was removed to a new Eppendorf tube, and two volumes of absolute ethanol were added and the tube put at −20° C. for 30 minutes to precipitate nucleic acid. The sample was centrifuged in an Eppendorf minifuge for 5 minutes. The supernatant was decanted, and the pellet was air dried and rehydrated in ~16 ml $H_2O$. For the preparation of larger amounts of DNA, the procedure was scaled up to start with roller bottles or 175 $cm^2$ flasks of CRFK cells. The DNA was stored in 0.01 M Tris pH 7.5, 1 mM EDTA at 4° C.

DNA transfection for generating recombinant virus

The method is based upon the calcium phosphate procedure of Graham and Van der eb [25] with the following modifications. Virus and/or Plasmid DNA were diluted to 298 ml in 0.01 M Tris pH 7.5, mM EDTA. Forty ml 2 M $CaCl_2$ was added followed by an equal volume of 2× HEPES buffered saline (10 g N-2-hydroxyethyl piperazine N'-2-ethanesulfonic acid (HEPES), 16 g NaCl, 0.74 g Kcl, 0.25 g $Na_2HPO_4.2H_2O$, 2 g dextrose per liter $H_2O$ and buffered with NaOH to pH 7.4). The mixture was then incubated on ice for 10 minutes, and then added dropwise to an 80% confluent monolayer of CRFK cells growing in a 60 mm petri dish under 5 ml of medium (DME plus 5% fetal bovine serum). The cells were incubated 4 hours at 37° C. in a humidified incubator containing 5% $CO_2$. Media on the plates were aspirated, and cells were treated with 20% glycerol in 1XPBS (1.15 g $Na_2HPO_4$, 0.2 g $KH_2PO_4$, 0.8 g NaCl, 0.2 g Kcl per liter $H_2O$) for one minute. The cells were washed three times with 5 ml of 1XPBS and then fed with 5ml of medium (DME plus 5% fetal bovine serum). The cells were incubated at 37° C. as above for 3–7 days until cytopathic effect from the virus was 50–100%. Virus was harvested as described above for the preparation of virus stocks. This stock was referred to as a transfection stock and was subsequently screened for recombinant virus by the SCREEN FOR RECOMBINANT HERPESVIRUS EXPRESSING ENZYMATIC MARKER GENES.

PREPARATION OF INFECTED CELL LYSATES. For cell lysate preparation, serum free medium was used. A confluent monolayer of cells (VERO, CRFK, or MDCK) in a 25 $cm^2$ flask or a 60 mm petri dish was infected with 100 μl of virus sample. After cytopathic effect was complete, the medium and cells were harvested and the cells were pelleted at 3000 rpm for 5 minutes in a clinical centrifuge. The cell pellet was resuspended in 250 μl of disruption buffer (2% sodium dodecyl sulfate, 2% β-mercapto-ethanol). The samples were sonicated for 30 seconds on ice and stored at −20% C.

WESTERN BLOTTING PROCEDURE. Samples of lysates and protein standards were run on a polyacrylamide gel according to the procedure of Laemnli. After gel electrophoresis the proteins were transferred and processed according to Sambrook et al. (1989). The primary antibody was diluted 1:100 with 5% non-fat dry milk in Tris-sodium chloride, and sodium Azide (TSA: 6.61 g Tris-HCl, 0.97 g Tris-base, 9.0 g NaCl and 2.0 g Sodium Azide per liter $H_2O$). The secondary antibody was alkaline phosphatase conjugated and diluted 1:1000 with TSA.

MOLECULAR BIOLOGICAL TECHNIQUES. Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Sambrook et al. (1989) and *Current Protocols in Molecular Biology* (1992). Except as noted, these were used with minor variation.

DNA SEQUENCING. DNA sequencing was performed by fluorescent labelled dideoxy sequencing reactions using ABI PRISM Dye Terminator Cycle Sequencing Ready Reaction Kit with Amplitaq DNA polymerase, FS (Perkin-Elmer; per manufacturer's instructions) and electrophoresed on an Perkin-Elmer/Applied Biosystems automated DNA sequencer Model 373A according to manufacturer's instructions. Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using DNAStar software.

CLONING WITH THE POLYMERASE CHAIN REACTION. The polymerase chain reaction (PCR) was used to introduce restriction sites convenient for the manipulation of various DNAs. The procedures used are described by Innis, et al. (1990). In general, amplified fragments were less than 500 base pairs in size and critical regions of amplified fragments were confirmed by DNA sequencing. The primers used in each case are detailed in the descriptions of the construction of homology vectors below.

HOMOLOGOUS RECOMBINATION PROCEDURE FOR GENERATING RECOMBINANT RPV, SPV or FHV. This method relies upon the homologous recombination between the raccoonpox virus DNA and the plasmid homology vector DNA which occurs in the tissue culture cells containing both raccoonpox virus DNA and transfected plasmid homology vector. For homologous recombination to occur, the monolayers of cells (CRFK, MDCK, or VERO) are infected with S-RPV-000 (ATCC VR-838) or S-SPV-001 or S-FHV-001 at a multiplicity of infection of 0.01 PFU/cell to introduce replicating RPV (i.e. DNA synthesis) into the cells. The plasmid homology vector DNA is then transfected into these cells according to the INFECTION-TRANSFECTION PROCEDURE. The construction of homology vectors used in this procedure is described below INFECTION-TRANSFECTION PROCEDURE. 6 cm plates of cells (CRFK, MDCK, or VERO) about 80% confluent were infected with S-RPV-000 or S-SPV-001 or S-FHV-001 at a multiplicity of infection of 0.01 PFU/cell in DMEM negative medium and incubated at 37° C. in a humidified 5% $CO_2$ environment for 2–3 hours. The transfection procedure used is essentially that recommended for Lipofectin™ Reagent (BRL). Briefly, for each 6 cm plate, 15 μg of plasmid DNA was diluted up to 100 μl with $H_2O$. Separately, 50 micrograms of Lipofectin Reagent was diluted to 100 μl with $H_2O$. The 100 μl of diluted Lipofectin Reagent was then added dropwise to the diluted plasmid DNA contained in a polystyrene 5 ml snap cap tube and mixed gently. The mixture was then incubated for 15–20 minutes at room temperature. During this time, the virus inoculum was removed from the 6 cm plates and the cell monolayers washed once with DMEM negative medium. Three ml of DMEM negative medium was then added to the plasmid DNA/lipofectin mixture and the contents pipetted onto the cell monolayer. The cells were incubated overnight (about 16 hours) at 37° C. in a humidified 5% $CO_2$ environment. The next day the 3 ml of DMEM negative medium was removed and replaced with 5 ml DMEM complete medium. The cells were incubated at 37° C. in 5% $CO_2$ for 3–5 days until cytopathic effect from the virus was 80–100%. Virus was harvested as described above for the preparation of virus stocks. This stock was referred to as a transfection stock and was subsequently screened for recombinant virus by the BLUOGAL SCREEN FOR RECOMBINANT RACCOONPOX VIRUS OR CPRG SCREEN FOR RECOMBINANT RACCOONPOX VIRUS.

SCREEN FOR RECOMBINANT RPV OR SPV OR FHV EXPRESSING β-galactosidase (BLUOGAL AND CPRG ASSAYS) or β-glucuronidase (X-GLUC ASSAY). When the *E. coli* β-galactosidase lacZ) marker gene was incorporated into a recombinant virus the plaques containing the recombinants were visualized by one of two simple methods. In the first method, the chemical Bluogal™ (Life Sciences Technology, Bethesda, Md.) was incorporated (200 μg/ml) into the agarose overlay during the plaque assay, and plaques expressing active β-galactosidase turned blue. The blue plaques were then picked onto fresh cells (MDCK, CRFK or VERO) and purified by further blue plaque isolation. In the second method, CPRG (Boehringer Mannheim) was incorporated (400 μg/ml) into the agarose overlay during the plaque assay, and plaques expressing active β-galactosidase turned red. The red plaques were then picked onto fresh cells (MDCK, CRFK or VERO) and purified by further red plaque isolation. In both cases viruses were typically purified with three to four rounds of plaque purification.

When the *E. coli* β-glucuronidase (uidA) marker gene was incorporated into a recombinant virus the plaques containing the recombinants were visualized by using the chromogenic substrate, X-beta-D-gluUA CHX (X-GLUC; 5-Bromo-4-chloro-3-indoxyl-beta-D-glucuronic acid, cyclohexylammonium salt; Biosynth AG; Switzerland) was incorporated (200 μg/ml) into the agarose overlay during the plaque assay, and plaques expressing active β-glucuronidase turned blue. The blue plaques were then picked onto fresh cells (MDCK, CRFK or VERO) and purified by further blue plaque isolation.

SCREEN FOR FOREIGN GENE EXPRESSION IN RECOMBINANT RPV USING BLACK PLAQUE ASSAYS. To analyze expression of foreign antigens expressed by recombinant raccoonpox viruses, monolayers of cells (MDCK, CRFK or VERO) were infected with recombinant RPV or SPV or FHV, overlayed with nutrient agarose media and incubated for 3–5 days at 37° C. for plaque development to occur. The agarose overlay was then removed from the dish, the cells fixed with 100% methanol for 10 minutes at room temperature and the cells air dried. Fixation of the cells results in cytoplasmic antigen as well as surface antigen detection whereas specific surface antigen expression can be detected using non-fixed cells. The primary antibody was then diluted to the appropriate dilution with 1× blotto (5% non-fat dry milk in Tris-sodium chloride, and sodium Azide (TSA: 6.6 g Tris-HCl, 0.97 g Tris-base, 9.0 g NaCl and 2.0 g Sodium Azide per liter $H_2O$) and incubated on the cell monolayer for 2 hours at room temperature. Unbound antibody was then removed by washing the cells three times with TS buffer at room temperature. The secondary antibody, a alkaline-phosphatase conjugate, was diluted 1:1000 with 1× blotto and incubated with the cells for 2 hours at room temperature. Unbound secondary antibody was then removed by washing the cells three times with TS buffer (6.61 g Tris-HCl, 0.97 g Tris-base, 9.0 g NaCl per liter $H_2O$) at room temperature. The cells were then incubated 15–30 minutes at room temperature with freshly prepared substrate solution (100 mM Tris HCl pH. 9.5, 100 mM NaCl, 5 mM $MgCl_2$, 0.3 mg/ml Nitro Blue Tetrazolium and 0.15 mg/ml 5-Bromo-4-chloro-3-Indoyl Phosphatase). Plaques expressing the correct antigen stain black. A fixer solution (20 mM Tris-HCl pH 2.9 and 1 mM EDTA) was used to stop the color development reaction.

SCREEN FOR FELINE CD80 (B7-1) and CD86 (B7-2) EXPRESSION IN RECOMBINANT SPV, RPV or FHV USING BLACK PLAQUE ASSAYS. To analyze expression of CD80 or CD86 costimulatory molecules expressed by recombinant swinepox viruses, raccoonpox or feline herpesvirus on monolayers of cells (MDCK, CRFK, VERO or ESK-4) were infected with recombinant RPV or SPV or FHV viruses expressing CD80 or CD86, overlaid with nutrient agarose media and incubated for 3–5 days at 37° C. for plaque development to occur. The agarose overlay was then removed from the dish, the cells were either fixed with 100% methanol for 10 minutes at room temperature and the cells air dried or left unfixed or left unfixed and treated immediately with 1× PBS. Fixation of the cells results in cytoplasmic antigen as well as surface antigen detection whereas specific surface antigen expression can be detected using non-fixed cells. A huCTLA-4/Fc chimera (R&D Systems, Minn. MN, cat. #325-CT) was then diluted to the appropriate dilution with 1× blotto (5% non-fat dry milk in Tris-sodium chloride (TS: 6.61 g Tris-HCl, 0.97 g Tris-base, 9.0 g NaCl per liter $H_2O$) and incubated on the cell monolayer for 2 hours at room temperature. Unbound chimera was then removed by washing the cells three times with TS buffer at room temperature. The detection antibody, a monoclonal anti-huIgG1 fc alkaline-phosphatase conjugate (Zymed, cat. 05-3322) was diluted to the appropriate concentration with 1× blotto and incubated with the cells for 2 hours at room temperature. Unbound detection antibody was then removed by washing the cells three times with TS buffer (6.61 g Tris-HCl, 0.97 g Tris-base, 9.0 g NaCl per liter $H_2O$) at room temperature. The cells were then incubated 15–30 minutes at room temperature with freshly prepared substrate solution (100 mM Tris HCl pH. 9.5, 100 mM NaCl, 5 mM $MgCl_2$, 0.3 mg/ml Nitro Blue Tetrazolium and 0.15 mg/ml 5-Bromo-4-chloro-3- Indoyl Phosphatase). Plaques expressing CD80 or CD86 stain black. A fixer solution (20 mM Tris-HCl pH 2.9 and 1 mM EDTA) was used to stop the color development reaction.

SCREEN FOR FELINE INTERFERON GAMMA BIOACTIVITY EXPRESSED FROM RECOMBINANT SPV, RPV or FHV USING VSV PLAQUE REDUCTION.

CRFKS or an appropriate feline cell line in 96 well plates were treated with supernatants from cells infected with recombinant viruses expressing feline IFNgamma and incubated for 6–12 hours at 37C. VSV virus (100–1000 particles/well) was then added to the appropriate wells and incubated for 24 hours or until control wells with cells only, were completely lysed. The wells were washed with 1× PBS 3 times and monolayers were fixed with 100% methanol and air dried. A 0.05% solution of Crystal violet was added to all wells for 10 minutes at room temperature, then air dried. Wells were scored for the presence of purple staining. A healthy, in tact, monolayer of cells will take up the crystal violet dye. Supernatants with IFN gamma activity will protect CRFKs from VSV induced cell lysis, and stain purple.

PROCEDURE FOR PURIFICATION OF VIRAL GLYCOPROTEINS FOR USE AS DIAGNOSTICS. Viral glycoproteins are purified using antibody affinity columns. To produce monoclonal antibodies, 8 to 10 week old BALB/c female mice are vaccinated intraperitoneally seven times at two to four week intervals with $10^7$ PFU of raccoonpox virus recombinants. Three weeks after the last vaccination, mice are injected intraperitoneally with 40 mg of the corresponding viral glycoprotein. Spleens are removed from the mice three days after the last antigen dose.

Splenocytes are fused with mouse NS1/Ag4 plasmacytoma cells by the procedure modified from Oi and Herzenberg. Splenocytes and plasmacytoma cells are pelleted together by centrifugation at 300 ×g for 10 minutes. One ml of a 50% solution of polyethylene glycol (m.w. 1300–1600) is added to the cell pellet with stirring over one minute. Dulbecco's modified Eagles's medium (5ml) is added to the cells over three minutes. Cells are pelleted by centrifugation at 300 ×g for 10 minutes and resuspended in medium with 10% fetal bovine serum and containing 100 mM hypoxanthine, 0.4 mM aminopterin and 16 mM thymidine (HAT). Cells (100 ml) are added to the wells of eight to ten 96-well tissue culture plates containing 100 ml of normal spleen feeder layer cells and incubated at 37° C. Cells are fed with fresh HAT medium every three to four days.

Hybridoma culture supernatants are tested by the ELISA ASSAY in 96-well microtiter plates coated with 100 ng of viral glycoprotein. Supernatants from reactive hybridomas are further analyzed by black-plaque assay and by Western Blot. Selected hybridomas are cloned twice by limiting dilution. Ascetic fluid is produced by intraperitoneal injection of $5\times10^6$ hybridoma cells into pristane-treated BALB/c mice.

Cell lysates from raccoonpox virus recombinants are obtained as described in PREPARATION OF INFECTED CELL LYSATES. The glycoprotein-containing cell lysates (100 mls) are passed through a 2-ml agarose affinity resin to which 20 mg of glycoprotein monoclonal antibody has been immobilized according to manufacturer's instructions (AFC Medium, New Brunswick Scientific, Edison, N.J.). The column is washed with 100 ml of 0.1% Nonidet P-40 in phosphate-buffered saline (PBS) to remove nonspecifically bound material. Bound glycoprotein is eluted with 100 mM carbonate buffer, pH 10.6 (40).

Pre- and posteluted fractions are monitored for purity by reactivity to the RPV monoclonal antibodies in an ELISA system.

ELISA ASSAY. A standard enzyme-linked immunosorbent assay (ELISA) protocol is used to determine the immune status of the animal following vaccination and challenge. A glycoprotein antigen solution (100 ml at ng/ml in PBS) is allowed to absorb to the wells of microtiter dishes for 18 hours at 4° C. The coated wells are rinsed one time with PBS. Wells are blocked by adding 250 ml of PBS containing 1% BSA (Sigma) and incubating 1 hour at 37° C. The blocked wells are rinsed one time with PBS containing 0.02% Tween 20. 50 ml of test serum (previously diluted 1:2 in PBS containing 1% BSA) are added to the wells and incubated 1 hour at 37° C. The antiserum is removed and the wells are washed 3 times with PBS containing 0.02% Tween 20. 50 ml of a solution containing anti-bovine IgG coupled to horseradish peroxidase (diluted 1:500 in PBS containing 1% BSA, Kirkegaard and Perry Laboratories, Inc.) is added to visualize the wells containing antibody against the specific antigen. The solution is incubated 1 hour at 37° C., then removed and the wells are washed 3 times with PBS containing 0.02% Tween 20. 100 ml of substrate solution (ATBS, Kirkegaard and Perry Laboratories, Inc.) are added to each well and color is allowed to develop for 15 minutes. The reaction is terminated by addition of 0.1M oxalic acid. The color is read at absorbance 410 nm on an automatic plate reader.

STRATEGY FOR THE CONSTRUCTION OF SYNTHETIC POX VIRAL PROMOTERS. For recombinant swinepox vectors synthetic pox promoters offer several advantages including the ability to control the strength and timing of foreign gene expression. Three promoter cassettes LP1, EP1 and LP2 based on promoters that have been defined in the vaccinia virus were designed. Each cassette was designed to contain the DNA sequences defined in vaccinia flanked by restriction sites which could be used to combine the cassettes in any order or combination. Initiator methionines were also designed into each cassette such that inframe fusions could be made at either EcoRI or BamHI sites. A set of translational stop codons in all three reading frames and an early transcriptional termination signal were also engineered downstream of the inframe fusion site. DNA encoding each cassette was synthesized according to standard techniques and cloned into the appropriate homology vectors.

Isolation of an Initial Fragment of CD80 mRNA was extracted from peripheral blood mononuclear cells (PBMC) stimulated for 16 hr with Con A using the RNAzolB RNA extraction reagent (Biotexc, Houston, Tex.). Initially, cDNA was derived from this RNA by a reverse transcriptase (RT) reaction employing oligo dT as the 3' primer. Briefly, the RNA and oligo dT were heated to 75° C. for 3 min to remove secondary structure. The RT, dNTP, buffer and distilled water were then added and the mixture incubated for 1 hr at 42° C. Following this incubation the sample was heated to 95° C. for 5 min to inactivate the RT. Degenerate primers derived from consensus regions within the human and murine CD80 published sequences (GeneBank, Gaithersburg, Mass.) were then employed for the initial amplification of a 344 nucleotide (ntd.) fragment encoding a central region within the constant domain of the gene:

5' primer B7-2 GGC CCG AGT A(CT)A AGA ACC GGA C (SEQ ID NO 56)

3' primer B7-3 CAG (AT)TT CAG GAT C(CT)T GGG AAA (CT)TG (SEQ ID NO 57)

A hot start polymerase chain reaction (PCR) protocol employing Taq polymerase was used to amplify the product. The reaction mixture, lacking the Taq enzyme, was initially heated to 95° C. for 5 min, in a hot start step, to prevent the formation of primer dimers. The enzyme was added prior to the initiation of the temperature cycle. The PCR reaction was then heated to 95° C. for 30 sec to melt the double stranded DNA. The reaction was then cooled to 42° C. for 30 sec to facilitate the annealing of the degenerate primers. A low annealing temperature was employed to facilitate the binding of primers that were not 100% homologous. The reaction was then heated to 72° C. for 45 sec, the optimal temperature for the Taq polymerase to extend the primer and copy the opposing DNA strand. The temperature cycle was repeated 30 times. Following the 30 cycles, a final extension step of 72° C. for 7 min was used to facilitate extension of any uncompleted products. After visualization on a 1% agarose gel, the product was ligated overnight at 16° C. into the TA cloning vector (InVitrogen, San Diego, Calif.) for sequencing. Two ml of the ligation reaction was used to transform competent InvaF' cells. The transformed bacteria were streaked onto LB plates (50 mg/ml ampicillin) coated with 40 ml of a 50 mg/ml solution of x- gal. The following day, white colonies were selected and inoculated into 5 ml of LB media containing 100 mg/ml of ampicillin and grown overnight at 37° C. with shaking at 225 rpm.

Mini-preps were performed on overnight cultures to determine clones that possessed the plasmid with the correct insert. Plasmid was extracted from the cultures using a standard alkaline lysis procedure, with the DNA being further purified by phenol:chloroform extraction (Maniatis et al., 1982). The DNA was precipitated in 2 volumes of ethanol and then digested with EcoRI. The digests were visualized on a 1% agarose gel to determine colonies with plasmid that contained the proper insert. Plasmid was then purified from positive clones and sequenced using either Sequenase based (USB, Cleveland, Ohio) $S^{35}$ radiolabeled dideoxy terminator sequencing or by fluorescent dye terminator cycle sequencing (Perkin Elmer, Norwalk Conn.). From the sequence of the cDNA, specific 3' and 5' primers were constructed for use in 5' rapid amplification of cDNA ends (RACE) reactions and for derivation of the 3' sequence in conjunction with degenerate primers from the 3' untranslated region (UTR).

Isolation of the 5' Region of CD80

The Marathon cDNA amplification protocol (Clonetech, Palo Alto, Calif.) was used to derive the 5' sequence of the gene. mRNA was produced from PBMC stimulated for 12 hr with Con A and concurrently 4 hr with LPS. The mRNA was extracted using the ULTRASPEC RNA extraction reagent (Biotexc, Houston Tex.). cDNA was produced with an anchor oligo dT primer with degenerate nucleotides at the 5' end to facilitate binding of the primer to the 5' most end of the poly A tail. cDNA was then transcribed as previously described. Specific linkers were ligated to the cDNA with T4 DNA ligase. Touchdown PCR was performed on the cDNA with an internal 3' primer specific for the region amplified previously:

```
B7-284: TTA TAC TAG GGA CAG GGA AG (SEQ ID NO 58)

B7-190: AGG CTT TGG AAA ACC TCC AG (SEQ ID NO 59)
```

and an anchor primer complementary to the ligated linker sequence. The parameters for the touchdown PCR reaction using the KlenTaq polymerase mix (Clontech, Palo Alto, Calif.) were: 95° C. for 5 min 1 cycle; 95C° C. for 30 sec, 72° C. for 30 sec and 68° C. for 45 sec 5 cycles; 95° C. for 30 sec, 65° C. for 30 sec and 68° C. for 45 sec 5 cycles; 95° C. for 30 sec, 60° C. for 30 sec and 68° C. for 45 sec 25 cycles. 1 ml of this reaction was diluted in 50 ml of water and 5 ml of this dilution were then used in a nested PCR reaction (95° C. for 5 min 1 cycle; 95° C. for 30 sec, 65° C. for 30 sec and 68° C. for 45 sec 30 cycles with KlenTaq polymerase mix) with the linker specific anchor primer and a gene specific 3' primer located 5' of the initial primer (FIG. 6).

```
                                      (SEQ ID NO 60)
B7-20:   TTG TTA TCG GTG ACG TCA GTG

                                      (SEQ ID NO 61)
B7-135: CAA TAA CAT CAC CGA AGT CAG G
```

20 ml of each reaction was visualized on a 1.5% agarose gel and the proper fragment cut out of the gel. The cDNA was extracted and purified from the agarose by centrifuging the gel slice through a gel nebulizer and micropure 0.22 mm filter (Amicon, Beverly, Mass.). The purified DNA was then sequenced directly using dye terminator cycle sequencing (Perkin Elmer, Norwalk, Conn.).

Isolation of the 3' Region of CD80

The 3' region of the gene was derived by choosing 5 gene specific primers from the 344 ntd. fragment and the 5' region previously sequenced:

```
                                      (SEQ ID NO 62)
B7-s220 GTC ATG TCT GGC AAA GTA CAA G

                                      (SEQ ID NO 63)
B7-50   CAC TGA CGT CAC CGA TAA CCA C
```

-continued

```
                                   (SEQ ID NO 64)
B7-140  CTG ACT TCG GTG ATG TTA TTG G

                                   (SEQ ID NO 65)
B7-550: GCC ATC AAC ACA ACA GTT TCC

                                   (SEQ ID NO 66)
B7-620: TAT GAC AAA CAA CCA TAG CTT C
```

Degenerate 3' primers were then chosen from concensus regions of the human and murine CD80 3' UTR.

```
                                   (SEQ ID NO 67)
B7-1281 G(A/G)A AGA (A/T)TG CCT CAT GA(G/T) CC

                                   (SEQ ID NO 68)
B7-1260 CA(C/T) (A/G)AT CCA ACA TAG GG
```

cDNA was produced from RNA extracted with ULTRASPEC (Biotexc, Houston, Tex.) from PBMC stimulated with Con A and LPS as previously described.

The anchored oligo dT was used as the initial 3' primer for RNA transcription to cDNA. Taq polymerase based PCR reactions were performed with this cDNA using the specific 5' primers and degenerate 3' primers (95° C. for 5 min 1 cycle; 95° C. for 30 sec, 42° C. for 30 sec and 72° C. for 45 sec 30 cycles; 72° C. for 7 min).

Two rounds of nested reactions were required before a single fragment of the right size was produced. This product was cut from a 1.5% agarose gel, purified as previously described, and sequenced with dye terminator cycle sequencing ( Perkin lElmer, Norwalk, Conn.).

From the sequence data of the 5' and 3' regions, primers were constructed that would amplify a region encoding the entire open reading frame of the feline CD80 gene:

```
B7 START: ATG GGT CAC GCA GCA AAG TGG       (SEQ ID NO 69)

B7-960:   CCT ACT ACA GAA GAG CTA AAG AGG C  (SEQ ID NO 70)
```

PBMC cDNA produced previously and known to contain DNA encoding the gene was employed. This PCR reaction (95° C. for 5 min 1 cycle; 95° C. for 30 sec, 42° C. for 30 sec and 72° C. for 45 sec 30 cycles; 72° C. for 7 min) employed KlenTaq DNA polymerase, an enzyme cocktail that retains some 5' exonuclease activity in the hopes of reducing random errors often associated with Taq polymerase. The reaction amplified a 960 base pair (bp) fragment which was cloned into the TA cloning vector (InVitrogen, San Diego, Calif.) and sequenced as previously described. The final sequence of the gene included cDNA from two separate animals. Each base pair of the gene was independently verified in at least three separate sequences derived from individual PCR reactions, to reduce the possibility of errors derived from PCR induced mistakes.

Isolation of an initial fragment of CD28 mRNA was extracted from HK5 peripheral blood lymphocytes stimulated for 16 hr with Con A using the RNAzolB RNA extraction reagent (Biotexc, Houston, Tex.). Initially cDNA was derived from this RNA by a reverse transcriptase (RT) reaction employing oligo dT as the 3' primer. Briefly, the RNA, and oligo dT were heated to 75° C. for 3 min to remove secondary structure. The RT, dNTP, buffer and distilled water were then added and the mixture incubated for 1 hr at 42° C. Following this incubation, the sample was heated to 95° C. for 5 min to inactivate the RT. Degenerate primers derived from consensus regions found within the human, murine and rabbit CD28 published nucleic acid sequences (GeneBank, Bethesda, Md.) were then employed for the initial amplification of a 673 ntd fragment encoding the majority of the open reading frame.

```
                                      (SEQ ID NO 71)
CD28-113: CAA CCT TAG CTG CAA GTA CAC

                                      (SEQ ID NO 72)
CD28-768: GGC TTC TGG ATA GGG ATA GG
```

A hot start PCR protocol employing Taq polymerase was used to amplify the product (95° C. for 5 min 1 cycle; 95° C. for 30 sec, 48° C. for 30 sec and 72° C. for 45 sec, 30 cycles; 72° C. for 7 min, 1 cycle). The fragment was then visualized on a 1% agarose gel and ligated into the TA cloning vector (InVitrogen, San Diego, Calif.) and sequenced as previously described. From the sequence of the cDNA, specific 3' primers were derived and synthesized for use in 5' RACE reactions.

```
                                      (SEQ ID NO 73)
CD28190:  CGG AGG TAG AAT TGC ACT GTC C

                                      (SEQ ID NO 74)
CD28 239: ATT TTG CAG AAG TAA ATA TCC
```

Isolation of the 5' Region of CD28

A modified GIBCO 5' RACE protocol (Gibco BRL, Gaithersburg, Md.) was employed to obtain the remaining 5' sequence of the feline CD28 molecule. RNA was extracted from 16 hr Con A stimulated PBMC. A 3' gene specific primer was employed for first strand cDNA synthesis. The RNA and the primer were heated to 75° C. for 5 min prior to the addition of the other RT reagents. Following the denaturation, the mixture was cooled to 4° C. and reaction buffer, magnesium chloride, dNTP, DTT and SuperScript RT (Gibco BRL, Gaithersburg, Md.) were added. The RT mixture was incubated at 42° C. for 30 min and then heated to 70° C. for 15 min to denature the RT. An RNase cocktail was then added and the reaction incubated at 55° C. for 10 min to removal residual RNA and prevent incorrect terminal transferase (TdT) extension. The cDNA was then purified over a GlassMax (Gibco BRL, Gaithersburg, Md.) spin column to remove unincorporated DNTP and primer. Purified cDNA eluted from the column was then tailed with TdT. TdT was employed to add a 20–30 nucleotide dC tail to the cDNA. The enzyme was added to a mixture of purified cDNA, magnesium chloride, reaction buffer, and dCTP following denaturation of the cDNA at 95° C. for 3 min. The reaction was incubated at 37° C. for 10 min and the enzyme was then heat inactivated at 70° C. for an additional 10 min. The tailed cDNA was amplified in a Taq polymerase based hot start PCR reaction (95° C. for 5 min; 95° C. for 30 sec, 55° C. for 30 sec 72° C. for 45 sec, 35 cycles; 72° C. for 7 min). The primers for this reaction included a 3' primer located 5' of the cDNA synthesis primer, and an anchor primer specific for the dC linker and composed largely of dG with a few dI residues. One ml of this reaction was diluted in 50 ml of water and 5 ml of this dilution were then used in a nested PCR reaction (95° C. for 5 min 1 cycle; 95° C. for 30 sec, 55° C. for 30 sec and 72° C. for 45 sec 30 cycles with KlenTaq polymerase mix) with the dG/dI 5' anchor primer and an additional upstream gene specific 3' primer. Thirty ml of the nested reaction was then visualized on a 1.5% agarose gel, and the proper fragment extracted from the gel (FIG. 19). The cDNA was purified as previously described with the Amicon gel nebulizer and micropure filter (Amicon, Beverly, Mass.). The purified cDNA sample was sequenced through dye terminator cycle sequencing (Perkin Elmer, Norwalk, Conn.). From the fragments completed, a concensus sequence was derived. From the sequence, a primer pair was synthesized that encompassed the entire open reading frame of the feline CD28 gene:

```
feCD28 5': CGC GGA TCC ACC GGT AGC ACA ATG ATC CTC AGG (SEQ ID NO 75)

feCD28 3': CGC GGA TCC TCT GGA TAG GGG TCC ATG TCA G   (SEQ ID NO 76)
```

Using these primers, a cDNA molecule including the entire coding region was amplified from Con A stimulated EK6 and ED3 PBMC derived cDNA. This PBMC cDNA was produced previously and had been demonstrated to contain RNA encoding the gene. This PCR reaction (95° C. for 5 min 1 cycle; 95° C. for 30 sec, 42° C. for 30 sec and 72° C. for 45 sec 30 cycles; 72° C. for 7 min) using KlenTaq DNA polymerase in the hopes of reducing random errors often associated with Taq polymerase, produced a 754 bp fragment which was cloned into the TA cloning vector and sequenced as previously described. As with the CD80 molecule, each nucleotide site was confirmed by at least three independently derived sequences.

HOMOLOGY VECTOR 902-49.46. The plasmid 902-49.46 was constructed for the purpose of inserting foreign DNA into RPV. It incorporates an *E. coli* β-galactosidase (lacz) marker gene flanked by RPV DNA. Upstream of the foreign gene is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the β-galactosidase (lacZ) marker gene is under the control of a late promoter (LP1) and a second foreign DNA is inserted into an EcoRI or BamHI site, and the second foreign DNA is under the control of the late/early promoter (LP2EP2). It was constructed utilizing standard recombinant DNA techniques (Sambrook, et al.), by joining restriction fragments from the following sources with the synthetic DNA sequences. The plasmid vector was derived from an approximately 2999 base pair HindIII restriction fragment of pSP64 (Promega). Fragment 1 is an approximately 906 base pair HindIII to XbaI restriction sub-fragment of the RPV HindIII restriction fragment U (Knight et al.,). Fragment 2 is an approximately 3010 base pair BamHI to PvuII restriction fragment of plasmid pJF751 (Ferrari, et al.). Fragment 3 is an approximately 895 base pair XbaI to HindIII subfragment of the RPV HindIII fragment U. The XbaI sites in fragments 1 and 3 were converted to unique NotI sites using NotI linkers.

HOMOLOGY VECTOR 904-63.B7. The homology vector 904-63.B7 was used to insert foreign DNA into SPV. It incorporates an *E. coli* β-galactosidase(lacZ) marker gene and the feline immunodeficiency virus (FIV) gag/protease and envelope genes flanked by SPV DNA. When this homology vector was used according to the HOMOLOGOUS RECOMBINATION PROCEDURE FOR GENERATING RECOMBINANT SPV a virus containing DNA coding for the foreign genes results. Note that the β galactosidase (lacZ) marker gene is under the control of a synthetic late pox promoter (LP1) and the FIV gag/protease and envelope genes are under the control of separate, but identical synthetic late/early pox promoters (LP2EP2). The FIVgag/protease and FIV envelope promoter/gene cassettes are oriented in opposing directions such that transcription of the gag/protease and envelope genes runs toward each other to avoid the possibility of homologous recombination between identical promoters. The homology vector was constructed utilizing standard recombinant DNA techniques (Sambrook, et al.), by joining restriction fragments from the following sources with the appropriate synthetic DNA sequences. The plasmid vector was derived from an approximately 2972 base pair HindIII to BamHI restriction fragment of pSP64 (Promega). Fragment 1 is an approximately 1484 base pair BglII to AccI restriction sub-fragment of the SPV HindIII fragment M (23). Fragment 2 is an approximately 2580 base pair EcoRI to BglII fragment of the FIV envelope gene synthesized by reverse transcription (RT) and polymerase chain reaction (PCR) (15, 42) using cDNA from the FIV PPR strain. The upstream primer (5'-GCCCGGATCCTATGGCAGAAGGGTTTGCAGC-3 ' 10/93.21) (SEQ ID NO 77) synthesizes from the 5' end of the FIV envelope gene and introduces a BamHI site at the 5' end of the gene. The downstream primer was (5'-CCGTGGATCCGGCACTCCATCATTCCTCCTC-3'; 10/93.20) (SEQ ID NO 78) synthesizes from the 3' end of the FIV envelope gene, introduces an BamHI site at the 3' end of the gene, and was used for reverse transcription and polymerase chain reaction. The PCR product was digested with BamHI to yield a fragment 2580 base pairs in length corresponding to the FIV envelope gene. Fragment 3 is an approximately 1839 base pair EcoRI to BglII fragment of the FIV gag/protease gene synthesized by reverse transcription (RT) and polymerase chain reaction (PCR) (15, 42) using cDNA from the FIV PPR strain. The upstream primer (5'-GCGTGAATTCGGGGAATGGACAGGGGCGAGAT-3'; 11/94.9) (SEQ ID NO 79) synthesizes from the 5' end of the FIV gag/protease gene and introduces an EcoRI site at the 5' end of the gene. The downstream primer was (5'-GAGCCAGATCTGCTCTTTTTACTTTCCC-3'; 11/94.10) (SEQ ID NO 80) synthesizes from the 3' end of the FIV gag/protease gene, introduces an BglII site at the 3' end of the gene, and was used for reverse transcription and polymerase chain reaction. The PCR product was digested with EcoRI and BglII to yield a fragment approximately 1839 base pairs in length corresponding to the FIV gag/protease gene. Fragment 4 is an approximately 3010 base pair BamHI to PvuII restriction fragment of plasmid pJF751 (Ferrari, et al). Fragment 5 is an approximately 2149 base pair AccI to HindIII restriction sub-fragment of the SPV HindIII restriction fragment M. The AccI site in the SPV homology vector was converted to a unique NotI site using synthetic linkers.

HOMOLOGY VECTOR 917-60.B9. The plasmid 917-60.B9 was constructed for the purpose of inserting foreign DNA into SPV. It incorporates an *E. coli* β-galactosidase (lacZ) marker gene and the feline IFN-γ gene (Onions, et al., (1996); Argyle, et al., (1995)) flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase(lacZ) marker gene is under the control of a swinepox O1L promoter, and the feline CD28 gene is under the control of a synthetic late/early pox promoter (LP2EP2). It may be constructed utilizing standard recombinant DNA techniques (Sambrook, et al.), by joining restriction fragments from the following sources. The plasmid vector was derived from an approximately 2972 base pair HindIII to BamHI restriction fragment of pSP64 (Promega). Fragment 1 is an approximately 1484 base pair Bg1II to AccI restriction sub-fragment of the SPV HindIII restriction fragment M. Fragment 2 is an EcoRI to BamHI restriction fragment synthesized by reverse transcription and polymerase chain reaction (PCR) using RNA from ConA stimulated feline spleen cells as a template. To synthesize feline IFN-γ, the primer 5'-TCGAGAATTCGATGAATTACACAAGTTTTA TTTTCG-3'; 1/97.4) (SEQ ID NO 81) synthesized from the 5' end of the feline IFN-γ gene, introduced an EcoRI site at the 5' end of the gene. The primer (5'-TCGAGGATCCTTATTTCGATGCTCTACGGCCTC-3'; 1/97.3) (SEQ ID NO 82) was used for reverse transcription and PCR and synthesized from the 3' end of the feline IFN-γ gene, introduced a BamHI site at the 3' end of the gene. The PCR product was digested with EcoRI and BamHI to yield a fragment approximately 504 base pairs in length corresponding to the feline IFN-γ gene. Fragment 3 is an approximately 3010 base pair BaMHI to PvuII restriction fragment of plasmid pJF751 (Ferrari, et al). Fragment 4 is an approximately 2149 base pair AccI to HindIII sub-fragment of the SPV HindIII fragment M. The AccI sites in fragments 1 and 4 were converted to unique NotI sites using NotI linkers.

HOMOLOGY VECTOR 926-76.D7. The homology vector 926-76.D7 was constructed for the purpose of deleting a portion of the gE coding region from the feline herpesvirus and inserting a foreign DNA. It incorporates a feline CD80 gene flanked by FHV DNA. The feline CD80 gene was under the control of the FHV gE promoter. It was constructed from the indicated DNA sources utilizing standard recombinant DNA techniques (Sambrook, et al.). The plasmid vector is derived from an approximately 2958 base pair Asp718I to Asp718I restriction endonuclease fragment of a pSP18/19. Fragment 1 is an approximately 1415 base pair Asp718I to SmaI subfragment of the FHV SalI B fragment. Fragment 2 is an approximately 879 base pair EcoRI to BamHI fragment of the feline CD80 gene synthesized by CLONING WITH THE POLYMERASE CHAIN REACTION. The template for the PCR reaction was RNA from ConA stimulated feline spleen cells. The upstream primer (5'-TCGAGAATTCGGGTCACGCAGCAAAGTGG-3'; 1/97.43) (SEQ ID NO 52) synthesizes from the 5' end of the feline CD80 gene and introduces an EcoRI site The downstream primer (5'-GCTAGGATCCAATCTATGTAGACAGGTGAGAT-3'; 1/97.6) (SEQ ID NO 53) synthesizes from the 3' end of the feline CD80 gene, introduces an BamHI site at the 3' end of the gene, and was used for reverse transcription and polymerase chain reaction. Fragment 3 is an approximately 2205 base pair SalI to Asp718I subfragment of the FHV EcoRI E fragment.

HOMOLOGY VECTOR 930-23.A1. The plasmid 930-23.A1 was constructed for the purpose of inserting foreign DNA into SPV. It incorporates an *E. coli* β-galactosidase (lacZ) marker gene and the feline CD80 gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase(lacz) marker gene is under the control of a synthetic late pox promoter (LP1), and the feline CD80 gene is under the control of a synthetic late/early pox promoter (LP2EP2). It may be constructed utilizing standard recombinant DNA techniques (Sambrook, et al.), by joining restriction fragments from the following sources. The plasmid vector was derived from an approximately 2972 base pair HindIII to BamHI restriction fragment of pSP64 (Promega). Fragment 1 is an approximately 1484 base pair Bg1II to AccI restriction sub-fragment of the SPV HindIII restriction fragment M. Fragment 2 is an EcoRI to BamHI restriction fragment synthesized by reverse transcription and polymerase chain reaction (PCR) using RNA from ConA stimulated feline spleen cells as a template. To synthesize feline CD80, the primer 5'-TCGAGAATTCGGGTCACGCAGCAAAGTGG-3'; 1/97.43) (SEQ ID NO 52) synthesized from the 5' end of the feline CD80 gene, introduced an EcoRI site at the 5' end of the gene. The primer (5'-GCTAGGATCCAATCTATGTAGACAGGTGAGAT-3'; 1/97.6) (SEQ ID NO 53) was used for reverse transcription and PCR and synthesized from the 3' end of the feline CD80 gene, introduced a BamHI site at the 3' end of the gene. The PCR product was digested with EcoRI and BamHI to yield a fragment approximately 879 base pairs in length corresponding to the feline CD80 gene. Fragment 3 is an approximately 3010 base pair BamHI to PvuII restriction fragment of plasmid pJF751 (Ferrari, et al). Fragment 4 is an approximately 2149 base pair AccI to HindIII sub-fragment of the SPV HindIII fragment M. The AccI sites in fragments 1 and 4 were converted to unique NotI sites using NotI linkers.

HOMOLOGY VECTOR 930-26.A1. The plasmid 930-26.A1 was constructed for the purpose of inserting foreign DNA into SPV. It incorporates an *E. coli* β-galactosidase (lacz) marker gene and the feline CD28 gene flanked by SPV DNA. Upstream of the foreign genes is an approximately 1484 base pair fragment of SPV DNA. Downstream of the foreign genes is an approximately 2149 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the β-galactosidase(lacZ) marker gene is under the control of a synthetic late pox promoter (LP1), and the feline CD28 gene is under the control of a synthetic late/early pox promoter (LP2EP2). It may be constructed utilizing standard recombinant DNA techniques (Sambrook, et al.), by joining restriction fragments from the following sources. The plasmid vector was derived from an approximately 2972 base pair HindIII to BamHI restriction fragment of pSP64 (Promega). Fragment 1 is an approximately 1484 base pair Bg1II to AccI restriction sub-fragment of the SPV HindIII restriction fragment M. Fragment 2 is an EcoRI to BamHI restriction fragment synthesized by reverse transcription and polymerase chain reaction (PCR) using RNA from ConA stimulated feline spleen cells as a template.. To synthesize feline CD28, the primer 5'-GATGAATTCCATGATCCTCAGGCTGGGCTTCT-3'; 7/97.1) (SEQ ID NO 54) synthesized from the 5' end of the feline CD28 gene, introduced an EcoRI site at the 5' end of the gene. The primer (5'-GATCAGATCTCAGGAACGGTATGCCGCAA-3'; 7/97.2) (SEQ ID NO 55) was used for reverse transcription and PCR and synthesized from the 3' end of the feline CD28 gene, introduced a BamHI site at the 3' end of the gene. The PCR product was digested with EcoRI and BamHI to yield a fragment approximately 666 base pairs in length corresponding to the feline CD28 gene. Fragment 3 is an approximately 3010 base pair BamHI to PvuII restriction fragment of plasmid pJF751 (Ferrari, et al). Fragment 4 is an approximately 2149 base pair AccI to HindIII sub-fragment of the SPV HindIII fragment M. The AccI sites in fragments 1 and 4 were converted to unique NotI sites using NotI linkers.

HOMOLOGY VECTOR 931-21.A1: The homology vector 931-21.A1 was used to insert foreign DNA into SPV. It incorporates an *E. coli* β-glucuronidase (uidA) marker gene and the feline CD80 gene flanked by SPV DNA. When this homology vector was used according to the HOMOLOGOUS RECOMBINATION PROCEDURE FOR GENERATING RECOMBINANT SPV, a virus containing DNA coding for the foreign genes results. Note that the β-glucuronidase (uidA) marker gene is under the control of a synthetic early pox promoter (EP2) and the feline CD80 gene is under the control of a separate and unique synthetic late/early pox promoter (LP2EP2). The homology vector was constructed utilizing standard recombinant DNA techniques (Sambrook, et al.), by joining restriction fragments from the following sources with the appropriate synthetic DNA sequences. The plasmid vector was derived from an approximately 2700 base pair DraI restriction fragment of PNEB193 (New England Biolabs). Fragment 1 is an approximately 881 base pair DraI to EcoRI restriction sub-fragment of the SPV HindIII fragment K. Fragment 2 is an approximately 879 base pair EcoRI to BamHI fragment of the feline CD80 gene synthesized by CLONING WITH THE POLYMERASE CHAIN REACTION. The template for the PCR reaction was RNA from ConA stimulated feline spleen cells. The upstream primer (5'-TCGAGAATTCGGGTCACGCAGCAAAGTGG-3'; 1/97.43) (SEQ ID NO 52) synthesizes from the 5' end of the feline CD80 gene and introduces an EcoRI site The downstream primer (5'-GCTAGGATCCAATCTATGTAGACAGGTGAGAT-3'; 1/97.6) (SEQ ID NO 53) synthesizes from the 3' end of the feline CD80 gene, introduces an BamHI site at the 3' end of the gene, and was used for reverse transcription and polymerase chain reaction. Fragment 3 is an approximately 1823 base pair EcoRI to SmaI restriction fragment of plasmid pRAJ260 (Clonetech). Fragment 4 is an approximately 994 base pair EcoRI to DraI restriction sub-fragment of the SPV HindIII restriction fragment K. The EcoRI site in the SPV homology vector was converted to a unique NotI site using synthetic linkers.

HOMOLOGY VECTOR 931-22.A1 The plasmid 931-22.A1 was constructed for the purpose of inserting foreign DNA into RPV. It incorporates a feline CD80 gene flanked by RPV DNA. Upstream of the foreign gene is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the feline CD80 gene is under the control of a late/early promoter (LP2EP2). It was constructed utilizing standard recombinant DNA techniques (Sambrook, et al.), by joining restriction fragments from the following sources with the synthetic DNA sequences. The plasmid vector was derived from an approximately 2999 base pair HindIII restriction fragment of pSP64 (Promega) . Fragment 1 is an approximately 906 base pair HindIII to XbaI restriction sub-fragment of the RPV HindIII restriction fragment U (Knight, et al.). Fragment 2 is an approximately 879 base pair EcoRI to BamHI fragment of the feline CD80 gene synthesized by CLONING WITH THE POLYMERASE CHAIN REACTION. The template for the PCR reaction was RNA from ConA stimulated feline spleen cells. The upstream primer (5'-TCGAGAATTCGGGTCACGCAGCAAAGTGG-3'; 1/97.43) (SEQ ID NO 52) synthesizes from the 5' end of the feline CD80 gene and introduces an EcoRI site The downstream primer (5'-GCTAGGATCCAATCTATGTAGACAGGTGAGAT-3'; 1/97.6) (SEQ ID NO 53) synthesizes from the 3' end of the feline CD80 gene, introduces an BamHI site at the 3' end of the gene, and was used for reverse transcription and polymerase chain reaction. Fragment 3 is an approximately 895 base pair XbaI to HindIII subfragment of the RPV HindIII fragment U. The XbaI sites in-fragments 1 and 3 were converted to unique NotI sites using NotI linkers. Synthetic DNA between fragments 2 and 3 contains the LP2EP2 promoter and an EcoRI site and a BamHI site for insertion of foreign DNA.

HOMOLOGY VECTOR 931-32.A5. The plasmid 931-32.A5 was constructed for the purpose of inserting foreign DNA into RPV. It incorporates a feline CD80 gene and an *E. coli* β-galactosidase(lacZ) marker gene flanked by RPV DNA. Upstream of the foreign genes is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. It was constructed utilizing standard recombinant DNA techniques (Sambrook, et al.), by joining restriction fragments from the following sources with the synthetic DNA sequences. The plasmid vector was derived from an approximately 2999 base pair HindIII restriction fragment of pSP64 (Promega). Fragment 1 is an approximately 906 base pair HindIII to XbaI restriction sub-fragment of the RPV HindIII restriction fragment U (Knight, et al.). Fragment 2 is an approximately 879 base pair EcoRI to BamHI fragment of the feline CD80 gene synthesized by CLONING WITH THE POLYMERASE CHAIN REACTION. The template for the PCR reaction was RNA from ConA stimulated feline spleen cells. The upstream primer (5'-TCGAGAATTCGGGTCACGCAGCAAAGTGG-3'; 1/97.43) (SEQ ID NO 52) synthesizes from the 5' end of the feline CD80 gene and introduces an EcoRI site The downstream primer (5'-GCTAGGATCCAATCTATGTAGACAGGTGAGAT-3'; 1/97.6) (SEQ ID NO 53) synthesizes from the 3' end of the feline CD80 gene, introduces an BamHI site at the 3' end of the gene, and was used for reverse transcription and polymerase chain reaction. Fragment 3 is an approximately 3010 base pair BamHI to PvuII restriction fragment of plasmid pJF751 (Ferrari, et al.). Fragment 4 is an approximately 895 base pair XbaI to HindIII subfragment of the RPV HindIII fragment U. The XbaI sites in fragments 1 and 4 were converted to unique NotI sites using NotI linkers.

HOMOLOGY VECTOR 931-55.B12: The homology vector 931-55.B12 was used to insert foreign DNA into SPV. It incorporates an *E. coli* β-glucuronidase (uidA) marker gene and the feline IFN-γ gene (Onions, et al., (1996); Argyle, et al., (1995)) flanked by SPV DNA. When this homology vector was used according to the HOMOLOGOUS RECOMBINATION PROCEDURE FOR GENERATING RECOMBINANT SPV, a virus containing DNA coding for the foreign genes results. Note that the β-glucuronidase (uidA) marker gene is under the control of a synthetic early pox promoter (EP2) and the feline IFN-γ gene is under the control of a separate and unique synthetic late/early pox promoter (LP2EP2). The homology vector was constructed utilizing standard recombinant DNA techniques (Sambrook, et al.), by joining restriction fragments from the following sources with the appropriate synthetic DNA sequences. The plasmid vector was derived from an approximately 2700 base pair DraI restriction fragment of PNEB193 (New England Biolabs). Fragment 1 is an approximately 881 base pair DraI to EcoRI restriction sub-fragment of the SPV HindIII fragment K. Fragment 2 is an EcoRI to BamHI restriction fragment synthesized by reverse transcription and polymerase chain reaction (PCR) using RNA from ConA stimulated feline spleen cells as a template. To synthesize feline IFN-γ, the primer 5'-TCGAGAATTCGATGAATTACACAAGTTTTATTTTCG-3'; 1/97.4) (SEQ ID NO 81) synthesized from the 5' end of the feline IFN-γ gene, introduced an EcoRI site at the 5' end of the gene. The primer (5'-TCGAGGATCCTTATTTCGATGCTCTACGGCCTC-3'; 1/97.3) (SEQ ID NO 82) was used for reverse transcription and PCR and synthesized from the 3' end of the feline IFN-g gene, introduced a BamHI site at the 3' end of the gene. The PCR product was digested with EcoRI and BamHI to yield a fragment approximately 504 base pairs in length corresponding to the feline IFN-γ gene. Fragment 34 is an approximately 1823 base pair EcoRI to SmaI restriction fragment of plasmid pRAJ260 (Clonetech). Fragment 4 is an approximately 994 base pair EcoRI to DraI restriction sub-fragment of the SPV HindIII restriction fragment K. The EcoRI site in the SPV homology vector was converted to a unique NotI site using synthetic linkers.

HOMOLOGY VECTOR 846-88.B17. The plasmid 846.88.bl7 was constructed for the purpose of deleting the entire gE coding region from the feliie herpesvirus and inserting a foreign DNA. It incorporates an *E. Coli* β-galoctosidase (lacZ) marker gene inserted into the FHV gE deleted site flanked by HV DNA. The plasmid 846-88.B17 contains a 1638 base pair deletion of the gE gene from the SmaI site in the FHV SalI B fragment to the SalI site in the FHV EcoRI E fragment. The SmaI site in the FHV SalI B fragement and the SalI site in the FHV EcoRI E fagment define the endpoints of the deletion of the gE gene. Upstream of the foreign gene is an approximately 1415 base pair Asp718 to SamI subfragment of FHV SalI B containing the entire coding sequence of the gI gene (370 amino acids), Downstream of the foreign gene is an approximately 2205 base pair SalI to Asp 718 subfragment of the FHV EcoRI E fragment which contains unique short and terminal repeat sequence. When the plamid is used according to the HOMOLOGOUS RECOMBINATION PROCEDURE FOR GENERATING RECOMBINANT RPV, SPV OR FHV, a virus containing DNA coding for the foreign ene will result. Note that the *E.coli* lac Z gene is under the control of the constitutive FHV gE promoter. It was constructed utilizing standard recombinant DNA techniques (Sambrook, et al.)

HOMOLOGY VECTOR 921-65.B5. The homology vector 921-656.B5 was constructed to delete the SPV 15L gene (approximately 237bp) and to insert foreign DNA into SPV. It incorporates an *E. Coli* β-galactosidase (LacZ) marker gene and the feline lukimia virus (FeLV) gag/protease and envelope genes flanked by SPV DNA. When this homology vector was sued according to the HOMOLOGOUS RECOMBINATION PROCEDURE FOR GENERATING RECOMBINANT RPV, SPV or FHV a various containing DNA coting for the foreign genes results. It was contructed utilizing standard recombinant DNA techniques (Sambrook, et al.). Note that the β galactosidase (lacZ) marker gene is under the control of the constitutive late pox promoter (I5L) and the FeLV gag/protease and the FeLV envelope genes are under the control of distinct synthetic early pox promoters, EP2 and EP1, respectively. The SPV sequence flanking the foreign gene insertions were derived from a 3.2 kb HingIII N genomic fragment. The upstream sequence of the foreign genes is a 903 bp fragment containing part of the SPV 14L gene and the downstream sequence is a 966 bp fragment containing part of the SPV 16L gene. The e.coli lacZ gene, FeLV envelope and FeLV gag/protease open reading frames all run in the same orientation with respect to the SPV 16L and SPV 14L genes.

HOMOLOGY VECTOR 942-03.C6. The plasmid 942-03.C6 was constructed for the purpose of deleting a portion of the gE coding region from the feline herpesvirus and inserting three foreign genes into the gE deleted site. It incorporates a feline CD80 gene(~879 bp), and FIV gag/protease gene (~1800 bp) and an FIV envelope gene (~2600 bp) flanked by FHV DNA. The feline CD80 gene was under the control of the FHV gE promoter; the FIV gag/protease gene is tunder the control of the pseudorabies gX promoter and the FIVenvelope gene is under the control of the cytomegalovirus immediate early gene. Upstream of the foreign genes is an approximately 1415 base pair Asp718 to SmaI subfragment of the FHV SalI B fragment. Downstream of the foreign genes is approximately 2205 base pair SalI to Asp718 subfragment of the FHV EcoRI E fragment which contains unique short and terminal repeat sequence. When the plasmid is used according to the HOMOLOGOUS RECOMBINATION PRECEDURE FOR GENERATING RECOMBINANT RPV, SPV or FHV, a virus containing DNA coding for the foreign gene will result. The homology plasmid, 942-03.C6 was constructed utilizing standard recombinant DNA techniques (Sambrook, et al.).

EXAMPLES

Examples 1A

Cloning of th efeline CD80 (B7-1)-TAMU, CD80 (B7-1)-SPAH, C86 (B7-2), CD28, and CTLA-4 cDNA:

The feline CD80 (B7-1), CD86 (B7-2), CD28, and CTLA-4 cDNA were cloned by first RT-PCR (Reverse transcriptase/Polymerase chain reaction) amplifying a region between two sequences that were conserved enough to make degenerate primers that interacted with the feline mRNA. The source of the mRNA was peripheral blood mononuclear cells (PBMC) or splenocytes stimulated for at least 16 hours with Con A. This PCR product was sequenced. The sequence was used to make primers for RACE (rapid amplification of cDNA ends) PCR. The 5' end was amplified by first making cDNA with a downstream primer complimentary to the newly sequenced conserved region. An oligonucleotide was ligated to the 3' end of the cDNA (compliment with the 5' end of mRNA). This sequence served as the binding site for the upstream primer which was PCR compatible with the downstream PCR primer that corresponded with another region in the newly sequenced region. Degenerate primers were employed in multiple rounds of nested reactions to obtain the 3' end. This upstream primer for PCR was designed to react with a sequence in the newly sequenced region. Products were either sequenced directly or cloned into a TA cloning vector and sequenced from the plasmid. The whole open reading frame was cloned by amplifying in its entirety by PCR with primers constructed from the known sequences. The ORFs were cloned and sequenced three times. The B7-1 ORF was subcloned into a pSI plasmid with an SV40 promoter, and the SFV plasmid. The pSI was used to establish the functional interaction of B7-1 with the feline CD28.

DNA primers used for RT/PCR of the feline CD80 (B7-1) cDNA were:

```
5' Primer: 5'-CGCGGATCCGCACCATGGGTCACGCAGCAAAGTGGAAAAC-3';  (SEQ ID NO. 11)

3' Primer: 5'-CCTAGTAGAGAAGAGCTAAAGAGGC-3'                  (SEQ ID NO. 12)
```

(See above for complete list of primers for feline CD80 cDNA).

DNA primers used for RT/PCR of the feline CD28 cDNA were:

```
5' Primer: 5'-CGCGGATCCACCGGTAGCACAATGATCCTCAGG-3';  (SEQ ID NO. 13)

3' Primer: 5'-CGCGGATCCTCTGGATAGGGGCCATGTCAG-3'      (SEQ ID NO. 14)
```

(See above for complete list of primers for feline CD28 cDNA).

DNA primers used for RT/PCR of the feline CTLA-4 cDNA were:

1. Degenerate primers for the first PCR product (672 bp):

```
                                                  (SEQ ID NO. 15)
Deg 5' P: 5'-ATGGCTT(C)GCCTTGGATTT(C)CAGC(A)GG-3';

                                                  (SEQ ID NO. 16)
Deg 3' P: 5'-TCAATTG(A)ATG(A)GGAATAAAATAAGGCTG-3';
```

2. 5' end of CTLA-4 (455 bp): Degenerate, gene-specific (GSP) and nested gene-specific (NGSP) primers:

```
First Round PCR:
Deg 5' P: 5'-TGTTGGGTTTC(T)G(A)CTCTG(A)CTCTG(A)CTT(C)CCTG-3';  (SEQ ID NO. 17)

3' GSP:   5'-GCATAGTAGGGTGGTGGGTACATG-3';                     (SEQ ID NO. 18)

Nested PCR with the PCR product of the first round:
Deg 5' P: 5'-TGTTGGGTTTC(T)G(A)CTCTG(A)CTT(C)CCTG-3';          (SEQ ID NO. 19)

3' NGSP:  5'-ACATGAGCTCCACCTTGCAG-3';                         (SEQ ID NO. 20)
```

3. 3' end of CTLA-4: Adaptor primer 1 (AP1, Clonetech Lab, Inc., Palo Alto, Calif.); Nested adaptor primer (AP2, Clonetech Lab), gene-specific primer (GSP), and nested gene-specific primer (NGSP):

```
3' RACE PCR:
AP1:      5'-CCATCCTAATACGACTCACTATAGGGC-3';    (SEQ ID NO. 21)

5' GSP:   5'-GTGAATATGGGTCTTCAGGCAATG-3';       (SEQ ID NO. 22)

3' Nested RACE PCR with the product of 3' RACE PCR:
AP2:      5'-ACTCACTATAGGGCTCGAGCGGC-3';        (SEQ ID NO. 23)

5' NGSP: 5'-GAAATCCGAGTGACTGTGCTGAG-3';         (SEQ ID NO. 24)
```

4. Primers for whole CTLA-4 gene

```
Fel CTLA-4 5' Primer: 5'-AACCTGAACACTGCTCCCATAAAG-3';  (SEQ ID NO. 25)

Fel CTLA-4 3' Primer: 5'-GCCTCAGCTCTTAGAAATTGGACAG-3'; (SEQ ID NO. 26)
```

DNA primers used for RT/PCR of the feline CD86 (B7-2) CDNA were:

1. Degenerate primers for the first PCR product (423 bp):

```
                                                  (SEQ ID NO: 27)
Deg 5' P: 5'-TAGTATTTTGGCAGGACCAGG-3';

                                                  (SEQ ID NO. 28)
Deg 3' P: 5'-CTGTGACATTATCTTGAGATTTC-3';
```

2. Degenerate primers for the second PCR product (574 bp):

```
                                                  (SEQ ID NO: 29)
Deg 5' P: 5'-GA(A)CA(T)GCACT(A)ATGGGACTGAG-3';

                                                  (SEQ ID NO. 30)
Deg 3' P: 5'-CTGTGACATTATCTTGAGATTTC-3';
```

3. 5' end of CD86: AP1, AP2 (Clontech Lab), Degenerate, 3'-gene-specific (GSP) and 3'-nested gene-specific (NGSP) primers:

```
5' RACE PCR:
AP1:     5'-CCATCCTAATACGACTCACTATAGGGC-3';   (SEQ ID NO. 31)

3' GSP:  5'-TGGGTAACCTTGTATAGATGAGCAGGTC-3';  (SEQ ID NO. 32)

Nested 5' RACE PCR with the PCR product of 5'RACE:
AP2:     5'-ACTCACTATAGGGCTCGAGCGGC-3';       (SEQ ID NO. 33)

3' NGSP: 5'-CAGGTTGACTGAAGTTAGCAAGCAC-3';
```

4. 3' end of B7-2: AP1, AP2, 5' GSP, and 5' NGSP:

```
3' RACE PCR:
AP1:                       5'-CCATCCTAATACGACTCACTATAGGGC-3';  (SEQ ID NO. 35)

5' GSP:                    5'-GGACAAGGGCACATATCACTGTTTC-3';    (SEQ ID NO. 36)

Nested 5' RACE PCR with the PCR product of 5'RACE:
AP2:                       5'-ACTCACTATAGGGCTCGAGCGGC-3';      (SEQ ID NO. 37)

5' NGSP:                   5'-CAGTGCTTGCTAACTTCAGTCAACC-3';    (SEQ ID NO. 38)

Whole CD86 gene:
Fel B72 (1) 5' Primer:     5'-CGGGAATGTCACTGAGCTTATAG-3';      (SEQ ID NO. 39)

Fel B72 (1176) 3' Primer: 5'-GATCTTTTTCAGGTTAGCAGGG-3'        (SEQ ID NO. 40)
```

Example 1B

Cloning of CD80 (B7-1)-Syntro/SPAH; Plasmid 917-19-8/16

Feline spleen cells were extracted from cats and cultured with Concanavalin A for 5 hours, Cells were pelleted, washed with PBS and used to isolate total RNA(Qiagen RNeasy Total RNA System). Total RNA was treated with DNAse I (Boehringer Mannheim) to remove DNA contamination from the RNA preparations. Messenger RNA was then extracted from these preparations, using Qiagen's Oligotex beads (Santa Clara, Calif.) and (quick columns. Copy DNA was generated from MRNA, in the presence of random hexamers, dNTPs, RNAsin, reverse transcriptase (Promega) and reverse transcriptase buffer (Promega) and incubated at 42° C. for 30 minutes. PCR was then used to generate a double stranded, full-length cDNA clone of the feline B7-1 open reading frame (ORF) using the sense primer 5/97.50 (5'-ATGGGTC-ACGCAGCAAAGTG-3') ; (SEQ ID NO. 41) and antisense primer 5/97.51 (5'-CTATGTAGACAGGTGAGATC-3') ; (SEQ ID NO. 42), dNTPs, B7-1 CDNA (lst strand), $MgSO_4$, Vent polymerase (BRL) and Vent polymerase buffer (BRL). PCR conditions were as follows: 1 cycle of 94°, 15 seconds; 35 cycles of ° 94 for 30 seconds 48° for 2 minutes, 72° for 2 minutes; 1 cycle of 72° for 10 minutes. PCR reactions were run on a 1% low melt agarose gel and DNA fragments corresponding to the expected size of the B7-1 ORF were isolated, gel purified (Qiagen's Gel Purification Kit, Santa Clara, Calif.) and cloned into pCR-BLUNT plasmid vector using kit reagents from Invitrogen's Zero Blunt PCR Cloning Kit (San Diego, Calif.). DNA extracted from kanamycin resistant bacterial colonies were pre-screened for the presence of a unique NheI site (contained in feline CD80 (B7-1)-TAMU). Inserts that were in the range of 800–900 bp size and contained a NheI site were sequenced using ABI's fluorescenated automated sequencing protocols and equipment (Perkin-Elmer-Cetus; Applied Biosystems, Inc.). Plasmid vector and B7-1, gene specific primers derived from the previously cloned B7-1 gene were used to generate DNA sequence pCR-Blunt primers are 1/97.36 (5'-CAGGAAACAGCTATGAC-3'); (SEQ ID NO. 43) and 1/97.37 (5'-AATACGACTCACTATAGG-3'); (SEQ ID NO. 44). B7-1 gene specific primers are : 12/96.22 (5'-AACACCATTTCATCATCCTTT-3') ; (SEQ ID NO. 45), 1/97.33 (5'-ATACAAGTGTATTTGCCATTGTC-3') ; (SEQ ID NO. 46), 12/96.20 (5'-AGCTCTGACCAATAACATCA-3') ; (SEQ ID NO. 47) 12/96.21 (5'-ATTAGAAATCCAGTTCACTGCT-3') ; (SEQ ID NO. 48), 1/97.32 (5'-TCATGTCTGGCAAAGTACAAG-3) ; (SEQ ID NO. 49), 11/96.32 (5'ATTCACTGACGTCACCGA-3') ; (SEQ ID NO. 50), 11/96.31 (5'-AAGGCTGTGGCTCTGA-3') ; (SEQ ID NO. 51). Two clones were determined to contain full-length CD80 sequence corresponding to the original CD80 sequence with the exception of 2 DNA point mutations. One such point mutation did not effect the amino acid sequence. The second mutation resulted in an amino acid change from a Leucine to an Isoleucine. The resultant feline CD80 clone was designated 917-19.8/16. (CD80-Syntro/SPAH).

Example 2

S-SPV-229

S-SPV-229 is a swinepox virus that expresses at least two foreign genes. The gene for *E. coli* β-galactosidase(lacZ) and the gene for feline CD80 were inserted into the SPV AccI site within the larger BglII to HindIII subfragment of SPV genomic fragment HindIII M (a unique NotI restriction site has replaced a unique AccI restriction site). The lacZ gene is under the control of the synthetic late promoter (LP1), and the feline CD80 gene is under the control of the synthetic late/early promoter (LP2EP2).

S-SPV-229 was derived from S-SPV-001 (Kasza Strain) This was accomplished utilizing the homology vector 930-23.A1 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase(BLUOGAL AND CPRG ASSAYS). The final result of red plaque purification was the recombinant virus designated S-SPV-229. This virus was assayed for β-galactosidaseexpression, purity, and insert stability by multiple passages monitored by the blue plaque assay and black plaque assay as described in Materials and Methods. After the initial three rounds of purification, all plaques observed were blue indicating that the virus was pure, stable, and expressing β-galactosidase. (U.S. Pat. No. 5,382,425 is incorporated herein by reference.)

S-SPV-229 was assayed for expression of β-galactosidase-specific antigens using the BLACK PLAQUE SCREEN FOR FOREIGN GENE EXPRESSION IN RECOMBINANT SPV. A monoclonal antibody to β-galactodsidase was shown to react specifically with S-SPV-229 plaques and not with S-SPV-001 negative control plaques. All S-SPV-229 observed plaques reacted with the monoclonal antibody. to β-glactosidase indicating that the virus was stably expressing the β-galactosidase foreign gene. The assays described here were carried out in ESK-4 cells, indicating that ESK-4 cells would be a suitable substrate for the production of SPV recombinant vaccines.

S-SPV-229 is assayed for expression of feline CD80-specific antigens using the SCREEN FOR FELINE CD80 (B7-1) and CD86 (B7-2) EXPRESSION IN RECOMBINANT SPV, RPV or FHV USING BLACK PLAQUE ASSAYS. A human CTLA-4/Fc chimeric antibody is shown to react specifically with S-SPV-229 plaques (expressing feline CD80) and not with S-SPV-001 negative control plaques. All S-SPV-229 observed plaques are shown to react with the human CTLA-4/Fc chimeric antibody indicating that the virus is stably expressing the feline CD80 foreign gene.

To confirm the expression of the feline CD80 gene product, cells are infected with S-SPV-229 and samples of infected cell lysates were subjected to SDS-polyacrylamide gel electrophoresis. The gel are blotted and analyzed using the WESTERN BLOTTING PROCEDURE.

S-SPV-229 is useful as vaccines against disease in felids.

S-SPV-229 improves the efficacy of vaccines against FIV, FeLV, FIP, or other feline diseases when used alone or in combination with FIV, FeLV, FIP, or other feline vaccines. S-SPV-229 is also useful for expression of feline CD80 polypeptide. Cell lysate of S-SPV-229 infected cells is injected into mice or rabbits to raise polyclonal, monospecific antibodies to feline CD80.

Example 3

S-SPV-230

S-SPV-230 is a swinepox virus that expresses at least two foreign genes. The gene for *E. coli* β-galactosidase(lacZ) and the gene for feline CD28 were inserted into the SPV AccI site within the larger BglII to HindIII subfragment of SPV genomic fragment HindIII M (a unique NotI restriction site has replaced a unique AccI restriction site). The lacZ gene is under the control of the synthetic late promoter (LP1), and the feline CD28 gene is under the control of the synthetic late/early promoter (LP2EP2).

S-SPV-230 was derived from S-SPV-001 (Kasza Strain) This was accomplished utilizing the homology vector 930-26.A1 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase(BLUOGAL AND CPRG ASSAYS). The final result of red plaque purification was the recombinant virus designated S-SPV-230. This virus was assayed for β-galactosidaseexpression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-230 is assayed for expression of feline CD28-specific antigens using the BLACK PLAQUE SCREEN FOR FOREIGN GENE EXPRESSION IN RECOMBINANT SPV. The assays described here were carried out in ESK-4 cells, indicating that ESK-4 cells would be a suitable substrate for the production of SPV recombinant vaccines.

To confirm the expression of the feline CD28 gene product, cells are infected with S-SPV-230 and samples of infected cell lysates were subjected to SDS-polyacrylamide gel electrophoresis. The gel are blotted and analyzed using the WESTERN BLOTTING PROCEDURE.

S-SPV-230 is useful as a vaccine against disease in felids. S-SPV-230 improves the efficacy of vaccines against FIV, FeLV, FIP, or other feline when used alone or in combination with FIV, FeLV, FIP, or other feline vaccines. S-SPV-230 is also useful for expression of feline CD28 polypeptide. Cell lysate of S-SPV-230 infected cells is injected into mice or rabbits to raise polyclonal, monospecific antibodies to feline CD28.

Example 4

S-SPV-225

S-SPV-225 is a swinepox virus that expresses at least two foreign genes. The gene for *E. coli* β-galactosidase(lacZ) and the gene for feline interferon-γ (feline IFN-γ) were inserted into the SPV AccI site within the larger BglII to HindIII subfragment of SPV genomic fragment HindIII M (a unique NotI restriction site has replaced a unique AccI restriction site). The lacZ gene is under the control of the swinepox O1L promoter and the feline IFN-γ gene is under the control of the synthetic late/early promoter (LP2EP2).

S-SPV-225 was derived from S-SPV-001 (Kasza Strain). This was accomplished utilizing the homology vector 917-60.B9 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase (BLUOGAL AND CPRG ASSAYS). The final result of red plaque purification was the recombinant virus designated S-SPV-225. This virus was assayed for β-galactosidaseexpression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-225 is assayed for expression of feline IFN-γ-specific antigens using the BLACK PLAQUE SCREEN FOR FOREIGN GENE EXPRESSION IN RECOMBINANT SPV. The assays described here were carried out in ESK-4 cells, indicating that ESK-4 cells would be a suitable substrate for the production of SPV recombinant vaccines.

To confirm the expression of the feline IFN-γ gene product, cells are infected with S-SPV-225 and samples of infected cell lysates were subjected to SDS-polyacrylamide gel electrophoresis. The gel are blotted and analyzed using the WESTERN BLOTTING PROCEDURE.

S-SPV-225 is assayed for expression of bioactive feline IFN-γ using the SCREEN FOR FELINE INTERFERON GAMMA BIOACTIVITY EXPRESSED FROM RECOMBINANT SPV, RPV or FHV USING VSV PLAQUE REDUCTION.

S-SPV-225 is useful as a vaccine against disease in felids. S-SPV-225 improves the efficacy of vaccines against FIV, FeLV, FIP, or other feline when used alone or in combination with FIV, FeLV, FIP, or other feline vaccines.

Example 5

S-SPV-200:

S-SPV-200 is a swinepox virus that expresses three foreign genes. The genes for feline immunodeficiency virus (FIV) gag/protease, and FIV envelope (full length) and the gene for *E. coli* β-galactosidase(lacZ) were inserted into a unique Not I restriction site (Not I linkers inserted into a unique AccI restriction site in the O1L ORF of the SPV HindIII M fragment). The FIVgag/protease and envelope genes are under the control of separate, but identical synthetic late/early promoter (LP2EP2). The lacZ gene is under the control of the synthetic late promoter (LP1).

S-SPV-200 was derived from S-SPV-001 (Kasza Strain). This was accomplished utilizing the homology vector 904-63.B7 and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-galactosidase(BLUOGAL AND CPRG ASSAYS and SCREEN FOR RECOMBINANT HERPESVIRUS EXPRESSING ENZYMATIC MARKER GENES). The final result of red plaque purification was the recombinant virus designated S-SPV-157. This virus was assayed for β-galactosidase expression by the blue plaque assay as described in Materials and Methods. Analysis of purity, and insert stability after 5 passages was performed via detection of FIVgag and β-galactosidase in black plaque assay and the detection of FIVgag and envelope in western blot assay.

S-SPV-200 is a recombinant swinepox virus expressing the FIVgag/protease and FIV envelope proteins and is useful as a vaccine in felids against FIV infection. S-SPV-200 is also useful for expression of the FIV gag/protease and envelope proteins.

Example 6

S-SPV-233

S-SPV-233 is a swinepox virus that expresses five foreign genes: FIVgag, FIVenv, Feline CD80, *E. coli* lacZ and *E. coli* uidA. The full-length feline CD80 gene and the gene for *E. coli* β-glucuronidase (uidA) were inserted into a unique Not I restriction site (Not I linkers inserted into a unique EcoRI restriction site within an approximately 3.2 kb region (SEQ ID NO ) of the 6.7 kb SPV HindIII K fragment). The genes for feline immunodeficiency virus (FIV) gag/protease, and FIV envelope (full length) and the gene for *E. coli* β-galactosidase(lacz) were inserted into a unique Not I restriction site (Not I linkers inserted into a unique AccI restriction site in the O1L ORF of the SPV HindIII M fragment). The CD80 gene is under the control of the synthetic late/early promoter (LP2EP2) and the uidA gene is under the control of a separate and unique synthetic early promoter (EP2). The FIVgag/protease and envelope genes are under the control of separate, but identical synthetic late/early promoter (LP2EP2). The lacZ gene is under the control of the synthetic late promoter (LP1). (PCT International Application WO 96/22363 is incorporated herein by reference.)

S-SPV-233 was derived from S-SPV-200 (contains FIVgag, FIVenvelope and *E. coli* lacZ genes). This was accomplished utilizing the homology vector 931-21.A1 and virus S-SPV-200 in the HOMOLOGOUS RECOMBINATION PROCEDURE FOR GENERATING RECOMBINANT SPV. The transfection stock was screened by the SCREEN FOR RECOMBINANT SPV EXPRESSING β-glucoronidase (X-gLUC and SCREEN FOR RECOMBINANT HERPESVIRUS EXPRESSING ENZYMATIC MARKER GENES). The final result of blue/green purification will be the recombinant virus designated S-SPV-233.

S-SPV-233 is assayed for expression of FIV gag, FIV env, and feline CD80-specific antigens using the BLACK PLAQUE SCREEN FOR FOREIGN GENE EXPRESSION IN RECOMBINANT SPV. The assays described here were carried out in ESK-4 cells, indicating that ESK-4 cells would be a suitable substrate for the production of SPV recombinant vaccines.

S-SPV-233 is assayed for expression of feline CD80-specific antigens using the SCREEN FOR FELINE CD80 (B7-1) and CD86 (B7-2) EXPRESSION IN RECOMBINANT SPV, RPV or FHV USING BLACK PLAQUE ASSAYS. A human CTLA-4/Fc chimeric antibody is shown to react specifically with S-SPV-233 plaques (expressing feline CD80) and not with S-SPV-001 negative control plaques. All S-SPV-233 observed plaques are shown to react with the human CTLA-4/Fc chimeric antibody indicating that the virus is stably expressing the feline CD80 foreign gene.

To confirm the expression of FIV gag, FIV env, and feline CD80 gene product, cells are infected with S-SPV-233 and samples of infected cell lysates were subjected to SDS-polyacrylamide gel electrophoresis. The gel are blotted and analyzed using the WESTERN BLOTTING PROCEDURE.

S-SPV-233 is a recombinant swinepox virus expressing the FIVgag/protease and FIV envelope proteins and is useful as a vaccine in felids against FIV infection. S-SPV-233 is also useful for expression of the FIV gag/protease and envelope proteins.

Example 7

S-SPV-235

S-SPV-235 is a swinepox virus that expresses five foreign genes: FIVgag, FIVenv, Feline IFN-γ, *E. coli* lacZ and *E. coli* uidA. The full-length feline IFN-__γ gene and the gene for *E. coli* β-glucuronidase (uidA) were inserted into a unique Not I restriction site (Not I linkers inserted into a unique EcoRI restriction site within an approximately 3.2 kb region (SEQ ID NO ) of the 6.7 kb SPV HindIII K fragment). The genes for feline immunodeficiency virus (FIV) gag/protease, and FIV envelope (full length) and the gene for *E. coli* β-galactosidase (lacZ) were inserted into a unique Not I restriction site (Not I linkers inserted into a unique AccI restriction site in the O1L ORF of the SPV HindIII M fragment). The IFN-γ gene is under the control of the synthetic late/early promoter (LP2EP2) and the uidA gene is under the control of a separate and unique synthetic early promoter (EP2). The FIVgag/protease and envelope genes are under the control of separate, but identical synthetic late/early promoter (LP2EP2). The lacZ gene is under the control of the synthetic late promoter (LP1).

S-SPV-235 was derived from S-SPV-200 (contains FIVgag, FIVenvelope and *E. coli* acZ genes). This was accomplished utilizing the homology vector 931-55.B12 and virus S-SPV-200 in the HOMOLOGOUS RECOMBINATION PROCEDURE FOR GENERATING RECOMBINANT SPV. The transfection stock was screened by the SCREEN FOR RECOMBINANT SPV EXPRESSING β-glucoronidase (X-GLUC and SCREEN FOR RECOMBINANT HERPESVIRUS EXPRESSING ENZYMATIC MARKER GENES). The final result of blue/green purification is the recombinant virus designated S-SPV-235.

S-SPV-235 is assayed for expression of FIV gag, FIV env, and feline IFN-γ-specific antigens using the BLACK PLAQUE SCREEN FOR FOREIGN GENE EXPRESSION IN RECOMBINANT SPV. The assays described here were carried out in ESK-4 cells, indicating that ESK-4 cells would be a suitable substrate for the production of SPV recombinant vaccines.

S-SPV-225 is assayed for expression of bioactive feline IFN-γ using the SCREEN FOR FELINE INTERFERON GAMMA BIOACTIVITY EXPRESSED FROM RECOMBINANT SPV, RPV or FHV USING VSV PLAQUE REDUCTION.

To confirm the expression of FIV gag, FIV env, and feline IFN-γ gene product, cells are infected with S-SPV-235 and samples of infected cell lysates were subjected to SDS-polyacrylamide gel electrophoresis. The gel are blotted and analyzed using the WESTERN BLOTTING PROCEDURE.

S-SPV-235 is a recombinant swinepox virus expressing the FIVgag/protease and FIV envelope proteins and is useful as a vaccine in felids against FIV infection. S-SPV-235 is also useful for expression of the FIV gag/protease and envelope proteins.

Example 8

S-SPV-224

S-SPV-224 is a swinepox virus that expresses three foreign genes. The genes for feline leukemia virus (FeLV) gag/protease, and FeLV envelope (full lenght) and the gene for *E. coli* (lacZ) were inserted into a deleted SPV I5L site derived form a SPV 1869 bp partial HindIII N genomic fragment. The FeLV gag/protease gene is under the control of the synthetic early pox promoter (EP2). The FeLV envelope gene is under the control of the synthehetic early pox promoter (EP1). The lacz gene is under the control of the constitutive late SPV I5L promoter.

S-SPV-224 was derived from S-SPV-001 (Kasza Strain). This was accomplished utilizing the homology vector 921-65.B5 and virus S-SPV-001 in HOMOLOGOUS RECOMBINATION PROCEDURE FOR GENERATING RECOMBINANT RPV, SPV, OF FHV. The transfection stock was scrend by the SCREEN FOR RECOMBINANT RPV OR SPV FHV expressing β-galactosidase (BLUOGAL AND CPRG ASSAYS) or β-galactosidase (X-GLUCASSAYS). The final results of red plaque purification was the recombinant virus designated S-SPV-224. This virus was acids for β-galactosidase expression by the blue plaque acids a described in Materials and Methods.

S-SPV-224 is assayed for expression of FeLV gag/protease, FeLV env, And β-galactosidase proteins using proteins using the SCREEN FOR FOREIGN GENE EXPRESSION IN RECOMBINANT RPV, SPV, OR FHV USING BLACK PLAQUE ASSAYS. The assays described here were carried out in ESK-4 cells would be a suitable substrate for the production of SPV recombinant vaccines. Aug. 14, 1998

To confirm the expression of FeLV gag/protease and FeLV env gene products, cells are infected with S-SPV-224 and samples of infected cells lysates were subjected to SDS-polyacrylamide gel electrophoresis. The gel are blotted and analyzed using the WESTERN BLOTTING PROCEDURE.

S-SPV-224 is a recombinant swinepox virus expressing the FeLVgag/protease, and FeLV envelope proteins and is useful as a vaccine in fields against FeLV infectious. S-SPV-224 is also useful for expression of the FeLV gag/protease and envelope proteins.

Example 9

S-SPV-246

S-SPV-246 is a swinepox virus that expresses five foreign genes: FeLV gag/protease, FeLVenv, Feline CD80, *E. coli* lacZ and *E. coli* uidA. the full-length feline CD80 gene and the gene for *E. coli* β-galactosidase (uidA) were inserted into a unique Not I restriction site (Not I linker inserted into a unique EcoRI restriction site within an approximately 3.2 kb region of the 6.7 kb SPV HindIII k fragment). The CD80 gene is under the control of the synthetic late/early promoter (LP2EP2) and the uidA gene is under control of the synthetic early pox promoter, EP2. The FeLVgag/protease, FeLV envelope (full length) and the *E. coli* β-galactosidase (lacZ) genes were inserted into a deleted I5L site derived from a 1869 partial HindIII N genomic fragment. The FeLVgag/protease gene is under the control of the synthetic early pox promoter, EP2. The FeLV envelope gene is under the control of the synthetic early pox promoter, EP1. The lacZ gene is under the control of the constitutive late pox promoter, I5L. (PCT International Application WO 96/22263 is incorporated herein by reference.)

S-SPV was derived from S-SPV-224 (contains FeL Vgag/protease, FeLVenvelope and *E. coli* lacZ gene in the I5L deleted 1869 kb partial HindIII N fragment). This was accomplished utilizing the homology vector 931-21.A1 and virus S-SPV-224 in the HOMOLOGOUS RECOMBINATION PROCEDURE FOR GENERATING RECOMBINANT RPV, SPV, OR FHV. The transfection stock was screened by the SCREEN FOR RECOMBINANT RPV OR SPV OR FHV EXPRESSING β-galactosidase (BLUOGAL AND CPRG ASSAYS) OR β-galactosidase (X-GLUC ASSAY). The final result of blu/green plaque purification will be the recombinant virus designated S-SPV-246.

S-SPV-246 is assayed for expression of FeLV gag/protease, and FeLV envelope proteins using the SCREEN FOR FOREIGN GENE EXPRESSION IN RECOMBINANT RPV, SPV, OR FHV USING BLACK PLAQUE ASSAYS. The assays described here were carried out in ESK-4 cells, indicating that ESK-4 cells would be a suitable substrate for the production of SPV recombinant vaccines.

S-SPV-246 is assayed for expression of feline CD80-specific antigen using the SCREEN FOR FELINE CD80 (B7-1) AND CD86 (B7-2) EXPRESSION IN RECOMBINANT SPV, RPV OR FHV USING BLACK PLAQUE ASSAYS A human CTLA-4/Fc chimeric antibody is shown to react specifically with S-SPV-246 plaques (expressing feline CD80) and not with S-SPV-001 negative control plaques. All S-SPV-246 observed plaques are shown to react with the human CTLA-4/Fc chimeric antibody indicating that the virus is stably expressing the feline CD80 foreign gene.

To confirm the expression of FeL V gag/protease, FeLV envelope, and feline CD80 gene product, cells are infected with S-SPV-246 and samples of infected cell lysates are subjected to SDS-polyacrylamide gell electrophoresis. the gell are bottled and analyzed using the WESTERN BLOTTING PROCEDURE.

S-SPV-246 is a recombinant swinepox virus expressing the FeL V gag/protease and FeLV envelope proteins and is useful as a vaccine in fields against FeLV infections.

S-SPV-246 is also useful for expression of the FeLV gag/protease and envelope proteins.

Example 10

Additional examples of recombinant swinepox virus useful as a vaccine against feline immunodeficiency virus (FIV), feline leukemia virus (FeLV) or feline infectious peritonitis (FIP) are:

A recombinant swinepox virus expresses five foreign genes. The FIV env gene is under the control of the synthetic early pox promoter EPI; the FIV gag/protease gene is under the control of the synthetic early pox promoter EP2; the *E. coli* lacZ gene is under the control of the swinepox promoter I5L; the feline CD80 gene is under the control of the synthetic late/early pox promoter LP2EP2; the *E. coli* idA gene is under the control of the synthetic early pox promoter EP2. The FIV envelope gene, FIV gag/protease and *E. coli* lacZ genes are located in a different and distinct non-essential SPV insertion site from the feline CD80 and the *E. coli* uidA gene insertions.

A recombinant swinepox virus expresses five foreign genes. The FIV env gene is under the control of the synthetic early pox promoter EP1; the FIV gag/protease gene is under the control of the synthetic early pox promoter EP2; the *E. coli* lacZ gene is under the control of the swinepox promoter I5L; the feline CD86 gene is under the control of the synthetic late/early pox promoter LP2EP2; the *E. coli* uidA gene is under the control of the synthetic early pox promoter EP2. The FIV envelope gene, FIV gag/protease and *E. coli* lacZ genes are located in a different and distinct non-essential SPV insertion site from the feline CD86 and *E. coli* uidA insertion.

A recombinant swinepox virus expresses two foreign genes. The feline CD86 gene is under the control of the synthetic late/early pox promoter LP2EP2; the *E. coli* uidA gene is under the control of the synthetic early pox promoter EP2. This virus has use alone or in combination with other recombinant proteins or vaccine.

Additional examples of recombinant swinepox viruses useful for production of vaccines against FeLV disease would be the same as described above, with the exception of replacing the FIV gene with the comparable FeLV specific genes.

Additional examples of recombinant swinepox viruses useful for production of proteins for use as a vaccine for polyclonal antibody production and purification are:

A recombinant swinepox virus expresses one foreign gene. The feline CD80 gene lacking the transmembrane domain is under the control of the synthetic late/early pox promoter LP2EP2. Alternatively, the feline CD80 gene lacking the transmembrane domain has a histidine tag fusion at the carboxyl terminus to allow purification on a nickel affinity column.

A recombinant swinepox virus expresses on foreign gene. The feline CD28 gene lacking the transmembrane domain is under the control of the synthetic late/early pox promoter LP2EP2. Alternatively, the feline CD28 gene lacking the transmembrane domain has a histidine tag fusion at the carboxyl terminus to allow purification on a nickel affinity column.

A recombinant swinepox virus expresses on e foreign gene. The feline CD86 gene lacking the transmembrane domain is under the control of the synthetic late/early pox promoter LP2EP2. Alternatively, the feline CD86 gene lacking the transmembrane domain has a histidine tag fusion at the carboxyl terminus to allow purification on a nickel affinity column.

Additional examples of recombinant swinepox viruses utilizing both CD80 and CD86 and useful for vaccine development for FIV and FeLV disease in fields are:

A recombinant swinepox virus expresses five foreign genes. The feline Cd86- gene and the Cd-80 genes are expressed in a bicistronic cassette under the control of the synthetic late/early pox promoter LP1, driving the transcription of CD80 and CD86 and including an EMCV IRES element between the two open reading frames; the *E. coli* uidA gene is under the control of the synthetic early promoter, EP2. The FIV gag/protease gene is under the control of the swinepox promoter, OIL; the *E. coli* LacZ gene is under the control of the synthetic late pox promoter, LP1. The CD80/CD86 and the *E. coli* uidA genes are contained in a different and distinct non-essential SPV insertion site from the FIVgag/protease and *E. coli* lacZ gene insertions.

A recombinant swinepox virus expresses five foreign genes. The feline CD86- gene and the CD-80 genes are expressed in bicistronic cassette under the control of the synthetic late/early pox promoter LP1, driving the transcription of CD80 and CD86 and including an EMCV IRES element between the two open reading frames; the *E. coli* lacZ gene is under the control of the synthetic late promoter, LP1. The FIV envelope gene is under the control of the synthetic early pox under promoter, EP1.

The *E. coli* uidA gene is under the control of the synthetic late pox promoter, LP1. The CD80/CD86 and the *E. coli* uidA gene are contained in a different and distinct non-essential SPV insertion site from the FIVgag/protease and *E. coli* lacZ gene insertions.

A recombinant swinepox virus expresses six foreign genes. The feline Cd86- gene and the CD80 gene expressed in a bicistrnic under the control of the synthetic late pox promoter LP1, driving the transcription of CD80 and CD86 and including an EMCV IRES element between the two open reading frames; the *E. coli* uidA gene is under the control of the synthetic early promoter, EP2. The FIV gag/protease gene is under the control of the early pox promoter , EP2; the FIV envelope gene is under the control of the synthetic early pox promoter, EP1; the *E. coli* LacZ gene is under the control of the constitutive 15L pox promoter. The CD80/CD86, and *E. coli* uidA genes are inserted into a distinct site from the insertion of the FIV envelope, FIV gag/protease and *E. coli* LacZ gene insertions.

Additional swinepox viruses for use a FeLV vaccines for fields would be constructed as described above, replacing the FIV genes for the comparable FeLV gene constructs.

Example 11

Additional examples of recombinant raccoonpox virus useful as a vaccine against feline diseases such as feline immunodeficiency virus (FIV), feline leukemia virus (FeLV), or feline infectious peritonitis (FIP) are:

A recombinant raccoonpox virus expresses two foreign genes. The feline CD86 is under the control of the synthetic late/early pox promoter LP2EP2; the *E. coli* lacZ gene is under the control of the synthetic late pox promoter L1.

Additional examples of recombinant raccoonpox virus useful for production of proteins for use as a vaccine or for polyclonal antibody production and purification.

A recombinant raccoonpox virus expresses one foreign gene. The feline CD80 gene lacking the transmembrane domain is under the control of the synthetic late/early pox promoter LP2EP2. Alternatively, the feline CD80 gene lacking the transmembrane domain has a histidine tag fusion at the carboxyl terminus to allow purification on a nickel affinity column.

A recombinant raccoonpox virus expresses one foreign gene. The feline Cd28 gene lacking the transmembrane domain is under the control of the synthetic late/early pox promoter LP2EP2. Alternatively, the feline CD28 gene lacking the transmembrane domain has a histidine tag fusion at the carboxyl terminus to allow purification on a nickel affinity column.

A recombinant raccoonpox virus expresses one foreign gene. The feline CD86 gene lacking the transmembrane domain is under the control of the synthetic late/early pox promoter LP2EP2. Alternatively, the feline CD86 gene lacking the transmembrane domain has a histidine tag fusion at the carboxyl terminus to allow purification on a nickel affinity column.

A recombinant raccoonpox virus expresses four foreign genes. The feline CD86- gene and the CD-80 gene expressed in a bicistronic cassette under the control of the synthetic late/early pox promoter LP2EP2, driving the transcription of CD80 and CD86 and including an EMCV IRES element between the two open reading frames driving the translation of the 2nd, downstream gene, CD80; the FIVgag gene is under the control of the swinepox promoter, OIL; the *E. coli* uidA gene is under the control of the synthetic early pox promoter E2.

A recombinant raccoonpox virus expresses four foreign genes. The feline CD86- gene and the CD-80 gene expressed in a bicistronic cassette under the control of the synthetic late/early pox promoter LP2EP2, driving the transcription of CD80 and CD86 and including an EMCV IRES element between the two open reading frames driving the translation of the 2nd, downstream gene, CD80; the FIVenvelope gene is under the control of the synthetic early pox promoter, E1; the *E. coli* uidA gene is under the control of the synthetic early pox promoter E2.

A recombinant raccoonpox virus expresses five foreign genes. The feline CD86- gene and the CD-80 gene expressed in a bicistronic cassette under the control of the synthetic late/early pox promoter LP2EP2, driving the transcription of CD80 and CD86 and including an EMCV IRES element between the two open reading frames driving the translation of the 2nd, downstream gene, CD80; the FIVgag gene is under the control of the swinepox promoter, OIL; the FIvenvelope gene is under the control of the synthetic early pox promoter, E1; the *E. coli* uidA gene is under the control of the synthetic early pox promoter E2.

Additional examples of recombinant raccoonpox virus useful as a vaccine against feline disease such as feline immunodeficiency virus (FIV), feline leukemia virus (FeLV), or feline infectious peritonitis (FIP) are:

A recombinant raccoonpox virus expresses two foreign genes. The feline CD86 gene is under the control of the synthetic late/early pox promoter LP2EP2; the *E. coli* lacZ gene is under the control of the synthetic late pox promoter LP1.

Additional examples of recombinant raccoonpox viruses utilizing both CD80 and CD86 and useful for vaccine developments for FIV and FeLV disease in fields are:

A recombinant raccoonpox virus expresses four foreign genes. The feline CD86 gene and the CD-80 gene expressed in a bicistronic cassette under the control of the synthetic late pox promoter LP1, driving the transcription of CD80 and CD86 and including an EMCV IRES element between the two open reading frames. The FIV gag/protease gene is under the control of the synthetic late/early pox promoter, LP2EP2; the *E. coli* uidA gene is under the control of the synthetic early pox promoter EP2. The CD80/CD86, FIVgag/protease and uidA genes are all inserted into a single non-essential RPV site.

A recombinant raccoonpox virus 4 foreign genes. The feline CD86- gene gene and the Cd-80 gene expresses in a bicistronic cassette under the control of the synthetic late/early pox promoter LP2, driving the transcription of CD80 and CD86 and including an EMCV IRES element between the two open reading frames; the *E. coli* lacZ gene is under the control of a synthectic early pox promoter, E1; the *E. coli* uidA gene is under the control of the synthetic early pox promoter E2. The CD80/CD86, FIV envelope and uidA genes are all inserted into a single non-assential RPV sites.

A recombinant raccoonpox virus expresses six foreign genes. The feline CD86 genes and the CD80 genes expressed in a bicistronic cassette under the control of the syntheti late pox promoter LP1, driving the transcription of CD80 and CD86 and including and EMCVIRIS element between the two open reading frames; the *E. coli* lacZ gene is under the control of a late pox promoter. The FIVgag/protease gene is on under the control of the synthetic early promoter, EP2; the FIV envelope gene is under the control of the synthetic early pox promoter, EP2; the FIV envelope gene is under the control of the synthetic early pox promoter, EPI; the *E. Coli* uidA gene is under the control of the *E. coli* lacZ genes are inserted into a destinct site from the insertion of the FIV envelope, FIVgag/protease and *E. coli* uidA gene insertion.

Additional raccoonpox recombinant viruses for use a FeLV vaccine for fields would be constructed as described above, replacing FIV genes for the comparable FeLV genes.

Example 12

S-FHV-020

S-FHV-020 is a recombinant feline herpesvirus that has a deletion of the entire FHV gE gene (1638 base pairs) an insertion of the *E. coli* lacZ gene is deleted gE site. The *E. coli* lacZ gene is under the transcriptional control of the constitutive FHV gE promoter.

S-FHV-020 was derived from S-FHV-001 (NVSL strain). This was accomplished utilizing the homology vector 486-88.B17 and virus S-FHV-001 in the HOMOLOGOUS RECOMBINATION PROCEDURE FOR GENERATING RECOMBINANT RPV, SPV OR FHV. the transfection stock was screened by the SCREEN FOR RECOMBINANT RPV OR SPV OR FHV EXPRESSING β-galactosidase (BLUOGAL AND CPRG ASSAYS) OR β-galactosidase (X-GLUC ASSAY). The final result of blue plaque purification was the recombinant virus designated S-FJV-020. Analysis of purity, and inserted stability after 5 passages was performed via detection of β-galactosidase in the SCREEN FOR FOREIGN GENE EXPRESSION IN RECOMBINANT RPV, SPV OR FHV USING BLACK PLAQUE ASSAYS.

Example 13

S-FHV-031

S-FHV-031 is recombinant feline herpesvirus that has a deletion of the entire 1638 base pair FHV gE gene and an insertion of three foreign genes in the gE deleted site. The CD80 gene is under the transcriptional control of the constitutive FHV gE promoter and oriented in the same direction as the deleted gE gene. The FIV gag/protease gene is under the control of the pseudorabies gX promoter and the FIV envelope gene is under the control of the cytomegalovirus immediate early promoter. The gag/protease and the envelope genes are oriented in the same direction with respect to each other, but opposite in orientation to the CD80 gene.

S-FHV-031 is derived from S-FHV-020 (contains the *E. coli* Lac Z gene behind gE promoter). This is accomplished utilizing the homology vector 942-03.C6 (see Materials and Methods) and virus S-FHV-020 in the HOMOLOGOUS RECOMBINATION RPV, SPV, OR FHV. The transfection stock is screened by the SCREEN FOR RECOMBINANT RPV OR SPV OR FHV EXPRESSING β-galactosidase in (BLUOGALAND CPRG ASSAYS) or β-glucuronidase (X-GLUCASSAY). Recombinant plaques are selected and purified by white plaque selection. This virus is characterised by restriction endonuclease mapping and the SOUTHERN BLOTTING DNA procedure. This analysis confirms the insertion of the feline CD80, FIV gag/protease and FIV envelope genes and the deletion of the 1638 base pair FIV gE gene. (PCT International Application WO 96/13575 is incorporated herein by reference)

S-FHV-031 in the present example is assayed for expression of feline CD80, FIV gag/protease and FIV envelope specific antigens using the WESTERN BLOTTING PROCEDURE. The assays described here were carried out in CRFK cells, indicating that CRFK cells would be a suitable subtrate for the production of FHV recombinant vaccines. The lysate from the recombinant feline herpesvirus infected cells exhibited band at the expected size of the feline CD80 protein. FIV gag/protease and FIV envelope.

S-FHV-031in the present example is assayed for expression of feline CD80-specific antigens using the SCREEN FOR FELINE CD80 (b7-1) and CD86 (B7-2) EXPRESSION IN RECOMBINANT SPV, RPV OR FHV USING BLACK PLAQUE ASSAYS. A human CTLA-4/Fc chimeric antibody is shown to react specifically with the recombinant feline herpesvirus plaques (expressing feline CD80) and not with SFHV-001 negative control plaques. All the recombinant feline herpesvirus observed plaques are shown to react with the human CTLA-4/Fc chimeric antibody indicating that the virus is stably expressing the feline CD80 foreign gene.

S-FHV-031 is a recombinant feline herpesvirus expressing the FIV gag/protease, FIV envelope and feline CD80 proteins and is useful as a vaccine in felids against FIV infection.

Example 14

A recombinant feline herpesvirus has a deletion of the gE gene and an insertion of at least one foreign gene at the gE deletion site. The foreign gene is the feline CD86 gene and is under the transcriptional control of the FHV gE promoter.

The recombinant feline herpesvirus expressing feline CD86 is useful as a vaccine against disease in felids. The recombinant feline herpesvirus improves the efficacy of vaccines against FIV, FeLV, FIP, or other feline diseases when used alone or in combination with FIV, FeLV, FIP, or other feline vaccines.

Example 15

Additional examples of recombinant feline herpesvirus useful as a vaccine against feline immunodeficiency virus (FIV), feline leukemia virus (FeLV) or feline infectious peritonitis (FIP) are:

A recombinant feline herpesvirus expresses three foreign genes. In the FHV gE delete sites. The FeLV env gene is under the control of the pseudorabies gX-promoter; the FIV gag gene is under the control of the cytomegalovirus immediate early promoter; the feline CD80 gene is under the control of the feline herpesvirus gE promoter. A recombinant feline herpesvirus expresses three foreign genes in the FHV gE deleted site. The FeLV env gene is under control of the pseudorabies gX promoter; the FIV gag gene is under the control of the cytomegalovirus immediate early promoter; the feline CD86 gene is under the control of the feline herpesvirus gE promoter. A recombinant feline herpesvirus expresses three foreign genes. In the FHV gE deleted site. The FeLV env gene is under the control of the pseudorabies gX promoter; the FeLV gag gene is under the control of the cytomegalovirus immediate early promoter; the feline CD86 gene is under the control of the feline herpesvirus gE promoter.

A recombinant feline herpesvirus expresses five foreign gene. The feline CD86 gene and the CD80 gene are expressed in a bicitronic cassette under the control of the cytomegalovirus immediate early promoter, driving the transcription of CD80 and CD86 and including an EMCV IRES element between the two open reading frames; the *E. coli* uidA gene is under the control of the infectious laryngotracheitis virus gl promoter. The CD80, CD86 and *E. coli* uidA gene are inserted into the unique long region of the FHV genome in a site determined to be non-essential. The FIV gag/protease gene is under the control of the cytomegalovirus immediate early promoter and the *E. coli* LacZ gene under the control of the pseudorabies gX promoter are inderted into the FHV gE deleted site.

A recombinant feline herpesvirus expressed five foreign genes. The feline cd86 and the CD80 genes are expressed in the bicitronic cassette under the control of cytomegalovirus immediate early promoter, driving the transcription of CD80 and cD86 Translation of the 2nd, downstream CD80 open reading frame is under the control of an EMCV IRES element. The *E. coli* uidA gene is under the control of the infectious laryngotracheitis virus gI promoter. The CD80, CD86, and *E. coli* uidA genes are inserted into the unique long region of the FHV genome in a site determined to be non-essential. The FIV envelope gene under the control of the cytomegalovirus immediate early promoter and the *E. coli* lacZ gene under the control of the pseudorabies gX promoter are inserted into the FHV gE deleted site.

A recombinant feline herpesvirus expresses six foreign genes. The feline CD86 gene and the CD80 genes are expressed in a bicistronic cassette under the control of the cytomegalovirus immediate early promoter, driving the transcription of CD80 and CD86 and including an EMCV IRES element between the two open reading frames. The *E. coli* uidA gene is under the control of the infectious laryngotracheitis virus gI promoter. The CD80, CD86, and *E. coli* uidA genes are inserted into the unique long reagent the FHV genome in a non-essential site. The FIV envelope gene under the control of the cytogelavirus immediate early promoter; the FIV gag/protease gene under the pseudorabies virus gX promoter and *E. coli* lacZ gene under the control of the FHV gE promoter are inserted into the FHV deleted site.

A recombinant feline herpesvirus expresses five foreign genes. The feline CD86 gene and the CD80 genes are expressed in a bicistronic cassette under the control of the cytomegalovirus immediate early promoter, driving the transcription of CD80 and CD86 and including an EMCV IRES element between the two open reading frames; the *E. coli* uidA gene is under the control of the infectious laryngotracheitis virus gI promoter. The CD80, CD86 and *E. coli* uidA genes are inserted into the unique long region of the FHV genome in a non-essential site. The FeLVgag/protease gene under the control of the cytomegalovirus immediate early promoter and the *E. coli* lacZ gene under the control of the pseudorabies gX promoter are inserted into the FHV gE deleted site.

A recombinant feline herpesvirus expresses five foreign genes. The feline CD86 gene and the CD80 genes are expressed in a bicistronic cassette under the control of the cytomegalovirus immediate early promoter, driving the transcription of CD80 and CD86 Translation of the 2nd, downstream CD80 open reading frame is under the control of an EMCV IRES element. The *E. coli* uidA gene is under the control of the infectious laryngotracheitis virus gI promoter. The CD80, CD86, and *E. coli* uidA genes are inserted into the unique region of the FHV genome in a non-essential site. The FeLV envelope gene under the control of the cytomegalovirus immediate early promoter and the *E. coli* lacZ gene under the control of the pseudorabies gX promoter are inserted into the FHV gE deleted site.

A recombinant feline herpesvirus expresses six foreign genes. The feline CD86 gene and the CD80 genes are expressed in bicistronic cassette under the control of the cytomegalovirus immediate early promoter, driving the transcription of CDBO and CD86 and including an EMCV IRES element between the two open frames. The *E. coli* uidA gene is under the control of the infectious laryngotracheitis virus gI promoter. The CD80, CD86, and *E. coli* uidA genes inserted into the unique longs region of the FHV genome in a non-essential site. The FeLVenvelope gene under the control of the cytomegalovirus immediate early promoter; the FeLVgag/protease gene under the pseudorabies virus gX promoter and *E coli* lacZ gene under the control of the FHV gE promoter are inserted into the FHV gE deleted site.

Example 17

A recombinant feline herpesvirus has a deletion of the gE gene and an insertion of at least one foreign gene at the gE deletion site. The foreign gene is the feline CD80 gene and is under the transcriptional control of the FHV gE promoter.

The recombinant feline herpesvirus is derived from S-FHV-001 (NVSL strain). This is accomplished utilizing the homology vector 926-76.D7 (see Materials and methods) and virus S-FHV-001 in the HOMOLOGOUS RECOMBINANT PROCEDURE FOR GENERATING RECOMBINANT HERPESVIRUS. The transfection stock is screened by the SCREEN FOR RECOMBINANT HERPESVIRUS EXPRESSING ENZYMATIC MARKER GENES. This virus is characterized by restriction endonuclease mapping and the SOUTHERN BLOTTING DNA procedure. This analysis confirms the insertion of the feline CD80 gene and the deletion of the 1638 base pair FHV gE gene. (PCT International Application WO 96/13575 is incorporated herein by reference.)

The recombinant feline herpesvirus in the present example is assayed for expression of feline CD80-specific antigens using the BLACK PLAQUE SCREEN FOR FOREIGN GENE EXPRESSION IN RECOMBINANT FHV. The assays described here were carried out in CRFK cells, indicating the CRFK cells would be a suitable substrate for the production of RPV recombinant vaccines.

The recombinant feline herpesvirus in the present example is assayed for expression of feline CD80-specific antigens using the SCREEN FOR FELINE CD80 (B7-1) and CD86 (B7-2) EXPRESSION IN RECOMBINANT SPV, RPV OR FHV USING BLACK PLAQUE ASSAYS. A human CTLA-4/Fc chimeric antibody is shown to react specifically with the recombinant feline herpesvirus plaques (expressing feline CD80) and not with S-FHV-001 negative control plaques. All the recombinant feline herpesvirus observed plaques are shown to react with the human CTLA-4/Fc chimeric antibody indicating that the virus is stably expressing the feline CD80 foreign gene.

To confirm the expression of the feline CD80 gene product, cells are infected with the recombinant feline herpesvirus of the present example and samples of infected cell lysates were subjected to SDS-polyacrylamide gel electrophoresis. The gel are blotted and analyzed using the WESTERN BLOTTING PROCEDURE. The lysate from the recombinant feline herpesvirus infected cells exhibited a band at the expected size of the feline CD80 protein.

Example 18 a recombinant feline herpesvirus has a deletion of the gE gene and an insertion of at least one foreign gene at the gE deletion site. The foreign gene is the feline CD86 gene and is under the transcriptional control of the FHV gE promoter.

The recombinant feline herpesvirus expressing feline CD86 is useful as a vaccine against disease in fields. The recombinant feline herpesvirus improves the efficacy of vaccines against FIV, FeLV, FIP, or other feline diseases when used alone or in combination with FIV, FeLV, FIP, or other feline vaccines.

Examples 19

Additional examples of recombinant feline herpesvirus useful as a vaccine against feline immunodeficiency virus (FIV), feline leukemia virus (FeLV) or feline infectious peritonitis (FIP) are:

A recombinant feline herpesvirus expresses three foreign genes. The FIV env gene is under the control of the pseudorabies gX promoter; the FIV gag gene is under the control of the cytomegalovirus immediate early promoter; the feline CD80 gene is under the control of the feline herpesvirus gE promoter.

A recombinant feline herpesvirus expresses three foreign genes. The FeLV env gene is under the control of the pseudorabies gX promoter; the FeLV gag gene is under the control of the cytomegalovirus immediate early promoter; the feline CD80 gene is under the control of the feline herpesvirus gE promoter.

A recombinant feline herpesvirus expresses three foreign genes. The FIV env gene is under the control of the pseudorabies gX promoter; the FIV gag gene is under the control of the cytomegalovirus immediate early promoter; the feline CD86 gene is under the control of the feline herpesvirus gE promoter.

A recombinant feline herpesvirus expresses three foreign genes. The FeLV env gene is under the control of the pseudorabies gX promoter; the FeLV gag gene is under the control of the cytomegalovirus immediate early promoter; the feline CD86 gene is under the control of the feline herpesvirus gE promoter.

A recombinant feline herpesvirus expresses five foreign genes. The feline CD86 gene and the CD80 genes are expressed in a bicistronic cassette under the control of the cytomegalovirus immediate early promoter, driving the transcription of CD80 and CD86 and including an EMCV IRES element between the two open reading frames driving the translation of the 2nd, downstream gene, CD80; *E. coli* uidA gene is under the control of the infection laryngotracheitis virus gI promoter; the FIVgag gene is under the control of cytomegalovirus immediate early promoter; the *E. coli* lacZ gene is under the control of the pseudorabies gX promoter. The five foreign genes are contained in two distinct feline herpesvirus insertion sites.

A recombinant feline herpesvirus expresses five foreign genes. The feline CD86 gene and the CD80 genes are expressed in a bicistronic cassette under the control of the cytomegalovirus immediate early promoter, driving the transcription of CD80 and CD86 Translation of the 2nd, downstream CD80 open reading frame is under the control of an EMCV IRES element; the *E. coli* uidA gene is under the control of the infectious laryngotracheitis virus gI promoter; the FIVenvelope gene is under the control of the cytomegalovirus immediate early promoter; the *E. coli* lacZ gene is under the control of the pseudorabies gX promoter. A recombinant feline herpesvirus expresses six foreign genes. The feline CD86 gene and the CD80 genes are expressed in a bicistronic cassette under the control of the cytomegalovirus immediate early promoter, driving the transcription of CD80 and CD86 and including an EMCV IRES element between the two open reading frames, driving the translation of the 2nd, downstream gene, CD80; the *E. coli* uidA gene is under the control of the infectious laryngotracheitis virus gI promoter; the FIVgag gene is under the control of the cytomegalovirus immediate early promoter; the FIVenvelope gene is under the control of the cytomegalovirus immediate early promoter; the *E. coli* lacZ gene is under the control of the pseudorabies gX promoter.

A recombinant feline herpesvirus expressed five foreign genes. The feline Cd86 gene and the CD80 genes are expressed in a bicistronic cassette under the control of the cytomegalovirus immediate early promoter, driving the transcription of CD80 and CD86 and including an EMCV IRES element between the two open reading frames driving the translation of the 2nd, downstream gene, CD80; the *E coli* uidA gene is under the control of the infectious laryngotracheitis virus gI promoter; the FeLVgag gene is under the control of the cytomegalovirus immediate early promoter; the *E. coli* lacZ gene is under the control of the pseudorabies gX promoter. The five foreign genes are contained in two distinct feline herpesvirus insertion sites.

A recombinant feline herpesvirus expressed five foreign genes. The feline CD86 gene and the CD80 genes are expressed in a bicistronic cassette under the control of the cytomegalovirus immediate early promoter, driving the transcription of CD80 and CD86 Translation of the 2nd, downstream CD80 open reading frame is under the control of an EMCV IRES element; the *E. coli* uidA gene is under the control of the infectious laryngotracheitis virus gI promoter; the FeLV envelope gene is under the control of the cytomegalovirus immediate early promoter; the *E. coli* lacZ gene is under the control of the pseudorabies gX promoter.

A recombinant feline herpesvirus expresses six foreign genes. The feline CD86 gene and the CD80 genes are expressed in a bicistronic cassette under the control of the cytomegalovirus immediate early promoter, driving the transcription of CD80 and CD86 and including an EMCV IRES element between the two open reading frames, driving the translation of the 2nd, downstream gene, CD80; the *E. coli* uidA gene is under the control of the infectious laryngotracheitis virus gI promoter; the FeLVgag gene is under the control of the cytomegalovirus immediate early promoter; the FeLV envelope gene is under the control of the cytomegalovirus immediate early promoter; the *E. coli* lacZ gene is under the control of the pseudorabies gX promoter.

Example 20

Characterization of the feline CD80 (B7-1)-TAMU, CD86 (B7-2), CD28, CTLA-4 and CD80 (B7-1)-Syntro/SPAH cDNAs and polypeptides:

The isolated and purified feline CD80 (B7-1) cDNA of approximately 941 nucleotides codes for an open reading frame of the feline CD80 polypeptide of approximately 292 amino acids, the native membrane bound or mature form of which has a molecular mass of about 33,485 kDa, an isoelectric point of about 9.1, a net charge at pH 7.0 of 10.24. The transmembrane domain of protein is approximately amino acids 241 to 271.

Feline CD80-TAMU and feline CD80-Syntro/SPAH are cDNAs and polypeptides isolated independently from two different sources, and the DNA and amino acid sequence differ slightly. The source of the CD80-TAMU mRNA was feline peripheral blood mononuclear cells stimulated with ConA, and the source of the CD80-Syntro/SPAH ,RNA was feline spleen cells stimulated with ConA. The difference in cDNA sequence between CD80-TAMU and CD80-Syntro/SPAH is T to C at nucleotide 351 and C to A at nucleotide 670. At the amino acid sequence, the change at nucleotide 351 is silent, and the change at nucleotide 670 results in a conservative change of neutral amino acids, leucine to isoleucine, at amino acid residue 224.

The isolated and purified feline CD86 (B7-2) cDNA of approximately 1176 nucleotides codes for an open reading frame of feline CD86 polypeptides of approximately 320 amino acids, the native membrane bound or mature form of which has a molecular mass of approximately 36,394 kDa, an isolectric point about 9.19, a net charge at pH 7.0 of 11.27.

The isolated and purified feline CD28 cDNA of approximately 689 nucleotides codes for an open reading frame of feline CD28 polypeptides of approximately 221 amino acids, the native membrane bound or mature form of which has a molecular mass of about 25,319 kDa, an isoelectric point of about 9.17, a net charge at pH 7.0 of 9.58.

The isolated and purified feline CTLA-4 cDNA of approximately 749 nucleotides codes for an open reading frame of feline CTLA-4 polypeptide of approximately 223 amino acids, the native membrane bound or mature form of which has a molecular mass of about 24,381 kDa, an isoelectric point of about 6.34, a net charge at pH 7.0 of −0.99.

The coexpression of CD80, with constimulatory molecules CD28 or CTLA-4, and a tumor antigen or an antigen from a pathogenic organism, has the ability to activate or enhance activation of T-lymphocyte, more specifically The-1 lymphocytes, and to promote the growth of other cell types. The coexpression of CD80, with constimulatory molecule CTLA-4, has the ability to suppress activation of T-lymphocytes, more specifically The-1 lymphocytes. The coexpression of CD86, with costimulatory molecules CD28 or CTLA-4, and a tumor antigen or an antigen from a pathogenic organism, has the ability to activate or enhance activation of T-lymphocytes, more specifically The-1 lymphocytes,and to promote the growth of other cell types. The coexpression of CD86, with costimulatory molecule CTLA-4, has the ability to suppress activation of T-lymphocytes,more specifically The-1 lymphocytes.

| DNA and Amino Acid Percentage Sequence Identity | Human Homologue (DNA Sequence) % Identity | Human Homologue (AA Sequence) % Identity | Mouse Homologue (DNA Sequence) % Identity | Mouse Homologue (AA Sequence) % Identity | Rabbit Homologue (DNA/AA Sequence) % Identity | Chicken Homologue (DNA/AA Sequence) % Identity |
|---|---|---|---|---|---|---|
| Feline CD80 | 77 | 59 | 62 | 46 | — | — |
| Feline CD86 | 72 | 68 | — | — | 67/64 | — |
| Feline CD28 | 85 | 82 | 77 | 74 | 84/84 | 59/50 |
| Feline CTLA-4 | 88 | 88 | 79 | 78 | — | — |

Example 21

Use of feline CD80 (B7-1), CD86 (B7-2), CD28, and CTLA-4 in Vaccines

The following experiments are performed to evaluate the immune-enhancing activities of feline CD80, CD86, CD28, and CTLA-4 in feline vaccines.

Feline CD80, CD86, CD28, and CTLA-4 are inserted into recombinant viral vectors (derived from feline herpesvirus, swinepox virus, or raccoonpox virus) useful for expression of recombinant proteins in felids (see PCT International Applications WO 96/22363 or WO 96/13575). The recombinant viral vectors expressing all four immune-enhancing molecules or alternatively, expressing pairwise combinations of CD80 and CD28, or CD80 and CTLA-4, or CD86 and CD28 or CD86 and CTLA-4 are administered orally or intramuscularly to cats at 8 weeks of age at a dosage range from 0.1 to 10.0 mg per kg body weight, or at a dosage of approximately $10^4$ to $10^9$ plaque forming units (pfu) or preferable at a dosage of approximately $10^6$ pfu. A subunit vaccine for FIV or FeLV or a viral vector vaccine for FIV or FeLV (see above) is administered at a minimum protective dose, simultaneously with the immune-enhancing feline CD80, CD86, CD28, and CTLA-4-vectored vaccine. Three to four weeks later the cats are given a second dose of the vaccine. The cats are challenged with a virulent FIV strain (PPR or Petaluma) or FeLV Rickard strain (administer with methylprednisolone to immune-suppress the cats) at the USDA standard challenge dosage level and are observed regularly for 12 weeks for development of viremia. A group of vaccinated cats are observed for up to 12 months for the development of tumors caused by FeLV. The incidence of disease in cats is compared with controls that receive no vaccine, or FIV or FeLV vaccine without immune enhancing molecules. The results of the challenge experiment are that cats receiving no vaccine and then challenged with FeLV or FIV, greater than 60% develop persistent viremia; cats vaccinated with the subunit FIV or FeLV vaccine, and then challenged, 75% are protected from viremia; cats receiving the subunit FIV or FeLV vaccine and a combination of the immune-enhancing feline CD80, CD86, CD28, and CTLA-4-vectored vaccine and then challenged, 100% are protected from viremia. Additional beneficial aspects of adding the feline CD80, CD86, CD28, and CTLA-4-vectored vaccine is 100% protection against viremia and/or tumor formation; long duration of immunity (greater than 1 year); early onset of immunity; or single dose primary vaccination instead of the 2 doses now required by all manufacturers. Cats vaccinated with the viral vectored FIV or FeLV vaccines are protected from challenge at a level significantly higher than cats vaccinated with a subunit FIV or FeLV vaccine. Cats receiving the viral vectored FIV or FeLV vaccine and a combination of the immune-enhancing feline CD80, CD86, CD28, and CTLA-4-vectored vaccine and then challenged, 100% are protected from viremia. Cats vaccinated with the viral vectored FIV or FeLV vaccine and a combination of the immune-enhancing feline CD80, CD86, CD28, and CTLA-4-vectored vaccine also receive the additional beneficial aspects described above.

In an alternate procedure, cats at 8 weeks of age are injected intramuscularly with 100 µg of plasmid containing cDNA for feline CD80, CD86, CD28, and CTLA-4 molecules in a mixture with a plasmid containing cDNA for FIV env and gag or FeLV env and gag, or alternatively, injected intramuscularly with 100 µg of plasmid containing cDNA expressing pairwise combinations of CD80 and CD28, or CD80 and CTLA-4, or CD86 and CD28 or CD86 and CTLA-4 paired with CD28 or CTLA-4, in a mixture with a plasmid containing cDNA for FIV env and gag or FeLV env and gag. Control cats do not receive CD80, CD86, CD28, and CTLA-4. Cats are challenged with virulent FeLV or FIV and observed for signs of disease as described above. The results of the challenge experiment are that cats receiving the cDNA vector containing feline CD80, CD86, CD28, and CTLA-4 and cDNA vector containing FIV genes or FeLV genes show 100% protection from disease compared to cats receiving only cDNA vector containing FIV genes or FeLV genes who show 75% protection from disease.

In an alternate procedure, cats at 8 weeks of age are injected intramuscularly with 0.1 to 100 mg of purified protein for feline CD80, CD86, CD28, and CTLA-4 molecules or alternatively, pairwise combinations of CD80 or CD86 paired with CD28 or CTLA-4 proteins, from recombinant cDNA vectors described above, and injected intramuscularly with 0.1 to 100 mg of a subunit vaccine containing FIV env and gag or FeLV env and gag. Control cats do not receive CD80, CD86, CD28, and CTLA-4. Cats are challenged with a virulent FIV strain or FeLV strain and observed regularly for development of disease. The results of the challenge experiment are that cats receiving the purified protein for feline CD80, CD86, CD28, and CTLA-4 and subunit vaccine containing FIV or FeLV show significantly reduced incidence of disease compared to cats receiving only subunit vaccine containing FIV or FeLV proteins.

Example 22

Use of feline CD80, CD86, CD28, and CTLA-4 as a prophylactic vaccine for disease protection Feline CD80, CD86, CD28, and CTLA-4 in a recombinant swinepox, recombinant raccoonpox, or recombinant feline herpes viral vectors when administered as described in Example 17, but without administering subunit or viral vectored antigens from pathogenic organisms, are useful to stimulate immunity and a The-1 response which elicits a protective immune response when challenged with a viral, parasitic or bacterial pathogen. In an alternate procedure, feline CD80 or CD86, in combination with feline CTLA-4 in viral vectors when administered as described in Example 3, are useful to suppress an immune response, and protect against autoimmune disease in cats.

Example 23

Use of feline CD80, CD86, CD28, and CTLA-4 to inhibit and destroy tumor cell growth.

Tumor cells from a cat are transfected with a recombinant swinepox, recombinant raccoonpox, or recombinant feline herpes viral vector expressing feline CD80 or CD86 in combination with CD28 or CTLA-4. The transfected tumor cells are re-administered to the cat, and the presence of the CD80, CD86, CD28, and CTLA-4 on the surface of the tumor cell raises a broad immunological response to transfected and non-transfected tumor cells resulting in killing of localized and metastatic tumor cells. In an alternate procedure, vectors expressing feline CD80 or CD86 in combination with CD28 or CTLA-4 are injected directly into a tumor in a cat resulting in a broad immunological response to the tumor cells resulting in killing of localized and metastatic tumor cells.

Example 24

Use of feline CD80, CD86, CD28, and CTLA-4 as a therapeutic to treat disease in cats.

Feline CD80, CD86, CD28, and CTLA-4 in a recombinant swinepox, recombinant raccoonpox, or recombinant feline herpes viral vector when administered as described in Example 17, but without administering subunit or viral vectored antigens from pathogenic organisms, are useful to stimulate immunity to clear or reduce the level of disease pathology.

Supporting Experimental Data: SPV 246

Safety and Efficacy of a recombinant viral vectored SPV vaccine containing FeLV gag and envelope and feline CD80.

The construction of the recombinant SPV virus, SPV 246, was described above (in the body of the original filing). SPV 246 contains five foreign genes including genes encoding for FeLV gag and envelope and feline CD80 as well as two marker genes, β-glucuronidase and β-galactosidase. Expression of FeLV gag and envelope and CD80 in cells infected with SPV 246 was confirmed by WESTERN BLOT analysis. Bands representing the specific FeLV gag and envelope proteins were detected with a goat polyclonal antibody against FeLV P27 (Biodesign, ME) and a monoclonal antibody against FeLV gp70 (Biodesign, ME), respectively. FeLV gag and envelope proteins appeared to be postranslationally processed similarly to native viral proteins. Purity, expression and stability analysis was carried out by BLACK PLAQUE Assay utilizing the antibodies described above. SPV 246 was stably passaged at least 5 times. 100% of plaques generated from cells infected with SPV 246, were positive for FeLVgag, envelope, β-galactosidase and β-glucuronidase.

The expression of feline CD80 was confirmed in WESTERN BLOT analysis using a polyclonal anti-human CD80 antibody. Multiple bands ranging in size from 30 kda to 60 kda specific for feline CD80 were detected. These bands represent alternate and multiple glycosylation patterns of CD80 expressed and modified in the context of SPV and ESK-4 cells.

SPV 246 and control virus, SPV 003, as well as other recombinant FHV and SPV FeLV vaccine candidates were tested for their ability to protect cats against FeLV persistent infection. In short, 8-week old kittens, 10 cats/group, were vaccinated subcutaneously with 1 ml of SPV 246, control virus or other recombinant viruses (doses ranged from $7\times10^5$ pfu/cat to $1\times10^7$ pfu/cat. Cats were vaccinated 3 times, 3 weeks apart. Following vaccinations, cats were challenged by oro-nasal route with the Rickard FeLV standard challenge strain ($10^{6.2}$ $TCID_{50}$/ml/cat) , after pre-treatment with methylprednisolone acetate (Depo-Medrol).

Serum from cats was analyzed for persistent viremia on a weekly basis for 15 weeks post challenge. Cats were considered to be persistently viremic after testing positive for the presence of FeLV p27 for 3 consecutive weeks.

Results:

Cats vaccinated with SPV 246 were partially protected from FeLV viremia in an FeLV challenge study. The predicted preventable fraction (PF) value for cats treated with SPV 246 was 50% (Table 1).

TABLE 1

Number and percentage of cats with persistent viremia at 15 weeks post challenge. Predicted Preventable Fraction (PF) for each group was calculated.

| GROUP # | VIRUS (ES) | # cats with persistent viremia | % cats with persistent viremia | PF (%C–%V) % C |
|---|---|---|---|---|
| 1 | FHV 018 (CMV-FeLVenv)<br>FHV 019 (CMV FeLVgag) | 7/10 | 70% | −16% |
| 2 | FHV 018 (CMV-FeLVenv)<br>FHV 019 (CMV-FeLVgag)<br>FHV 030 (gE-CD80) | 6/10 | 60 | 0% |
| 3 | FHV 018 (CMV-FeLVenv)<br>FHV 019 (CMV-FeLVgag)<br>RPV 022 (L2E2-CD80) | 7/10 | 70 | −16% |

TABLE 1-continued

Number and percentage of cats with persistent viremia at 15 weeks post challenge. Predicted Preventable Fraction (PF) for each group was calculated.

| GROUP # | VIRUS (ES) | # cats with persistent viremia | % cats with persistent viremia | PF (%C–%V) % C |
|---|---|---|---|---|
| 4 | SPV 089 (L2E2-FeLVgag)<br>SPV 195 (E1-FeLVenv)<br>FHV 030 (gE-CD80) | 5/10 | 50 | 16% |
| 5 | SPV 246 (E2-FeLVgag/E1 -FeLVenv//L2E2 -CD80) | 3/10 | 30 | 50% |
| 6 (SC) | SPV 258 (L2E2-FeLVgag/L2E2-FeLVgp70)<br>FHV 030 (gE-CD80) | 5/10 | 50 | 16% |
| 7 (IM) | SPV 258 (L2E2-FeLVgag/L2E2-FeLVgp70)<br>FHV 030 (gE-CD80) | 6/10 | 60 | 0 |
| 8 | SPV 003, FHV 005 | 6/10 | 60% | 0 |

EXAMPLES OF ADDITIONAL RECOMBINANT VIRUSES CONTAINING CD80 and CD86

SPV 280

SPV 280 is a recombinant swinepox virus expressing six foreign genes. A homology vector designated 992-23.6 was constructed in the following way: the feline CD86 gene and the CD80 gene were expressed in a bicistronic DNA cassette under the control of the synthetic late pox promoter, LP1, driving the transcription of CD80 and CD86 and including an EMCV IRES element between the two open reading frames; the *E. coli* β-glucuronidase gene is under the control of the synthetic early promoter, EP2. SPV 280 was derived from SPV 258, which contains the genes for FeLVgag and envelope and β-galactosidase. SPV 258 was previously engineered to contain the FeLV gag/protease genes, and the truncated FeLV envelope (gp70) gene under the control of the synthetic early/late pox promoters, LP2EP2; the *E. coli* β-galactosidase gene is under the control of the constitutive I5L pox promoter and inserted into the deleted 1869 bp partial HindIII N fragment. The CD80/CD86 and *E coli* β-glucuronidase genes were cloned into the homology vector, 992-23.6 in a distinct and non-essential SPV partial Hind III K fragment.

SPV 280 was derived from SPV 258. This was accomplished utilizing the homology vector 992-23.6 and virus S-SPV-258 in the HOMOLOGOUS RECOMBINATION PROCEDURE FOR GENERATING RECOMBINANT RPV, SPV, OR FHV. The transfection stock was screened by the SCREEN FOR RECOMBINANT SPV EXPRESSING β-galactosidase (BLUOGAL and CPRG ASSAYS) or β-glucuronidase (X-GLUC ASSAY). The final result of multiple rounds of blue/green plaque purification was the recombinant virus SPV 280.

SPV 280 was assayed for expression of FeLVgag, FeLV envelope and the marker genes, β-galactosidase and β-glucuronidase by BLACK PLAQUE Analysis. 100% of plaques generated from ESK-4 cells infected with purified SPV 280 were determined to be expressing FeLVgag and FeLV envelope, using a goat polyclonal antibody for FeLV-gag (Biodesign, ME) and a mouse monoclonal antibody for FeLV envelope, gp70 (Biodesign, ME).

The expression of feline CD80 and CD86 was confirmed in WESTERN BLOT analysis using goat polyclonal anti-human CD80 and CD86 antibodies (R&D Systems, MN), respectively. Multiple bands ranging in size from 30 kda to 60 kda specific for feline CD80 were detected, and multiple bands ranging from 40 kda to 70 kda specific for feline CD86 were detected. These bands represent alternate and multiple glycosylation patterns of CD80 and CD86 expressed in the context of SPV in ESK-4 cells.

SPV 281

SPV 281 is a recombinant swinepox virus expressing six foreign genes. A homology vector designated 992-23.6 was constructed as described above for SPV 280. SPV 281 was derived from SPV 228, which contains the genes for FIVgag/protease and envelope and *E. coli* β-galactosidase. The FIV gag/protease gene is under the control of a synthetic pox early promoter, EP2; the FIVenvelope gene is under the control of a synthetic pox early promoter, EP1; the *E. coli* β-galactosidase gene is under the control of the constitutive I5L pox promoter. FIVgag/protease , envelope and *E. coli* β-galactosidase were inserted into the deleted 1869 bp partial Hind III N fragment of SPV. The CD80/CD86 and *E. coli* β-glucuronidase genes were inserted into the distinct and non-essential SPV partial Hind III K fragment.

SPV 281 was derived from SPV 228. This was accomplished utilizing the homology vector 992-23.6 and virus S-SPV-228 in the HOMOLOGOUS RECOMBINATION PROCEDURE FOR GENERATING RECOMBINANT RPV, SPV, OR FHV. The transfection stocks were screened by the SCREEN FOR RECOMBINANT SPV EXPRESSING β-galactosidase (BLUOGAL and CPRG ASSAYS) or β-glucuronidase (X-GLUC ASSAY) METHOD. The final result of multiple rounds of blue/green plaque purification was the recombinant virus SPV 281.

SPV 281 was assayed for expression of FIVgag, FIV envelope and the marker genes, β-galactosidase and β-glucuronidase by BLACK PLAQUE Analysis. 100% of plaques from ESK-4 cells infected with plaque purified SPV 281 were determined to be expressing FIVgag, FIV envelope, β-galactosidase and β-Glucuronidase utilizing mouse monoclonal antibodies for FIVgag (p27) and FIV envelope (gp100) (Custom Monoclonals, CA; BioDesign International, ME, respectively), a mouse monoclonal to β-galactosidase and a rabbit polyclonal antibody to β-glucuronidase (Biodesign, ME and Molecular Probes, OR, respectively).

The expression of feline CD80 and CD86 was confirmed in WESTERN BLOT analysis utilizing polyclonal anti-human CD80 and CD86 antibodies (R&D Systems, MN). Multiple bands ranging in size from 30 kda to 60 kda specific for feline CD80 were detected, and multiple bands ranging from 40 kda to 70 kda specific for feline CD86 were detected. These bands represent alternate and multiple glycosylation patterns of CD80 and CD86 expressed in the context of SPV in ESK-4 cells. FIV gag and envelope expression was also confirmed by WESTERN BLOT analysis utilizing the antibodies described above. FIV gag and envelope appeared to be processed into P24 and gp 100, respectively.

FHV 043

FHV 043 is a recombinant feline herpes virus expressing five foreign genes. A homology vector designated 987-57.A1 was constructed in the following way: the feline CD86 and CD80 genes were cloned into a bicistronic cassette under the control of the cytomegalovirus immediate early promoter (CMV IE), driving the transcription of CD80 and CD86. Translation of the 2nd downstream CD80 open reading frame was under the control of the EMCV IRES element. The *E. coli* β-glucuronidase gene is under the control of the infectious laryngotracheitis virus gI promoter. The CD80, CD86, and *E. coli* β-glucuronidase genes were inserted into the FHV unique long region in a unique EcoRI site derived from a partial Sal I H fragment of FHV. The insertion was between the gL and adjacent transcriptional activator genes.

FHV 043 was derived from FHV 017, which contains the genes for FIV envelope and *E. coli* β-galactosidase. The FIVenvelope gene is under the control of the CMV IE promoter; and the *E. coli* β-galactosidase gene is under the control of the pseudorabies gX promoter element. FIV envelope and *E. coli* β-galactosidase were inserted into the FHV US gE deleted site.

FHV 043 was derived from FHV 017. This was accomplished by utilizing the homology vector 987-57.A1 and virus FHV 017 in the HOMOLOGOUS RECOMBINATION PROCEDURE FOR GENERATING RECOMBINANT RPV, SPV, OR FHV. The transfection stocks were screened by the SCREEN FOR RECOMBINANT SPV EXPRESSING β-galactosidase (BLUOGAL and CPRG ASSAYS) or β-glucuronidase (X-GLUC ASSAY) METHODS. The final result of multiple rounds of blue/green plaque purification was the recombinant virus FHV 043.

FHV 043 was assayed for expression of the marker genes, β-galactosidase and β-glucuronidase by BLACK PLAQUE Analysis. 100% of plaques from CRFK cells infected with plaque purified FHV 043 were determined to be expressing β-galactosidase and β-glucuronidase, utilizing a mouse monoclonal antibody to β-galactosidase (Biodesign, ME) and a rabbit polyclonal antibody to β-glucuronidase (Molecular Probes, OR). This virus was determined to be stable after at least 5 passages.

The expression of feline CD80 and CD86 was confirmed in WESTERN BLOT analysis utilizing polyclonal anti-human CD80 and CD86 antibodies (R&D Systems, MN). Multiple bands ranging in size from 30 kda to 60 kda specific for feline CD80 were detected, and multiple bands ranging from 40 kda to 70 kda specific for feline CD86 were detected. The expression of FIV envelope (gp103) was confirmed in WESTERN BLOT analysis utilizing a convalescent cat sera from an FIV infected cat.

HOMOLOGY VECTOR 1015-18.8A (LP1-CD86/IRES-CD80):

The homology vector 1015-18.8A was used to create recombinant RPV viruses expressing CD80 and CD86: A plasmid was constructed containing the pox LP1 promoter, EMCV IRES element, and a pox Poly A transcriptional terminator. The feline CD80 gene was PCR amplified with primers 1/97.6 (5'-GCTAGGATCCAATCTATGTAGACAGGTGAGAT-3') and 3/98.4 (5'-TCGAGGATCCGGGTCACGCAGCAAAGTGG-3'), both containing BamHI cloning sites. CD80 was cloned behind the LP1 promoter. The feline CD86 gene was PCR amplified with primers 1/98.18 (5'-TCGACAATTGGATGGGCATTTGTGACAG-3') with an MfeI cloning site and 8/97.31 (5'-GTGGATCCAGGATCCGGAGCGG-3') blunt ended. CD86 was cloned behind the EMCV IRES element. The cassette was then digested with NotI and cloned into the RPV HindIII N vector containing the *E. coli* β-galactosidase gene under the control of the synthetic late promoter, I5L. The final homology vector 1015-18.8A was used to create viruses containing FIV or FeLV genes and CD80 and CD86 according to the HOMOLOGOUS RECOMBINATION PROCEDURE FOR GENERATING RECOMBINANT RPV.

S-RPV-045:

S-RPV-045 is a recombinant raccoonpox virus expressing three foreign genes. S-RPV-045 was derived from the raccoonpox virus RPV-000 (ATCC VR-838). This was accomplished utilizing the homology vector 1015-18.8A and the parental virus S-RPV-000 in the HOMOLOGOUS RECOMBINATION PROCEDURE FOR GENERATING RECOMBINANT RPV. The transfection stocks were screened for the recombinant by the SCREEN FOR RECOMBINANT RPV EXPRESSING β-galactosidase (BLUO-GAL ASSAYS and SCREEN FOR RECOMBINANT RPV EXPRESSING ENZYMATIC MARKER GENES). The virus was plaque purified and passaged 5 times.

RPV-045 was assayed for β-galactosidase expression by Black Plaque Analysis. 100% of plaques generated from VERO cells infected with purified RPV-045 were determined to be expressing β-galactosidase, using a rabbit polyclonal antibody (ICN, OH).

Western analysis using the WESTERN BLOTTING PROCEDURE confirmed the expression of CD80 and CD86 using goat polyclonal anti-human CD80 and CD86 antibodies (R&D Systems, MN), respectively. Multiple bands ranging in size from 30 to 60 kda specific for feline CD80 were detected, and multiple bands ranging from 40 to 70 kda specific for feline CD86 were detected. These bands represent alternate and multiple glycosylation patterns of CD80 and CD86 expressed in the context of RPV in VERO cells.

S-RPV-046:

RPV-046 is a raccoonpox virus expressing five foreign genes. RPV-046 was derived from the raccoon poxvirus RPV-036. This was accomplished utilizing the homology vector 1015-18.8A and the parental virus RPV-036 in the HOMOLOGOUS RECOMBINATION PROCEDURE FOR GENERATING RECOMBINANT RPV. The transfection stocks were screened for the recombinant by the SCREEN FOR RECOMBINANT RPV EXPRESSING β-galactosidase (BLUO-GAL ASSAYS and SCREEN FOR RECOMBINANT RPV EXPRESSING ENZYMATIC MARKER GENES). The virus was plaque purified and passaged 5 times. The final result of multiple rounds of blue/green plaque purification was the recombinant virus FHV 046. RPV 046 contains the FIV gag gene under the control of the synthetic early/late pox promoter, LP2EP2, and the β-glucuronidase gene under the control of the synthetic early pox promoter, EP2. These genes are contained in the distinct and non-essential partial RPV HindIII U site. The CD80 and CD86 genes and the β-galactosidase are contained in the unique and distinct non-essential partial RPV HindIII N site.

RPV-046 was assayed for β-galactosidase and β-glucuronidase expression by Black Plaque Analysis. 100% of plaques generated from Vero cells infected with purified RPV-046 were determined to be expressing β-galactosidase and β-glucuronidase.

Western analysis using the WESTERN BLOTTING PROCEDURE confirmed the expression of CD80 and CD86 using goat polyclonal anti-human CD80 and CD86 antibodies (R&D Systems, MN), respectively. Multiple bands ranging in size from 30 to 60 kda specific for feline CD80 were detected, and multiple bands ranging from 40 to 70 kda specific for feline CD86 were detected. These bands represent alternate and multiple glycosylation patterns of CD80 and CD86 expressed in the context of RPV in VERO cells. FIVgag/protease expression was also confirmed by WESTERN BLOT analysis utilizing mouse monoclonal antibodies for FIVgag (p27) (Custom Monoclonals, CA).

S-RPV-047:

RPV-047 is a raccoonpox virus expressing five foreign genes. The 1015-18.8A homology vector was constructed as described above which contains the LP1-CD86/IRES-CD80 cassette and the *E. coli* β-galactosidase gene under the control of the synthetic late promoter (I5L) in the HindIII N fragment. RPV-047 was derived from RPV-044, which contains the genes for FIVenv and the *E. coli* β-glucuronidase (β-glucuronidase) in the RPV HindIII U fragment. The FIVenv gene is under the control of the synthetic early promoter (EP1). The β-glucuronidase gene is under the control of the synthetic late promoter (LP1).

RPV-047 was derived from the raccoon poxvirus RPV-044. This was accomplished utilizing the homology vector 1015-18.8A and the parental virus RPV-044 in the HOMOLOGOUS RECOMBINATION PROCEDURE FOR GENERATING RECOMBINANT RPV. The transfection stocks were screened for the recombinant by the SCREEN FOR RECOMBINANT RPV EXPRESSING β-galactosidase (BLUO-GAL ASSAYS and SCREEN FOR RECOMBINANT RPV EXPRESSING ENZYMATIC MARKER GENES). The virus was plaque purified and passaged 5 times. The final result of multiple rounds of blue/green plaque purification was the recombinant virus FHV 047.

RPV-047 was assayed for β-galactosidase expression by Black Plaque Analysis. 100% of plaques generated from Vero cells infected with purified RPV-047 were determined to be expressing β-galactosidase, using a rabbit polyclonal antibody (ICN, OH).

Western analysis using the WESTERN BLOTTING PROCEDURE confirmed the expression of CD80 and CD86 using goat polyclonal anti-human CD80 and CD86 antibodies (R&D Systems, MN) , respectively. Multiple bands ranging in size from 30 to 60 kda specific for feline CD80 were detected, and multiple bands ranging from 40 to 70 kda specific for feline CD86 were detected. These bands represent alternate and multiple glycosylation patterns of CD80 and CD86 expressed in the context of RPV in VERO cells. FIVenv expression was also confirmed by WESTERN BLOT analysis utilizing mouse monoclonal antibodies for FIVenv (gp100) (BioDesign International, ME) S-RPV-048:

RPV-048 is a raccoonpox virus expressing five foreign genes. The 1015-18.8A homology vector was constructed as described above which contains the LP1-CD86/IRES-CD80 cassette and the *E. coli* β-galactosidase gene under the control of the synthetic late promoter (I5L) in the HindIII N fragment. RPV-048 was derived from RPV-038, which contains the genes for FeLvgag/protease and the *E. coli* β-glucuronidase in the RPV HindIII U fragment. The FeLVgag/protease gene is under the control of the synthetic late/early promoters (LP2EP2). The β-glucuronidase gene is under the control of the synthetic late promoter (LP1).

RPV-048 was derived from the recombinant raccoon poxvirus RPV-038. This was accomplished utilizing the homology vector 1015-18.8A and the parental virus RPV-038 in the HOMOLOGOUS RECOMBINATION PROCEDURE FOR GENERATING RECOMBINANT RPV. The transfection stocks were screened for the recombinant by the SCREEN FOR RECOMBINANT RPV EXPRESSING β-galactosidase (BLUO-GAL ASSAYS and SCREEN FOR RECOMBINANT RPV EXPRESSING ENZYMATIC MARKER GENES). The virus was plaque purified and passaged 5 times. The final result of multiple rounds of blue/green plaque purification was the recombinant virus FHV 048.

RPV-048 was assayed for β-galactosidase expression by Black Plaque Analysis. 100% of plaques generated from Vero cells infected with purified RPV-046 were determined to be expressing β-galactosidase, using a rabbit polyclonal antibody (ICN, OH).

Western analysis using the WESTERN BLOTTING PROCEDURE confirmed the expression of CD80 and CD86 using goat polyclonal anti-human CD80 and CD86 antibodies (R&D Systems, MN), respectively. Multiple bands ranging in size from 30 to 60 kda specific for feline CD80 were detected, and multiple bands ranging from 40 to 70 kda specific for feline CD86 were detected. These bands represent alternate and multiple glycosylation patterns of CD80 and CD86 expressed in the context of RPV in VERO cells. FeLVgag/protease expression was also confirmed by WESTERN BLOT analysis utilizing rabbit polyclonal antibodies for FeLVgag (p27) (BioDesign International, ME).

S-RPV-052:

RPV-052 is a raccoonpox virus expressing six foreign genes. The 1015-18.8A homology vector was constructed as described above which contains the LP1-CD86/IRES-CD80 cassette and the *E. coli* β-galactosidase gene under the control of the synthetic late promoter (I5L) in the HindIII N fragment. RPV-052 was derived from RPV-030, which contains the genes for FeLVgag/protease, FeLVenv, and the *E. coli* β-glucuronidase (β-glucuronidase) in the RPV HindIII U fragment. The FeLVgag/protease gene is under the control of the synthetic early promoter (EP2). The FeLVenv gene is under the control of the synthetic early promoter (EP1). The β-glucuronidase gene is under the control of the synthetic late promoter (LP1).

RPV-052 was derived from the raccoon poxvirus RPV-030. This was accomplished utilizing the homology vector 1015-18.8A and the parental virus RPV-030 in the HOMOLOGOUS RECOMBINATION PROCEDURE FOR GENERATING RECOMBINANT RPV. The transfection stocks were screened for the recombinant virus by the SCREEN FOR RECOMBINANT RPV EXPRESSING β-galactosidase (BLUO-GAL ASSAYS and SCREEN FOR RECOMBINANT RPV EXPRESSING ENZYMATIC MARKER GENES). The virus was plaque purified and passaged 5 times. The final result of multiple rounds of blue/green plaque purification was the recombinant virus FHV 052.

RPV-052 was assayed for β-galactosidase, β-glucuronidase, FeLV gag and FeLV envelope expression by the Black Plaque Analysis. Western analysis using the WESTERN BLOTTING PROCEDURE confirmed the expression of CD80 and CD86 using goat polyclonal anti-human CD80 and CD86 antibodies (R&D Systems, MN), respectively. Expression of FeLVgag/protease and FeLV envelope was also confirmed by WESTERN BLOT analysis utilizing rabbit polyclonal antibodies for FeLVgag (p27) (BioDesign International, ME) and mouse monoclonal anti-FeLV env (gp100) (BioDesign, ME).

S-RPV-053:

RPV-053 is a raccoonpox virus expressing six foreign genes. The 1015-18.8A homology vector was constructed as described above which contains the LP1-CD86/IRES-CD80 cassette and the *E. coli* β-galactosidase gene under the control of the synthetic late promoter (I5L) in the HindIII N fragment. RPV-053 was derived from RPV-034, which contains the genes for FIVgag/protease, FIVenv, and the *E. coli* β-glucuronidase in the RPV HindIII U fragment. The FIVgag/protease gene is under the control of the synthetic early promoter (EP2). The FIVenv gene is under the control of the synthetic early promoter (EP1). The β-glucuronidase gene is under the control of the synthetic late promoter (LP1).

RPV-053 was derived from the raccoon poxvirus RPV-034. This was accomplished utilizing the homology vector 1015-18.8A and the parental virus RPV-034 in the HOMOLOGOUS RECOMBINATION PROCEDURE FOR GENERATING RECOMBINANT RPV. The transfection stocks were screened for the recombinant by the SCREEN FOR RECOMBINANT RPV EXPRESSING β-galactosidase (BLUO-GAL ASSAYS and SCREEN FOR RECOMBINANT RPV EXPRESSING ENZYMATIC MARKER GENES). The virus was plaque purified and passaged 5 times. The final result of multiple rounds of blue/green plaque purification was the recombinant virus FHV 053.

S-SPV 275:

S-SPV-275 is a recombinant swinepox virus that expresses five foreign genes. A homology vector designated 992-23.6 was constructed as follows: the feline CD86 and the CD80 genes were expressed in a bicistronic DNA cassette under the control of the synthetic late pox promoter, LP1, driving the transcription of both CD86 and CD80, and included an EMCV IRES element between the two open reading frames. The *E. coli* β-glucuronidase gene is under the control of the synthetic pox early promoter, EP2. The parent virus used was S-SPV 046, which contains the FIV gag/protease gene promoted by the synthetic late/early pox promoter, LP2EP2 and the β-galactosidase gene is under the control of the constitutive pox promoter, O1L. The FIV gag/protease, and β-galactosidase genes were inserted into the SPV partial Hind III M fragment, while the CD86/CD80 and β-glucuronidase genes were inserted into the SPV partial Hind III K fragment.

S—SPV 275 was derived from S—SPV 046. This was accomplished utilizing the homology vector 992-23.6 and S—SPV 046 in the HOMOLOGOUS RECOMBINATION PROCEDURE FOR GENERATING RECOMBINANT SPV. The transfection stock was screened by the SCREEN FOR RECOMBINANT SPV EXPRESSING b-glucuronidase (X-GLUC ASSAY). The final result of multiple rounds of purification for green/blue plaques was the recombinant virus SPV 275.

S—SPV 275 was assayed for expression of FIV gag, and the marker gene, β-glucuronidase by BLACK PLAQUE Assay. 100% of the plaques generated in ESK-4 cells infected with purified S—SPV 275 were determined to be expressing FIV gag using a mouse monoclonal antibody for FIV gag (Custom Monoclonals, CA), and is stable after 5 passages.

The expression of FIV gag, CD86, and CD80 was confirmed in WESTERN BLOT analysis using the mouse monoclonal for FIV gag, and goat polyclonal anti-human CD86 and CD80 antibodies (R&D Systems; MN) for Feline CD86 and CD80. Two distinct band were detected at the 50 kDa and 27 kDa specific for FIV gag. Multiple bands ranging from 40 kDa to 70 kDa specific for Feline CD86 were detected, and so were bands ranging from 30 kDa to 60 kDa specific for Feline CD80 were detected.

S–FHV 040:

S–FHV 040 is a recombinant feline herpes virus expressing five foreign genes. A homology vector designated 957-87.A1 was constructed in the following way: The feline CD80 and CD86 genes were expressed in a bicistronic DNA cassette under the control of the cytomegalovirus immediate early promoter (CMV IE), driving the transcription of CD80 and CD86, and included an EMCV IRES element between the two open reading frames. The β-glucuronidase gene is under the control of the infectious laryngotracheitis virus gI promoter. CD80, CD86, and the β-glucuronidase genes were inserted into the FHV unique long region in a unique EcoRI site derived from a partial Sal I H fragment of FHV, between the gL and adjacent transcriptional activator genes. The parent virus used was S–FHV 019 which contains the CMV IE promoted FeLV gag gene, and *E. coli* β-galactosidase gene which is under the pseudorabies gX promoter; both genes are located in the FHV unique short (US) gE deleted site.

S–FHV 040 was derived from S–FHV 019. This was accomplished utilizing the homology vector 987-57.A1 and the virus S–FHV 019 in the HOMOLOGOUS RECOMBINATION PROCEDURE FOR GENERATING RECOMBINANT FHV. The transfection stock was screened by the SCREEN FOR RECOMBINANT FHV EXPRESSING b-glucuronidase (X-GLUC ASSAY). The final result of multiple rounds of purification for green/blue plaques was the recombinant virus S–FHV 040.

S–FHV 040 was assayed for expression of FeLV gag, and the marker genes β-glucuronidase and β-galactosidase by BLACK PLAQUE Assay. 100% of the plaques generated in CRFK cells were determined to be expressing β-glucuronidase and β-galactosidase. The expression of the FeLV gag was also confirmed by BLACK PLAQUE Assay using the goat polyclonal antibody to FeLV gp27 (BioDesigns; ME). This virus appears to be stable after five passages.

The expression of Feline CD80, CD86, and FeLV gag was confirmed in WESTERN BLOT analysis. The goat polyclonal anti-human CD80 and CD86 antibodies (R&D Systems; MN) were used for feline CD80 and CD86. Multiple bands ranging from 30 kDa to 60 kDa specific for feline CD80 were detected, and bands ranging from 40 kDa to 70 kDa specific for feline CD86 were also detected. The expression of FeLV was confirmed by using a goat polyclonal antibody to FeLV gp27 (BioDesigns, ME).

S–FHV 042:

S–FHV 042 is a recombinant feline herpes virus expressing five foreign genes. A homology vector designated 957-87.A1 was constructed in the following way: The feline CD80 and CD86 genes were expressed in a bicistronic DNA cassette under the control of the cytomegalovirus immediate early promoter (CMV IE), driving the transcription of CD80 and CD86, and included an EMCV IRES element between the two open reading frames. The β-glucuronidase gene is under the control of the infectious laryngotracheitis virus gI promoter. CD80, CD86, and the β-glucuronidase genes were inserted into the FHV unique long region in a unique EcoRI site derived from a partial Sal I H fragment of FHV, between the gL and adjacent transcriptional activator genes. The parent virus was β-FHV 018 which contains the CMV IE promoted FeLV envelope, and *E. coli* β-galactosidase gene under the pseudorabies gX promoter; both genes are located in the FHV unique short (US) gE deleted site.

S–FHV 042 was derived from S–FHV 018. This was accomplished utilizing the homology vector 987-57.A1 and the virus S–FHV 018 in the HOMOLOGOUS RECOMBINATION PROCEDURE FOR GENERATING RECOMBINANT FHV. The transfection stock was screened by the SCREEN FOR RECOMBINANT FHV EXPRESSING b-glucuronidase (X-GLUC ASSAY). The final result of multiple round of purification for green/blue plaques was the recombinant virus S–FHV 042. S–FHV 042 was assayed for expression of FeLV env, and the marker genes β-glucuronidase and β-galactosidase by BLACK PLAQUE Assay. 100% of the plaques generated in CRFK cells were determined to be expressing β-glucuronidase and β-galactosidase. The expression of FeLV env was confirmed by BLACK PLAQUE Assay using the mouse monoclonal antibody to FeLV gp70 (BioDesigns; ME). This virus was stable after five passages.

The expression of feline CD80, CD86, and FeLV env was confirmed in WESTERN BLOT analysis. The goat polyclonal anti-human CD80 and CD86 antibodies (R&D Systems; MN) were used for feline CD80 and CD86. Multiple bands ranging from 30 kDa to 60 kDa specific for feline CD80 were detected, and so were bands ranging from 40 kDa to 70 kDa specific for feline CD86. A 10 kDa FeLV env band was detected using the mouse monoclonal antibody to gp70 (BioDesigns; ME).

S–FHV 044:

S–FHV 044 is a recombinant feline herpes virus expressing five foreign genes. A homology vector designated 957-87.A1 was constructed in the following way: The feline CD80 and CD86 genes were expressed in a bicistronic DNA cassette under the control of the cytomegalovirus immediate early promoter (CMV IE), driving the transcription of CD80 and CD86, and included an EMCV IRES element between the two open reading frames. The β-glucuronidase gene is under the control of the infectious laryngotracheitis virus gI promoter. CD80, CD86, and the β-glucuronidase genes were inserted into the FHV unique long region in a unique EcoRI site derived from a partial Sal I H fragment of FHV, between the gL and adjacent transcriptional activator genes. The parent virus used was S–FHV 016 which contains the CMV IE promoted FIV gag/protease (with a nine amino acid deletion in the five prime end of the protease gene), and *E. coli β-galactosidase gene which is under the pseudorabies gX promoter; both genes are located in the FHV unique short (US) gE deleted site.*

S–FHV 044 was derived from S–FHV 016. This was accomplished utilizing the homology vector 987-57.A1 and the virus S–FHV 016 in the HOMOLOGOUS RECOMBINATION PROCEDURE FOR GENERATING RECOMBINANT FHV. The transfection stock was screened by the SCREEN FOR RECOMBINANT FHV EXPRESSING β-glucuronidase (X-GLUC ASSAY). The final result of multiple round of purification for green/blue plaques was the recombinant virus S–FHV 044. S–FHV 044 was assayed for expression of FIV gag, and the marker genes β-glucuronidase and β-galactosidase by BLACK PLAQUE Assay. 100% of the plaques generated in CRFK cells were determined to be expressing both marker genes utilizing mouse monoclonal antibodies (BioDesign, ME). The expression of FIV gag was also confirmed using BLACK PLAQUE ASSAY using the mouse monoclonal antibody for FIV gag (Custom Monoclonals, CA). This virus was stable after five passages.

The expression of feline CD80, CD86, and FeLV gag was confirmed in WESTERN BLOT analysis. The goat polyclonal anti-human CD80 and CD86 antibodies (R&D Systems; MN) were used for feline CD80 and CD86. Multiple bands ranging from 30 kDa to 60 kDa specific for feline CD80 were detected, as were bands ranging from 40 kDa to 70 kDa specific for feline CD86. Two distinct bands were detected 50 kDa and 27 kDa specific for FIV gag using the monoclonal FIV gag antibody

TABLE 2

SPV Recombinant Viruses containing the genes encoding CD80 and/or CD86 or CD28.

| Virus No. | Description of Foreign Gene Insertions | Expression Analysis by Western Blot or Black Plaque Assays. CD 80 | CD 86 | GAG | ENV | β-GAL | β-GLU |
|---|---|---|---|---|---|---|---|
| SPV 228 | EP2-FIVgag/EP1-FIVenv/I5L-lacZ Homology vector = 926-45.A17 Parent virus = SPV 001 | | | + | + | + | |
| SPV 261 | EP2 -FIVgag/EP1-FIVenv/I5L-lacZ// L2E2 -CD80/E2-UIDA Homology vector = 931-21.A1 Parent virus = SPV 228 | + | | + | + | + | + |
| SPV 275 | L2E2 -FIVgag/O1L-lacZ// L1-CD86/IRES-CD80/E2-UIDA Homology vector = 992-23.6 and 992-23.2 Parent virus = SPV 046 | + | + | + | | + | + |
| SPV 258 | L2E2-FeLVGag/L2E2-FeLVΔTMenv/L1-lacZ Homology vector = 954-44.1 Parent = SPV 001 | | | + | + | + | |
| SPV 281 | EP2-FIVgag/EP1-FIVenv/I5L-lacZ//L1-CD86/IRES-CD80/E2-UIDA Homology vector = 992-23.6 Parent virus = SPV 228 | + | + | + | + | + | + |
| SPV 246 | E2-FeLVgag/E1-FeLVenv/I5L-lacZ//L2E2-CD80/E2-uida Homology vector = 931-21.A1 Parent virus = SPV 224 | + | | + | + | + | + |
| SPV 276 | L2E2-FeLVgag/L1-lacZ// L1-CD86/IRES-CD80/E2-UIDA Homology vector = 992-23.6 Parent virus = SPV 089 | + | + | + | | + | + |
| SPV 279 | E1-FeLVenv/L1-lacZ// L1-CD86/IRES-CD80/E2-UIDA Homology vector = 992-23.6 Parent virus = SPV 195 | + | + | | + | + | + |
| SPV 280 | L2E2-FeLVGag/L2E2-FeLVΔTMenv/L1-lacZ// L1-CD86/IRES-CD80/E2-UIDA Homology vector = 992-23.6 Parent virus = SPV 258 | + | + | + | + | + | + |
| SPV 285 | E2-FeLVgag/E1-FeLVenv/I5L-lacZ//L1-CD80/IRES/CD86/gI-UIDA Homology vector = 992-23.6 Parent virus = SPV 224 | + | + | + | + | + | + |
| SPV 270 | LE-CD80ΔTM/HIS/E2-uidA Homology vector = 961-27.4 Parent virus = SPV 001 | + | | | | | + |
| SPV 272 | LE-CD86ΔTM/HIS/E2-uidA(19-2) Homology vector = 969-20.9 Parent virus = SPV 001 | | + | | | | + |
| SPV 273 | LE-CD28ΔTM/HIS/E2-uidA Homology vector = 930-91.2 Parent virus = SPV 001 | | | | | | + |
| SPV 274 | LE-CD86(FL)/EP2-UIDA Homology vector = 977-40.1 Parent virus = SPV 001. | | + | | | | + |
| SPV 282 | LP1-CD86/IRES-CD80/E2-UIDA Homology vector = 992-23.6 Parent virus = SPV 001 | + | + | + | + | | + |

TABLE 3

RPV Recombinant Viruses containing the genes encoding CD80 and/or CD86 and CD-28.

| Virus No. | Description of Foreign Gene Insertions | Expression Analysis by Western Blot or Black Plaque Assays. CD 80 | CD 86 | GAG | ENV | β-GAL | β-GLU |
|---|---|---|---|---|---|---|---|
| RPV 046 | L2E2-FTVgag/E2-UIDA// LP1-CD86/IRES-CD80/I5L-LacZ Homology vector = 1015-18.8A Parent virus = RPV 036 | + | + | + | | + | + |
| RPV 047 | E1-FIVenv/E2-UIDA// LP1-CD86/IRES-CD80/I5L-LacZ Homology vector = 1015-18.8A | + | + | | + | + | + |

TABLE 3-continued

RPV Recombinant Viruses containing the genes encoding CD80 and/or CD86 and CD-28.

| Virus No. | Description of Foreign Gene Insertions | Expression Analysis by Western Blot or Black Plaque Assays. CD 80 | CD 86 | GAG | ENV | β-GAL | β-GLU |
|---|---|---|---|---|---|---|---|
| | Parent virus = RPV 037/044 | | | | | | |
| RPV 048 | L2E2-FeLV Gag/E2-UIDA LP1-B7-/IRES-CD80/I5L-lacZ Homology vector = 1015-18.8A Parent virus = RPV 038 | + | + | + | | + | + |
| RPV 052 | H3 "U" Xbal site/LP1-uidA/EP1-FeLVenv/S-RPV-030 EP2-FeLVgag H3 "N" I5L-lacZ/L1-FeCD86/IRES/FeCD80 Homology vector = 1015-18.8A Parent virus = RPV-030 | + | + | + | + | + | + |
| RPV 053 | H3 "U" Xba I site/EP2-FIVgag/EP1-FIVenv/S-RPV-034 LP1-uidA//H3 "N" I5L-lacZ/L1-FeCD86/IRES/FeCD80 Homology vector = 1015-18.8A Parent virus = RPV 034 | + | + | + | + | + | + |
| RPV 022 | L2E2-CD80/L1-lacZ Homology vector = 931-32.A5 Parent virus = RPV-000 | + | | | | + | |
| RPV 045 | LP1-CD86/IRES-CD80/I5L-LacZ Homology vector = 1015-18.8A Parent virus = RPV 000 | + | + | | | + | |

TABLE 4

FHV Recombinant Viruses containing the genes encoding CD80 and/or CD86 and CD28.

| Virus No. | Description of Foreign Gene Insertions | Expression Analysis by Western Blot or Black Plaque Assay. CD 80 | CD 86 | GAG | ENV | β-GAL | β-GLU |
|---|---|---|---|---|---|---|---|
| FHV 044 | IE-FIVgag(-9a.a.)/gX-lacZ//IE-CD86/IRES-CD80/gI-UIDA Homology vector = 987-57.A1 Parent virus = FHV 016 | + | + | + | | + | + |
| FHV 047 | IE-FIVgag(-9a.a.)/gX-lacZ//IE-CD86-TkpA/gI-UIDA Homology vector = 994-68.4 Parent virus = FHV 016 | | + | + | | + | + |
| FHV 048 | IE-FIVenv/gX-LacZ ($\Delta$gE)//IE-CD86-TkpA/gI-UIDA Homology vector = 994-68.4 Parent virus = FHV 017 | | + | | + | + | + |
| FHV 042 | IE-FeLVenv/gX-LacZ ($\Delta$gE)//IE-CD86/IRES-CD80/gI-UIDA (SalH IG) Homology vector = 987-57.A1 Parent virus = FHV 018 | + | + | | + | + | + |
| FHV 040 | IE-FeLVgag/gX-LacZ ($\Delta$gE)//IE-CD86/IRES-CD80/gI-UIDA (SalH IG) Homology vector = 987-57.A1 Parent virus = FHV 019 | + | + | + | | + | + |
| FHV 049 | IE-FeLVenv/gX-LacZ ($\Delta$gE) IE-FeCD86-TkpA/gI-uidA (SalH IG) Homology vector = 994-68.4 Parent virus = FHV 018 | | + | | + | + | + |
| FHV 050 | IE-FeLVgag/gX-LacZ ($\Delta$gE) IE-FeCD86-TkpA/gI-uidA (SalH IG) Homology vector = 994-68.4 Parent virus = FHV 019 | | + | + | | + | + |
| FHV 030 | gE-CD80/gE-lacZ ($\Delta$gE) Homology vector = 926-76.D7 Parent virus = FHV 020 | + | | | | + | |

ADDITIONAL EXAMPLES INVOLVING CO-VECTORING FELINE CD80 and CD86, etc. WITH THE PARTIAL or FULL-LENGTH GENOMES OF FIV or FELV.

Note: Recombinant viral vectors containing CD80, CD86, CTLA4 or CD28 in a recombinant virus with the partial or full genome complement of FIV and/or FIV and with or without feline IL-12 p35 and p40. These recombinant viruses have potential as vaccines against FIV and FeLV disease in felids.

1. Expression of feline CD80, CD86, CD28, and CTLA4, alone or in any combination, in a recombinant swinepox virus containing the full or partial genome of FIV.

2. Expression of feline CD80, CD86, CD28, and CTLA4, alone or in any combination, in a recombinant feline herpesvirus containing the full or partial genome of FIV.
3. Expression of feline CD80, CD86, CD28, and CTLA4, alone or in any combination, in a recombinant raccoonpox virus containing the full or partial genome of FIV.
4. Expression of feline CD80, CD86, CD28, and CTLA4, alone or in any combination, in a recombinant swinepox virus containing full or partial genome of FeLV.
5. Expression of feline CD80, CD86, CD28, and CTLA4, alone or in any combination, in a recombinant feline herpesvirus containing the full or partial genome of FeLV.
6. Expression of feline CD80, CD86, CD28, and CTLA4, alone or in any combination, in a recombinant raccoonpox virus containing the full or partial genome of FeLV.
7. Expression of feline CD80, CD86, CD28, and CTLA4, alone or in any combination, in a recombinant swinepox virus containing full or partial genome of FIV and the genes for feline IL12, GM-CSF, p35 and p40.
8. Expression of feline CD80, CD86, CD28, and CTLA4, alone or in any combination, in a recombinant feline herpesvirus containing the full or partial genome of FIV and the genes for feline IL12, GM-CSF, p35 and p40.
9. Expression of feline CD80, CD86, CD28, and CTLA4, alone or in any combination, in a recombinant raccoonpox virus containing the full or partial genome of FIV and the genes for feline IL12, GM-CSF, p35 and p40.
10. Expression of feline CD80, CD86, CD28, and CTLA4, alone or in any combination, in a recombinant swinepox virus containing full or partial genome of FeLV and the genes for feline IL12, GM-CSF, p35 and p40.
11. Expression of feline CD80, CD86, CD28, and CTLA4, alone or in any combination, in a recombinant feline herpesvirus containing the full or partial genome of FeLV and the genes for feline IL12, GM-CFS, p35 and p40.
12. Expression of feline CD80, CD86, CD28, and CTLA4, alone or in any combination, in a recombinant raccoonpox virus containing the full or partial genome of FeLV and the genes for feline IL12, GM-CSF, p35 and p40.

TABLE 5

Recombinant Viruses containing the FIV genome (ΔLTRs) and genes encoding Feline CD80 and/or CD86

| Virus No. | Description of Foreign Gene Insertions | Expression Analysis by Western Blot or Black Plaque | | | | | |
|---|---|---|---|---|---|---|---|
| | | CD 80 | CD 86 | GAG | ENV | β-GAL | β-GLU |
| FHV 054 | CMV-FIVgenome/gX-lacZ//gE-CD80 Homology Vector = 1016-75.B1 Parent = FHV 030 | + | | + | + | + | |
| FHV 055 | CMV-FIVgenome/gX-lacZ//gE-CD86/gX-UIDA Homology Vector = 1016-75.B1 Parent = FHV 041 | | + | + | + | + | + |
| RPV 055 | CMV-FIVgenome/LP1-UIDA//LP1-CD86/IRES-CD80/I5L-lacZ Homology Vector = 1005-95.1 Parent = RPV 045 | + | + | + | + | + | + |
| SPV 288 | CMV-FIV genome/I5L- | + | + | + | + | + | + |

TABLE 5-continued

Recombinant Viruses containing the FIV genome (ΔLTRs) and genes encoding Feline CD80 and/or CD86

| Virus No. | Description of Foreign Gene Insertions | Expression Analysis by Western Blot or Black Plaque | | | | | |
|---|---|---|---|---|---|---|---|
| | | CD 80 | CD 86 | GAG | ENV | β-GAL | β-GLU |
| | lacZ//LP1-CD86/IRES-CD80/EP2-UIDA Homology Vector = 1007-70.A2 Parent = RPV 045 | | | | | | |

EXAMPLES

HOMOLOGY VECTOR 1007-70.A2 (SPV N/CMV-FIVgenomeΔLTR/I5L-lacZ). The homology vector 1007-70.A2 was used to insert foreign DNA into the HindIII N insertion site of SPV. It incorporates an *E. coli* β-galactosidase marker gene and the full-length FIV genome (8.5 kb) without the flanking long terminal repeat (LTR) elements. This cassette is flanked by SPV DNA homologous to a non-essential site within the SPV H.III N fragment. When this homology vector was used according to the HOMOLOGOUS RECOMBINATION PROCEDURE FOR GENERATING RECOMBINANT SPV, a virus containing DNA coding for the foreign genes results. Note that β-galactosidase marker gene is under the control of a constitutive pox promoter, I5L, and the FIV genome (Δ LTRs) is under the control of the cytomegalovirus immediate early (CMV IE). The homology vector was constructed utilizing standard recombinant DNA techniques (Sambrook, et al.). The FIV genome (Δ LTRs) was synthesized by CLONING WITH THE POLYMERASE CHAIN REACTION. The template for the PCR reaction was proviral DNA from a plasmid containing the full-length FIV PPR virus. The upstream primer (5' ACGCGTCGACCAGCTAACAAGG TAGGAGAGACTCT-3'; 11/23/98BW.3) synthesizes from the 5' end of the FIV genome upstream of the Gag coding region and introduces a unique Sal I site. The downstream primer (5'-TCGAGTCGACTTGTGACAGTTCT TAGTCCATAAGC-3'; 11/11/98BW.1) synthesizes from the 3' end of the FIV genome downstream of the 2nd Rev exon and introduces a unique Sal I site. The final homology vector, 1007.70.A2, was used to create recombinant viruses containing the FIV genome (without LTRs) and feline CD80 and CD86 or containing the FIVgenome (minus LTR) and feline CD80 and CD86 and feline IL-12 genes, p35 and p40 according to the HOMOLOGOUS RECOMBINATION PROCEDURE FOR GENERATING RECOMBINANT SPV, RPV and FHV.

HOMOLOGY VECTOR 1005-95.1 (RPV U/CMV-FIV genome (ΔLTR)/I5L-LacZ).

The plasmid 1005-95.1 was constructed for the purpose of inserting foreign DNA into RPV. It incorporates the FIV genome-ΔLTR and the *E. coli* β-glucuronidase gene flanked by RPV DNA. Upstream of the foreign gene is an approximately 906 base pair fragment of RPV DNA. Downstream of the foreign genes is an approximately 895 base pair fragment of RPV DNA. When the plasmid is used according to the HOMOLOGOUS RECOMBINATION PROCEDURE FOR GENERATING RECOMBINANT RPV, a virus containing DNA coding for the foreign genes will result. Note that the FIV genome-ΔLTR is under the control of the cytomegalovirus immediate early promoter and the *E. coli* β-glucuronidase gene is under the synthetic early pox promoter, EP2. The homology vector was constructed utilizing standard recombinant DNA techniques (Sambrook, et al.), by joining restriction fragments from the following sources with the synthetic DNA sequences. The plasmid vector was derived from an approximately 2999 base pair HindIII restriction fragment of pSP64 (Promega). Fragment 1 is an approximately 906 base pair HindIII to XbaI restriction sub-fragment of the RPV HindIII restriction fragment U (Knight, et al.). Fragment 2 is an approximately 8.5 kb SalI fragment of the FIV genome without the LTR elements and was synthesized by CLONING WITH THE POLYMERASE CHAIN REACTION. The template for the PCR reaction was proviral DNA from a plasmid containing the full-length FIV PPR virus. The upstream primer (5' ACG CGTCGACCAGCTAACAAGGTAGGAGAGACTCT-3'; 11/23/98BW.3) synthesizes from the 5' end of the FIV genome upstream of the Gag coding region and intoduces a unique Sal I site. The downstream primer (5'-TCGAGTCGACTTGTGACAGTTCTTAGTCCATAAGC-3'; 11/11/98BW.1) synthesizes from the 3' end of the FIV genome downstream of the 2nd Rev exon and introduces a unique Sal I site. Fragment 3 is an approximately 2.0 kb fragment containing the *E. coli* β-glucuronidase gene. Fragment 4 is an approximately 895 base pair XbaI to HindIII sub-fragment of the RPV HindIII fragment U. The final homology vector, 1005.95.1 was used to create recombinant viruses containing the FIV genome (Δ LTRs) and feline CD80 and CD86 genes or to create recombinant viruses containing the FIVgenome (Δ LTR) and feline CD80 and CD86 and feline IL-12 genes, p35 and p40 according to the HOMOLOGOUS RECOMBINATION PROCEDURE FOR GENERATING RECOMBINANT SPV, RPV and FHV.

HOMOLOGY VECTOR 1016-74.A6 (FHVΔgE/CMV-FIVgenome-ΔLTR/gX-lacZ). The homology vector 1016-74.A6 was constructed for the purpose of deleting a portion of the gE coding region from the feline herpesvirus and inserting a foreign DNA. It incorporates the FIV genome (minus LTRs) and the *E. coli* β-galactosidase gene flanked by FHV DNA. The FIV genome-ΔLTR is under the cytomegalovirus IE promoter and the β-galactosidase gene is under the control of the pseudorabies virus gX promoter. It was constructed from the indicated DNA sources utilizing standard recombinant DNA techniques (Sambrook, et al.). The plasmid vector is derived from an approximately 2958 base pair Asp718I to Asp718I restriction endonuclease fragment of a pSP18/19. Fragment 1 is an approximately 1415 base pair Asp718I to SmaI sub-fragment of the FHV SalI B fragment. Fragment 2 is an approximately 8.5 kb SalI fragment of the FIV genome without the LTR elements and was synthesized by CLONING WITH THE POLYMERASE CHAIN REACTION. The template for the PCR reaction was proviral DNA from a plasmid containing the full-length FIV PPR virus. The upstream primer (5' ACGCGTCGACCAGCTAACAAGGTAGGAGAGACTCT-3'; 11/23/98BW.3) synthesizes from the 5' end of the FIV genome upstream of the Gag coding region and intoduces a unique Sal I site. The downstream primer (5'-TCGAGTCGACTTGTGACAGTTCTTAGTCCATAAGC-3'; 11/11/98BW.1) synthesizes from the 3' end of the FIV genome downstream of the 2nd Rev exon and introduces a unique Sal I site. Fragment 3 is an approximately 3.5 kb β-galactosidase gene fragment. Fragment 4 is an approximately 2205 base pair SalI to Asp718I sub-fragment of the FHV EcoRI E fragment. The final homology vector, 1016-74.A6 was used to create recombinant viruses containing the FIV genome (Δ LTRs) and feline CD80 and CD86 genes or to create recombinant viruses containing the FIVgenome (Δ LTR) and feline CD80 and CD86 and feline IL-12 genes, p35 and p40 according to the HOMOLOGOUS RECOMBINATION PROCEDURE FOR GENERATING RECOMBINANT SPV, RPV and FHV.

SPV 288

SPV 288 is a recombinant swinepox virus expressing the entire complement of the ORFs contained in the FIV genome and 4 additional foreign genes. SPV 288 was derived from SPV 282. SPV 282 contains the feline CD86 gene and the CD80 gene expressed in a bicistronic DNA cassette under the control of the synthetic late pox promoter, LP1, driving the transcription of CD80 and CD86 and including an EMCV IRES element between the two open reading frames; and the *E. coli* β-glucuronidase gene under the control of the synthetic early promoter, EP2, in the SPV H.III K genomic fragment. The homology vector 992-23.6 was used to construct SPV 282 by utilizing the HOMOLOGOUS RECOMBINATION PROCEDURE FOR GENERATING RECOMBINANT RPV, SPV, OR FHV. The CD80 and CD86 and *E. coli* β-glucuronidase genes are inserted into a distinct and non-essential SPV partial Hind III K fragment. The CMV-FIV genome and β-galactosidase genes are inserted into the distinct and non-essential SPV partial Hind III N fragment.

SPV 288 was derived from SPV 282. This was accomplished utilizing the homology vector 1007-70.A2 (See above) and virus SPV 282 in the HOMOLOGOUS RECOMBINATION PROCEDURE FOR GENERATING RECOMBINANT RPV, SPV, OR FHV. The transfection stock was screened by the SCREEN FOR RECOMBINANT SPV EXPRESSING β-galactosidase (BLUOGAL and CPRG ASSAYS) or β-glucuronidase (X-GLUC ASSAY). The final result of multiple rounds of blue/green plaque purification was the recombinant virus SPV 288.

SPV 288 was assayed for expression of FeLVgag, FeLV envelope from the FIV genome and the marker genes, β-galactosidase and β-glucuronidase by BLACK PLAQUE Analysis. 100% of plaques generated from ESK-4 cells infected with purified SPV 280 were determined to be expressing FeLVgag and FeLV envelope, using a goat polyclonal antibody for FeLVgag (Biodesign, ME) and a mouse monoclonal antibody for FeLV envelope, gp70 (Biodesign, ME).

The expression of feline CD80 and CD86 was confirmed in WESTERN BLOT analysis using goat polyclonal anti-human CD80 and CD86 antibodies (R&D Systems, MN), respectively. Multiple bands ranging in size from 30 kda to 60 kda specific for feline CD80 were detected, and multiple bands ranging from 40 kda to 70 kda specific for feline CD86 were detected. These bands represent alternate and multiple glycosylation patterns of CD80 and CD86 expressed in the context of SPV in ESK-4 cells. The expression of the proteins encoded in the FIV genome were confirmed in WESTERN BLOT analysis using cat sera from cats infected with FIV.

FHV 054

FHV 054 is a recombinant feline herpes virus expressing the entire complement of the ORFs contained in the FIV genome and 2 additional foreign genes. A homology vector designated 1016-75.B1 was constructed for the purpose of inserting the FIV genome(ALTR) and β-galactosidase into the FHV Unique Long partial Sal H fragment.

The insertion is between the gL gene and the adjacent transcriptional activator gene.

The FIV genome is under the control of the CMV IE promoter; and the *E. coli* β-galactosidase gene is under the control of the pseudorabies gX promoter element.

FHV 054 was derived from FHV 030, which contains the feline CD80 gene in the FHV gE deleted site. This was accomplished by utilizing the homology vector 1016-75.B1 and virus FHV 030 in the HOMOLOGOUS RECOMBINATION PROCEDURE FOR GENERATING RECOMBINANT RPV, SPV, OR FHV. The transfection stocks were screened by the SCREEN FOR RECOMBINANT FHV EXPRESSING β-galactosidase (BLUOGAL and CPRG ASSAYS) or β-glucuronidase (X-GLUC ASSAY) METHODS. The final result of multiple rounds of blue/green plaque purification was the recombinant virus FHV 054.

FHV 054 was assayed for expression of the β-galactosidase by BLACK PLAQUE Analysis. 100% of plaques from CRFK cells infected with plaque purified FHV 054 were determined to be expressing β-galactosidase, utilizing a mouse monoclonal antibody (Biodesign, ME). This virus was determined to be stable after at least 5 passages.

The expression of feline CD80, FIV gag and FIV envelope was confirmed in WESTERN BLOT analysis utilizing polyclonal anti-human CD80 antibodies (R&D Systems, MN), mouse monoclonal anti-FIV gag antibodies (Custom Monoclonals, CA) and mouse monoclonal anti-FIV envelope antibody (Biodesign). The expression of the full complement of FIV genes encoded in the genome were confirmed in WESTERN BLOT analysis utilizing a convalescent cat sera from an FIV infected cat.

FHV 055

FHV 055 is a recombinant feline herpes virus expressing the entire complement of the ORFs contained in the FIV genome and 3 additional foreign genes . A homology vector designated 1016-75.B1 was constructed for the purpose of inserting the FIV genome (ΔLTR) and β-galactosidase into the FHV Unique Long partial Sal H fragment.

The insertion is between the FHV gL gene and the adjacent transcriptional activator gene.

The FIV genome is under the control of the CMV IE promoter; and the *E. coli* β-galactosidase gene is under the control of the pseudorabies gX promoter element.

FHV 055 was derived from FHV 041, which contains the feline CD86 gene and the β-glucuronidase gene in the FHV gE deleted site. Feline CD86 is under the control of the FHV gE promoter and the β-glucuronidase gene is under the control of the pseudorabies virus gX promoter. This was accomplished by utilizing the homology vector 1016-75.B1 and virus FHV 041 in the HOMOLOGOUS RECOMBINATION PROCEDURE FOR GENERATING RECOMBINANT RPV, SPV, OR FHV. The transfection stocks were screened by the SCREEN FOR RECOMBINANT FHV EXPRESSING β-galactosidase (BLUOGAL and CPRG ASSAYS) or β-glucuronidase (X-GLUC ASSAY) METHODS. The final result of multiple rounds of blue/green plaque purification was the recombinant virus FHV 055.

FHV 055 was assayed for expression of the β-galactosidase and β-glucuronidase by BLACK PLAQUE Analysis. 100% of plaques from CRFK cells infected with plaque purified FHV 055 were determined to be expressing β-galactosidase and β-glucuronidase, utilizing a mouse monoclonal antibody (Biodesign, ME) and rabbit polyclonal (Molecular Probes, OR), respectively. This virus was determined to be stable after at 5 passages.

The expression of feline CD86, FIV gag and FIV envelope was confirmed in WESTERN BLOT analysis utilizing polyclonal anti-human CD86 antibodies (R&D Systems, MN), mouse monoclonal anti-FIV gag antibodies (Custom Monoclonals, CA) and mouse monoclonal anti-FIV envelope antibody (Biodesign). The expression of the full complement of FIV genes encoded in the genome were confirmed in WESTERN BLOT analysis utilizing a convalescent cat sera from an FIV infected cat.

RPV 055

RPV 055 is a recombinant raccoonpox virus expressing the entire complement of the ORFs contained in the FIV genome and 4 additional foreign genes. RPV 055 was derived from RPV 045, which contains the feline CD86 gene and the CD80 gene expressed in a bicistronic DNA cassette under the control of the synthetic late pox promoter, LP1, driving the transcription of CD80 and CD86 and including an EMCV IRES element between the two open reading frames; and the *E. coli* β-glucuronidase gene under the control of the synthetic early promoter, EP2, in the RPV H.III N genomic partial fragment. The homology vector 1005-95.1 was used to construct RPV 055 by utilizing the HOMOLOGOUS RECOMBINATION PROCEDURE FOR GENERATING RECOMBINANT RPV, SPV, OR FHV. The CD80 and CD86 and *E. coli* β-galactosidase genes are inserted into a distinct and non-essential RPV partial Hind III N fragment. The CMV-FIV genome and β-glucuronidase genes are inserted into the distinct and non-essential RPV partial Hind III U fragment.

RPV 055 was derived from RPV 045. This was accomplished utilizing the homology vector 1005-95.1 and virus RPV 045 in the HOMOLOGOUS RECOMBINATION PROCEDURE FOR GENERATING RECOMBINANT RPV, SPV, OR FHV. The transfection stock was screened by the SCREEN FOR RECOMBINANT SPV EXPRESSING β-galactosidase (BLUOGAL and CPRG ASSAYS) or β-glucuronidase (X-GLUC ASSAY). The final result of multiple rounds of blue/green plaque purification was the recombinant virus RPV 055.

RPV 055 was assayed for expression of FeLVgag, FeLV envelope from the FIV genome and the marker genes, β-galactosidase and β-glucuronidase by BLACK PLAQUE Analysis. 100% of plaques generated from VERO infected cells with purified RPV 055 were determined to be expressing FeLVgag and FeLV envelope, using a goat polyclonal antibody for FeLVgag (Biodesign, ME) and a mouse monoclonal antibody for FeLV envelope, gp70(Biodesign, ME).

The expression of feline CD80 and CD86 was confirmed in WESTERN BLOT analysis using goat polyclonal anti-human CD80 and CD86 antibodies (R&D Systems, MN), respectively. Multiple bands ranging in size from 30 kda to 60 kda specific for feline CD80 were detected, and multiple bands ranging from 40 kda to 70 kda specific for feline CD86 were detected. These bands represent alternate and multiple glycosylation patterns of CD80 and CD86 expressed in the context of RPV in VERO cells. The expression of the proteins encoded in the FIV genome were confirmed in WESTERN BLOT analysis using cat sera from cats infected with FIV.

What is claimed is:

1. A recombinant virus which comprises at least one foreign nucleic acid inserted within a non-essential region of the viral genome of a virus, wherein said foreign nucleic acid (a) encodes a feline CD86 protein having the amino acid sequence of SEQ ID No. 6 and (b) is expressed when the recombinant virus is introduced into an appropriate host.

2. The recombinant virus of claim 1 which comprises at least two foreign nucleic acids, each inserted within a non-essential region of the viral genome.

3. The recombinant virus of claim 1 which comprises at least three foreign nucleic acids, wherein each is inserted within a non-essential region of the viral genome.

4. The recombinant virus of claim 2 which comprises four foreign nucleic acids, wherein each is inserted within a non-essential region of the viral genome.

5. The recombinant virus of claim 1, wherein the virus is raccoonpox virus, a swinepox virus, or a feline herpesvirus.

6. The recombinant virus of claim 1 comprising more than one foreign nucleic acid, wherein each foreign nucleic acids is inserted into the same non-essential region of the viral genome.

7. The recombinant virus of claim 1 comprising more than one foreign nucleic acid, wherein each foreign nucleic acids is not inserted into the same non-essential region of the viral genome.

8. The recombinant virus of claim 1 further comprising a foreign nucleic acid encoding an immunogen derived from a pathogen.

9. The recombinant virus of claim 8, wherein the pathogen is a feline pathogen, a rabies virus, *Chlamydia, Toxoplasma gondii, Dirofilaria immitis*, a flea, or a bacterial pathogen.

10. The recombinant virus of claim 9, wherein the feline pathogen is feline immunodeficiency virus (FIV), feline leukemia virus (FeLV), feline infectious peritonitis virus (FIP), feline panleukopenia virus, feline calicivirus, feline reovirus type 3, feline rotavirus, feline coronavirus, feline syncytial virus, feline sarcoma virus, feline herpesvirus, feline Borna disease virus, or a feline parasite.

11. The recombinant virus of claim 1, wherein at least one foreign nucleic acid comprises a promoter for expressing the foreign nucleic acid.

12. The recombinant virus of claim 1, wherein the expression of a least one foreign nucleic acids is under the control of a promoter endogenous to the virus.

13. The recombinant virus of claim 1 further comprising a foreign nucleic acid encoding a detectable marker.

14. The recombinant virus of claim 13, wherein the detectable marker is E.coli beta galactosidase.

15. The recombinant virus of claim 10, wherein the immunogen from a feline pathogen is FIV gag protease, a FIV envelope protein, a FeLV gag protease, or a FeLV envelope protein.

16. The recombinant virus of claim 1, wherein the virus is a feline herpesvirus and the nonessential region is the glycoprotein E gene of feline herpesvirus.

17. The recombinant feline herpesvirus of claim 12 designated S-FHV-031 (ATCC Accession No. VR-2604).

18. The recombinant virus of claim 1, wherein the virus is swinepox virus and the nonessential region is the larger Hind III to Bgl II subfragment of the Hind III M fragment of swinepox virus.

19. The recombinant swinepox of claim 14, wherein the recombinant virus is a swinepox virus designated S-SPV-246 (ATCC Accession No. VR-2603).

20. The recombinant virus of claim 1, wherein the portion of the CD28, CD80, or CD86 protein is the soluble portion of the protein.

21. The recombinant virus of claim 1, where the foreign nucleic acid encodes the feline CTLA-4 protein.

22. A vaccine comprising the recombinant virus of claim 1, wherein the recombinant virus is in an effective immunizing amount, and a suitable carrier.

23. The vaccine of claim 22, wherein the effective immunizing amount of the recombinant virus is an amount between about $1\times10^5$ pfu/ml and about $1\times10^8$ pfu/ml.

24. The vaccine of claim 22 which further comprises an admixture of the recombinant virus with an effective immunizing amount of a second immunogen.

25. A method for enhancing an immune response in a feline which comprises administering to the feline an effective immunizing amount of the redombinant virus of claim 1.

26. A method for immunizing a feline which comprises administering to the feline an effective immunizing amount of the recominant virus of claim 1.

27. A method for suppressing an immune response in a feline which comprises administering to the feline any effective suppressing amount of the recombinant virus of claim 20.

28. The method of claim 25, wherein the administering comprises intravenous, subcutaneous, intramuscular, transmuscular, topical, oral, or intraperitoneal administration.

29. The method of claim 27, wherein the feline is the recipient of a transplanted organ or tissue or is suffering from an immune response.

30. A method for reducing or abrogating a tumor in a feline which comprises administering to the tumor in the feline a recombinant virus of claim 1, wherein the nucleis acid encodes a feline CD80 protein, a feline CD86 protein or a combination thereof in an amount effective reduce or abrogate the tumor.

31. The method of claim 30, wherein the recombinant virus further comprises, and is capable of expressing, a feline tumor associated antigen and the administration is effected systemically.

32. The recombinant virus of claim 1, further comprising a nucleic acid encoding the feline immunodeficiency virus genome or a portion thereof.

33. The recombinant virus of claim 1, further comprising a nucleic acid encoding feline leukemia virus genome or a portion thereof.

34. The resombinant virus of claim 32, further comprising a nucleic acid encoding feline GM-CSF or feline IL-12 p35 and p40.

35. The resombinant virus of claim 33, further comprising a nucleic acid encoding feline GM-CSF or feline IL-12 p35 and p40.

36. A vaccine which comprises an effective immunizing amount of the recombinant virus of claim 32 and a suitable carrier.

37. A vaccine which comprises an effective immunizing amount of the recombinant virus of claim 33 and a suitable carrier.

38. The recombinant virus of claim 1, further comprising a nucleic acid encoding the feline infectious peritonitis virus genome or a portion thereof.

39. The recombinant virus of claim 1, wherein the virus is a swinepox virus and the nonessential region is within the HindIII K fragment.

40. The recombinant virus of claim 1, wherein the virus is a swinepox virus and the nonessential region is within the HindIII K fragment.

41. A vector comprising an isolated nucleic acid encoding a felin CD86 or a feline soluble CD86 ligand, wherein the nucleic acid encodes the amino acid sequence of SEQ ID No. 6.

42. The vector of claim 41, wherein the nucleic acid has a nucleic acid sequence of SEQ ID No. 5.

43. A host cell which comprises a vector of claim 41.

44. The host cell of claim 43, wherein the host cell is a eukaryotic or a prokaryotic cell.

45. The host cell of claim 44, wherein the host cell is selected from the group consisting of E. coli, yeast, COS cells PC12 cells, CHO cells, and GH4C1 cells.

* * * * *

UNITED STATES PATENT AND TRADEMARK OFFICE

CERTIFICATE OF CORRECTION

PATENT NO. : 7,279,168 B2
APPLICATION NO. : 09/303040
DATED : October 9, 2007
INVENTOR(S) : Barbara J. Winslow et al.

It is certified that error appears in the above-identified patent and that said Letters Patent is hereby corrected as shown below:

In Claim 2, line 2, (Col. 115, line 29), after "nucleic acids," delete "each" and insert --wherein each is--.

In Claim 4, line 1, (Col. 115, line 34), "claim 2" should be deleted and replaced with --claim 1--.

In Claim 26, line 3, (Col. 116, line 59), "recominant" should be deleted and replaced with --recombinant--.

Signed and Sealed this

Twenty-first Day of October, 2008

JON W. DUDAS
*Director of the United States Patent and Trademark Office*

UNITED STATES PATENT AND TRADEMARK OFFICE

CERTIFICATE OF CORRECTION

PATENT NO. : 7,279,168 B2
APPLICATION NO. : 09/303040
DATED : October 9, 2007
INVENTOR(S) : Barbara J. Winslow et al.

It is certified that error appears in the above-identified patent and that said Letters Patent is hereby corrected as shown below:

In Claim 1, line 3 (Col. 115, line 24), after “viral genome” delete “of a virus”.

In Claim 2, line 2 (Col. 115, line 29), after “nucleic acids,” insert --wherein each is--.

In Claim 5, line 2 (Col. 115, line 38), after “virus is” delete “raccoonpox virus” and after “a swinepox virus” delete “or a feline herpesvirus”.

In Claim 6, line 2 (Col. 115, line 40), delete “acids” and replace with --acid--.

In Claim 7, line 2 (Col. 115, line 44), delete “acids” and replace with --acid--.

In Claim 12, line 2 (Col. 115, line 64), delete “acids” and replace with --acid--.

In Claim 17, line 1 (Col. 116, line 30), after “The recombinant” delete “feline herpes” and after “claim 12” insert --wherein the recombinant virus is a feline herpesvirus--.

In Claim 25, line 3 (Col. 116, line 55), “redombinant” should be deleted and replaced with --recombinant--.

In Claim 30, line 3 (Col. 117, line 6), “nucleis” should be deleted and replaced with --nucleic-- and after “amount effective” insert --to--.

In Claim 34, lines 1-3 (Col. 117, lines 20-22), “resombinant” should be deleted and replaced with --recombinant-- and after “GM-CSF” delete “or” and replace with a --,-- and after “p35” delete “and” and insert --or feline IL-12--.

In Claim 35, lines 2-3 (Col. 117, lines 24-25), after “GM-CSF” delete “or” and replace with a --,-- and after “p35” delete “and” and insert --or feline IL-12--.

Signed and Sealed this
Fourth Day of January, 2011

David J. Kappos
*Director of the United States Patent and Trademark Office*

In Claim 40, line 3 (Col. 118, line 13), after “HindIII” delete “K” and insert --N--.

In Claim 41, line 2 (Col. 118, line 15), “felin” should be deleted and replaced with --feline--.

In Claim 45, lines 2-3 (Col. 118, lines 24-25), after “consisting of” insert a --:--
and after “COS cells” insert a --,--.